(12) United States Patent
Chadha et al.

(10) Patent No.: US 11,499,954 B2
(45) Date of Patent: *Nov. 15, 2022

(54) WIRELESS EXPOSURE MONITOR

(71) Applicant: Applied Particle Technology, Inc., St. Louis, MO (US)

(72) Inventors: Tandeep Singh Chadha, Boise, ID (US); Jiaxi Fang, Menlo Park, CA (US); Pratim Biswas, Chesterfield, MO (US)

(73) Assignee: Applied Particle Technology, Inc., St. Louis, MO (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/949,220

(22) Filed: Oct. 20, 2020

(65) Prior Publication Data

US 2021/0033586 A1 Feb. 4, 2021

Related U.S. Application Data

(63) Continuation-in-part of application No. 16/871,213, filed on May 11, 2020, now abandoned, which is a
(Continued)

(51) Int. Cl.
*G01N 33/00* (2006.01)
*G01N 15/02* (2006.01)
*G01N 15/06* (2006.01)

(52) U.S. Cl.
CPC ..... *G01N 33/0075* (2013.01); *G01N 15/0266* (2013.01); *G01N 15/0656* (2013.01); *G01N 33/0031* (2013.01); *G01N 33/0065* (2013.01)

(58) Field of Classification Search
CPC .......... G01N 33/0075; G01N 15/0266; G01N 15/0656; G01N 33/0031; G01N 33/0065;
(Continued)

(56) References Cited

U.S. PATENT DOCUMENTS 7,389,158 B2 6/2008 Desrochers et al.
8,190,367 B2* 5/2012 Bassa ................... B60H 3/0085
73/31.03
(Continued)

FOREIGN PATENT DOCUMENTS

GB 2420616 A 5/2006

OTHER PUBLICATIONS

U.S. Office Action dated Oct. 4, 2019 in U.S. Appl. No. 16/293,499.
(Continued)

*Primary Examiner* — Sisay Yacob
(74) *Attorney, Agent, or Firm* — Weaver Austin Villeneuve & Sampson LLP

(57) ABSTRACT

Systems, apparatuses, and methods for monitoring an environment are provided. One system includes a monitoring unit positioned within an environment and including an acoustic sensor configured to generate detected acoustic data regarding acoustics in the environment, and a controller having one or more processors and one or more non-transitory memory devices that store instructions for controlling the one or more first processors to receive and store the detected acoustic data, determine, based on the detected acoustic data, whether a noise is above a threshold, and determine, based on the detected acoustic data and that the noise is above the threshold, an estimated source of the noise.

37 Claims, 16 Drawing Sheets

Related U.S. Application Data continuation of application No. 16/293,499, filed on Mar. 5, 2019, now Pat. No. 10,670,572.

(60) Provisional application No. 62/638,958, filed on Mar. 6, 2018.

(58) Field of Classification Search
CPC ........... G01N 15/0205; G01N 15/1459; G01N 2015/0046; G01N 2015/1486
See application file for complete search history.

(56) References Cited

U.S. PATENT DOCUMENTS

| | | | |
|---|---|---|---|
| 8,781,633 B2 * | 7/2014 | Fata | H04L 43/0817 700/276 |
| 9,141,094 B2 | 9/2015 | Pariseau et al. | |
| 10,670,572 B2 | 6/2020 | Chadha et al. | |
| 2002/0144537 A1 * | 10/2002 | Sharp | G01N 33/0075 73/31.07 |
| 2003/0016128 A1 | 1/2003 | Lutz et al. | |
| 2006/0173580 A1 * | 8/2006 | Desrochers | G01N 33/0075 73/31.01 |
| 2009/0265037 A1 * | 10/2009 | Bassa | B60H 1/008 700/306 |
| 2010/0274366 A1 * | 10/2010 | Fata | H04L 12/2818 700/8 |
| 2010/0295672 A1 | 11/2010 | Hyland et al. | |
| 2013/0213115 A1 | 8/2013 | Chu et al. | |
| 2014/0347663 A1 | 11/2014 | Rodes et al. | |
| 2015/0212057 A1 | 7/2015 | Darveau | |
| 2016/0109349 A1 | 4/2016 | Volckens et al. | |
| 2016/0202224 A1 * | 7/2016 | Lloyd | G05D 7/01 73/865.8 |
| 2017/0284690 A1 | 10/2017 | Lipanov | |
| 2017/0370809 A1 | 12/2017 | Miller-Lionberg et al. | |
| 2019/0277822 A1 | 9/2019 | Chadha et al. | |

OTHER PUBLICATIONS

U.S. Notice of Allowance dated Jan. 27, 2020 in U.S. Appl. No. 16/293,499.

International Search Report and Written Opinion dated Jun. 19, 2019 from PCT Application No. PCT/US2019/020811.

International Preliminary Report on Patentability dated Sep. 18, 2020 from PCT Application No. PCT/US2019/020811.

Applied Particle Technology, "Minima" brochure, 2017, 2 pp.

Li, J., et al., "Optical characterization studies of a low-cost particle sensor," Aerosol and Air Quality Research, 17: 2017, pp. 1691-1704, <doi: 10.4209/aaqr.2017.02.0085>.

Wang, Y., et al., "Laboratory evaluation and calibration of three low-cost particle sensors for particulate matter measurement," Aerosol Science and Technology, vol. 49, 2015, pp. 1063-1077, <doi: 10.1080/02786826.2015.1100710>.

Li, J., et al., "Spatiotemporal distribution of indoor particulate matter concentration with a low-cost sensor network," Building and Environment 127, 2018, pp. 138-147. <doi: 10.1016/j.buildenv.2017.11.001>.

Li, J., et al., "Robust algorithms & innovative designs for low cost PM sensors: calibration, characterization, and application," Air Sensors International Conference, Oakland, CA, Sep. 13, 2018, 20 pp.

U.S. Appl. No. 16/871,213, filed May 11, 2020, Chadha et al.

* cited by examiner

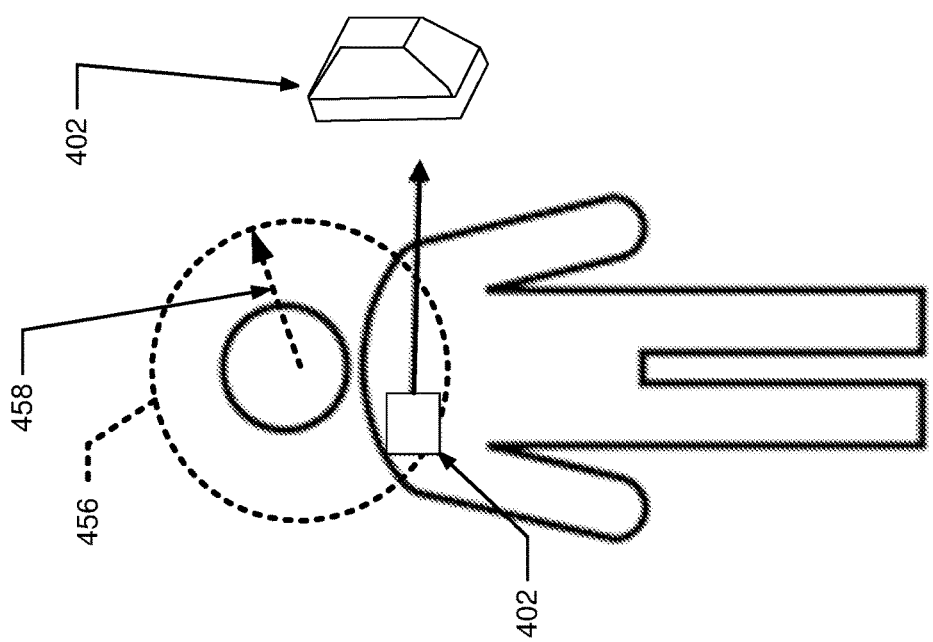
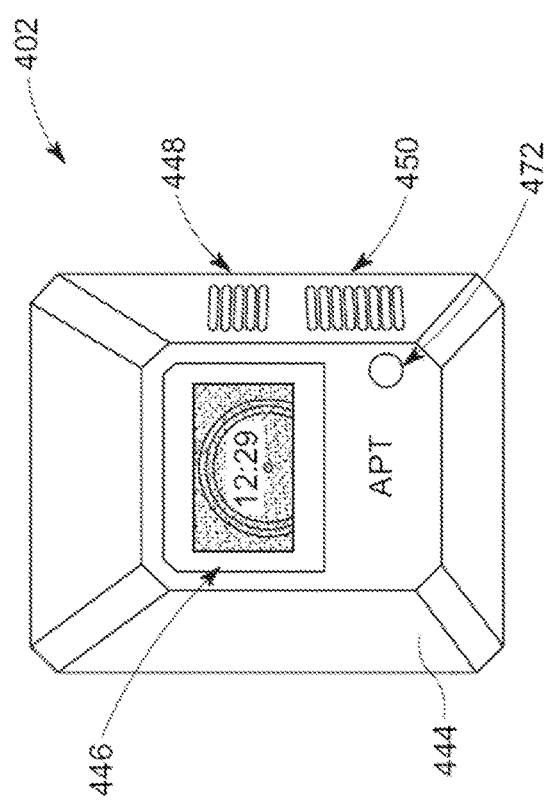
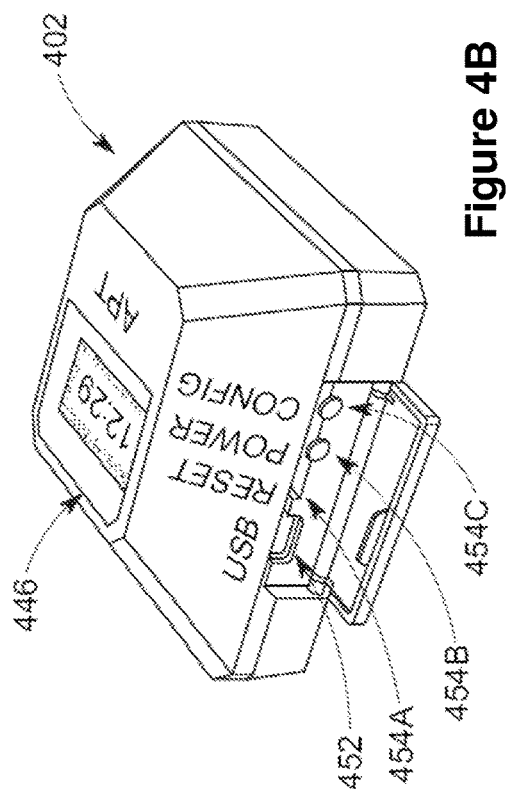

WIRELESS EXPOSURE MONITOR

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

In many industries and environments, the potential exists that personnel, workers, and persons may be exposed to harmful conditions, such as aerosols, gases, volatile organic compounds (VOCs), temperature, humidity, and noise. It is desirable to detect the presence of harmful conditions and determine whether there has been any unsafe exposure to these conditions.

SUMMARY

In some embodiments, a system may be provided. The system may include a monitoring unit positioned within an environment and including an acoustic sensor configured to generate detected acoustic data regarding acoustics in the environment, and a controller having one or more processors and one or more non-transitory memory devices that store instructions for controlling the one or more first processors to receive and store the detected acoustic data, determine, based on the detected acoustic data, whether a noise is above a threshold, and determine, based on the detected acoustic data and that the noise is above the threshold, an estimated source of the noise.

In some embodiments, the estimated source of the noise may be an activity performed in the environment.

In some embodiments, the system may further include a second sensor configured to generate second data. The sensor may be a camera, a temperature sensor, a location sensor, an air quality sensor, and a gas sensor. The one or more non-transitory memory devices may store further instructions for controlling the one or more processors to receive and store the second data, and determine, based at least in part on the acoustic data and the second data, the source of the acoustic.

In some such embodiments, the second sensor may be a location sensor configured to generate location data about a location of the monitoring unit, and the one or more non-transitory memory devices may store further instructions for controlling the one or more processors to determine, based at least in part on, the source of the noise.

In some embodiments, the system may further include a notification mechanism configured to present a person with a notification related to the detected acoustic data, and the one or more non-transitory memory devices stores further instructions for controlling the one or more processors to cause, based on the detected acoustic data, the notification mechanism to present the person with the notification related to the detected acoustic data.

In some embodiments, the one or more non-transitory memory devices may store further instructions for controlling the one or more processors to determine whether a second noise will exceed a second threshold over a period of time in the future.

In some such embodiments, the second noise may be the noise.

In some embodiments, the one or more non-transitory memory devices may further store acoustic information relating to associations between acoustic data and sources of acoustics, and the determination of the estimated source of the noise may be further based on the acoustic information.

In some embodiments, the one or more non-transitory memory devices may further store acoustic information relating to associations between acoustic data and functionality of sources of acoustics, and to determine whether a source of acoustics is functioning properly and/or should be maintained.

In some such embodiments, the sources of acoustics may include operating machinery, vehicles, or equipment.

In some embodiments, a system may be provided. The system may include a monitoring unit positioned within an environment and including a temperature sensor configured to generate temperature data, and a relative humidity sensor configured to generate humidity data, a notification mechanism configured to present a person with a notification related to a heat stress determination, and a controller comprising one or more first processors and one or more first non-transitory memory devices that store instructions for controlling the one or more first processors to receive and store the temperature data and the humidity data, determine, based on the temperature data and the humidity data, an estimated heat stress in the environment, determine whether the estimated heat stress in the environment is above a threshold, and cause, based on the heat stress determination, the notification mechanism to present the person with the notification related to the heat stress determination.

In some embodiments, the temperature data may be ambient temperature around the monitoring unit.

In some embodiments, the temperature data may be a body temperature of a person.

In some embodiments, the system may further include one or more additional sensors selected from the group consisting of a heart rate sensor and a light intensity sensor, and the determination of the estimated heat stress in the environment may be further based on data generated by the one or more additional sensors.

In some embodiments, the one or more non-transitory memory devices may further store instructions to access climate information relating to climate information in the environment, and the determination of the estimated heat stress in the environment may be further based on the accessed climate information.

In some embodiments, a system may be provided. The system may include a monitoring unit positioned within an environment and including a camera configured to generate image/video data of the environment, and a controller comprising one or more first processors and one or more first non-transitory memory devices that store instructions for controlling the one or more first processors to cause the camera to generate image/video data, receive and store the image/video data, and determine, in real-time and based on the image/video data, an activity performed within the environment.

In some embodiments, the controller may be positioned in the monitoring unit, and the determination may be made by the controller in the monitoring unit.

In some embodiments, the system may further include a first communications unit with an antenna configured to transmit data between the monitoring unit and, directly or indirectly, a remote computing unit, and the remote computing unit may be positioned outside the environment and containing one or more second processors, one or more second communications unit, and one or more second non-transitory memory devices that stores instructions for controlling the one or more second processors. The one or more first non-transitory memory devices may further store instructions for controlling the one or more first processors to transmit, using the first communications unit, the image/video data to the remote computing unit, and the one or more second non-transitory memory devices may store instructions for controlling the one or more second processors to receive and store the image/video data, and determine, based on the image/video data the activity performed within the environment.

In some embodiments, the system may further include an air quality sensor configured to generate particle data regarding particles in the environment and communicatively connected with the controller, and the one or more non-transitory memory devices may further store instructions to determine, based on the particle data generated by the air quality sensor, whether a first exposure threshold has been exceeded for the monitoring unit, and cause the camera to take image/video data when a determination is made that the first exposure threshold has been exceeded.

In some embodiments, a system may be provided. The system may include a monitoring unit positioned within an environment and including a gas sensor configured to generate concentration data of a gas in the environment, and a controller comprising one or more first processors and one or more non-transitory memory devices that store gas information and instructions for controlling the one or more first processors to cause the gas sensor to generate concentration data of the gas in the environment, receive and store the concentration data, determine, based on the concentration data, a chemical composition of the gas in the environment, access gas information that relates to an association between the gas and one or more sources of the gas, and determine, based on the chemical composition of the gas in the environment and the gas information, one or more sources of the gas.

In some embodiments, the one or more non-transitory memory devices may further store instructions for controlling the one or more first processors to determine whether the chemical composition is increasing or decreasing.

In some embodiments, the one or more non-transitory memory devices may further store instructions for controlling the one or more first processors to determine whether the chemical composition if the gas is above a threshold.

In some embodiments, a system may be provided. The system may include a monitoring unit positioned within an environment and including a sensor configured to detect air particles, a gas, or acoustic signals in the environment and generate data regarding the detected air particles, the gas, or acoustic signals, and a first communications unit with an antenna configured to transmit data between the monitoring unit and, directly or indirectly, a remote computing unit. The system may also include a controller communicatively connected with the sensor and comprising one or more first processors and one or more first non-transitory memory devices that store instructions for controlling the one or more first processors to receive and store the data generated by the sensor, access location information relating to a location of the monitoring unit within the environment, determine, based on the data generated by the sensor and the location information, amounts or concentrations in the environment that are associated with the detected air particles, a gas, or acoustic signals, and generate a map of the determined amounts or concentrations, in the environment, that are associated with the detected air particles, gas, or acoustic signals in the environment.

In some embodiments, the determined amounts or concentrations may include datapoints interpolated from the data generated by the sensor.

In some embodiments, the one or more first non-transitory memory devices may further store instructions for controlling the one or more first processors to access geographic information of the environment, and the determination may be further based on the geographic information of the environment.

In some embodiments, the one or more first non-transitory memory devices may further store instructions for controlling the one or more first processors to access air flow data related to air flow within the environment, and the determination may be further based on the air flow data.

In some such embodiments, the air flow data may include a flow rate and a direction of an air flow within the environment relative to the location of the monitoring unit within the environment.

In some such embodiments, the air flow data may include data from one or more external sources.

In some embodiments, the one or more first non-transitory memory devices may further store instructions for controlling the one or more first processors to determine, based on the data generated by the sensor, a location of a source of the detected air particles, gas, or acoustic signals in the environment.

In some embodiments, a system may be provided. The system may include a monitoring unit positioned proximate to a boundary of an environment and including a sensor configured to detect air particles or a gas and generate data regarding the detected air particles or the gas, and a first communications unit with an antenna configured to transmit data between the monitoring unit and, directly or indirectly, a remote computing unit. The system may further include a notification mechanism configured to generate a notification, and a controller communicatively connected with the sensor and comprising one or more first processors and one or more first non-transitory memory devices that store instructions for controlling the one or more first processors to receive and store the data generated by the sensor, access location information relating to a location of the monitoring unit, determine, based at least in part on the data generated by the sensor, whether amounts or concentrations associated with the detected air particles or gas have exceeded a threshold, determine, based at least in part on the data generated by the sensor and the location information, whether the detected air particles or gas are exiting or entering the environment, and cause, based at least in part on the determinations, the notification mechanism to generate the notification related to the detected air particles or gas.

In some embodiments, the one or more non-transitory memory devices may further store instructions for controlling the one or more first processors to determine whether the amounts or concentrations associated with the detected air particles or gas is increasing or decreasing.

In some embodiments, the one or more first non-transitory memory devices may further store instructions for controlling the one or more first processors to access air flow data related to air flow within and/or around the environment, and the determination of whether the detected air particles or gas are exiting or entering the environment may be further based on the air flow data.

In some such embodiments, the air flow data may include a flow rate and a direction of an air flow within the environment relative to the location of the monitoring unit within the environment.

In some such embodiments, the air flow data may include data from one or more external sources.

In some embodiments, the system may further include a camera configured to generate images and/or video of an area covering or near a portion of the boundary. The determination of whether amounts or concentrations associated with the detected air particles or gas have exceeded a threshold may be further based on the images and/or video generated by the camera, and the determination of whether the detected air particles or gas are exiting or entering the environment may be further based on the images and/or video generated by the camera.

In some embodiments, the system may further include a camera configured to generate images and/or video of an area covering or near a portion of the boundary. The one or more first non-transitory memory devices may further store instructions for controlling the one or more first processors to determine an opacity of air in the area covering or near the portion of the boundary, the determination of whether amounts or concentrations associated with the detected air particles or gas have exceeded a threshold may be further based on the opacity of the air, and the determination of whether the detected air particles or gas are exiting or entering the environment may be further based on the opacity of the air.

In some embodiments, the system may further include a laser sensor configured to generate distance data associated with a measured distance between the laser sensor and an object. The determination of whether amounts or concentrations associated with the detected air particles or gas have exceeded a threshold may be further based on the distance data, and the determination of whether the detected air particles or gas are exiting or entering the environment may be further based on the distance data.

In some embodiments, a system may be provided. The system may include a monitoring unit positioned within an environment and that includes an air quality sensor configured to generate particle data regarding particles in the environment, a first communications unit with an antenna configured to transmit data between the monitoring unit and, directly or indirectly, a remote computing unit, and a controller including one or more first processors and one or more first non-transitory memory devices that store instructions for controlling the one or more first processors to cause the air quality sensor to generate particle data about particles in the environment, and transmit, using the first communications unit, the particle data generated by the air quality sensor to the remote computing unit. In some embodiments, the remote computing unit may be positioned outside the environment and may contain one or more second processors, one or more second communications unit, and one or more second non-transitory memory devices that stores instructions for controlling the one or more second processors to receive and store the particle data, and determine, based on the received particle data generated by the air quality sensor, whether a first exposure threshold has been exceeded for the monitoring unit.

In some embodiments, the first communications unit and controller may be configured as a single unit.

In some embodiments, the monitoring unit may further includes a temperature sensor configured to generate temperature data, a pressure sensor configured to generate pressure data, and a relative humidity sensor configured to generate pressure data. The one or more first non-transitory memory devices of the monitoring unit may store further instructions for controlling the one or more first processors to cause the air temperature sensor to generate temperature data, cause the air pressure sensor to generate pressure data, cause the relative humidity sensor to generate humidity data, and transmit, using the first communications unit, the temperature data, pressure data, and humidity data to the remote computing unit. The one or more second non-transitory memory devices of the remote computing unit may store further instructions for controlling the one or more second processors to receive and store the temperature data, the pressure data, and the humidity data, determine, based on the received particle data, temperature data, pressure data, and the humidity data, first adjusted particle information, and determine, based on the first adjusted particle information, whether the first exposure threshold has been exceeded.

In some embodiments, the system may further include a notification mechanism configured to present a person with a notification related to the particle data. The one or more second non-transitory memory devices of the remote computing unit may store further instructions for controlling the one or more second processors to cause, based on the particle data, the notification mechanism to present the person with the notification related to the particle data.

In some embodiments, the one or more second non-transitory memory devices of the remote computing unit may further stores environmental data about the environment. The one or more second non-transitory memory devices of the remote computing unit stores further instructions for controlling the one or more second processors to access the environmental data, determine, based on the received particle data and the environmental data, second adjusted particle information, and determine, based on the second adjusted particle information, whether the first exposure threshold has been exceeded.

In some such embodiments, the environmental data may include one or more of: material safety data sheet (MSDS) data, weather data, historical detected particle data, data generated by another monitoring unit in the environment, data regarding activity being performed in the environment, and public data.

In some embodiments, the system may further include a second monitoring unit positioned within the environment and that may include a second air quality sensor configured to generate data regarding particles in the environment, a third communications unit with an antenna configured to transmit data between the second monitoring unit and the remote computing unit, and a second controller comprising one or more third processors and one or more third non-transitory memory devices that store instructions for controlling the one or more third processors to cause the second air quality sensor to generate second particle data about particles in the environment, and transmit, using the third communications unit, the second particle data generated by the air quality sensor to the remote computing unit. The first communications unit may be further configured to transmit data between the second monitoring unit, and the one or more second non-transitory memory devices of the remote computing unit may store further instructions for controlling the one or more second processors to receive and store the second particle data, and determine, based on the received second particle data, whether the first exposure threshold has been exceeded for the second monitoring unit.

In some such embodiments, the one or more second non-transitory memory devices of the remote computing unit may store further instructions for controlling the one or more second processors to determine, based on the received particle data and the second particle data, whether the particle data is offset from the second particle data by a first offset.

In some such embodiments, the monitoring unit may be a mobile monitoring unit configured to be moved within the environment, and the second monitoring unit may be a stationary monitory unit in a fixed position within the environment.

In some such embodiments, the monitoring unit and the second monitoring unit may be mobile monitoring units configured to be moved within the environment.

In some embodiments, the first exposure threshold may include a time-weighted average, an acute exposure limit, an upper exposure limit, a lower exposure limit, a combustible limit, and a short-term exposure limit.

In some embodiments, the monitoring unit may further include an accelerometer, a gyroscope, and a microphone, and the one or more first non-transitory memory devices stores further instructions for controlling the one or more first processors to cause the accelerometer to generate accelerometer data, the gyroscope to generate gyroscopic data, and the microphone to generate sound data, and transmit, using the first communications unit, the accelerometer data, gyroscopic data, and sound data, to the remote computing unit. The one or more second non-transitory memory devices may store further instructions for controlling the one or more second processors to determine, based on the accelerometer data, gyroscopic data, and sound data, an activity being performed within a first distance from the monitoring unit.

In some such embodiments, the one or more second non-transitory memory devices may store further instructions for controlling the one or more second processors to determine, based on the accelerometer data, gyroscopic data, and sound data, whether a wearer of the monitoring unit is performing an activity.

In some embodiments, the one or more second non-transitory memory devices of the remote computing unit may store further instructions for controlling the one or more second processors to determine, based on the received particle data and the second particle data, whether the first exposure threshold has been exceeded for the monitoring unit.

In some embodiments, a monitoring unit may be provided. The monitoring unit may include a case with an inlet and an outlet, an air quality sensor fluidically connected to the inlet and the outlet, and configured to generate particle data regarding particles in air drawn through the inlet, a communications unit with an antenna configured to transmit data between the monitoring unit and a remote computing unit, and a controller that may include one or more processors and one or more non-transitory memory devices. The case may encompass the air quality sensor, the communications unit, and the controller, and the one or more non-transitory memory devices may store instructions for controlling the one or more processors to cause the air quality sensor to generate particle data about particles in air drawn through the inlet, and transmit, using the communications unit, the data generated by the air quality sensor to the remote computing unit.

In some embodiments, the monitoring unit may further include a notification mechanism configured to present a person with a notification related to the particle data, and the one or more non-transitory memory devices may store further instructions for controlling the one or more processors to cause, based on the particle data, the notification mechanism to present the person with the notification related to the particle data.

In some such embodiments, the notification mechanism may include a display on the case that is configured to present the notification to the person.

In some such embodiments, the one or more non-transitory memory devices may store further instructions for controlling the one or more processors to receive a remote instruction from the remote computing unit, and cause, based on the remote instruction received from the remote computing unit, the notification mechanism to present the person with the notification related to the particle data.

In some such embodiments, the notification may be one or more of alarm, alert, message, an auditory output, an electronic communication, an electromagnetic communication, a visual output, and a tactile output.

In some embodiments, the monitoring unit may further include a temperature sensor, a pressure sensor, and a relative humidity sensor. The one or more non-transitory memory devices may store further instructions for controlling the one or more processors to cause the air temperature sensor to generate temperature data, cause the air pressure sensor to generate pressure data, cause the relative humidity sensor to generate humidity data, and transmit, using the communications unit, the temperature data, pressure data, and humidity data to the remote computing unit.

In some embodiments, the monitoring unit may further include an accelerometer, a gyroscope, a microphone, and a camera. The one or more non-transitory memory devices may store further instructions for controlling the one or more processors to cause the accelerometer to generate accelerometer data, cause the gyroscope sensor to generate gyroscopic data, cause the microphone to generate sound data, cause the camera to generate imaging data, and transmit, using the communications unit, the accelerometer data, gyroscopic data, sound data, and imaging data to the remote computing unit.

In some embodiments, the communications unit may be further configured to gather position data about a position of the monitoring unit within an environment, and the one or more non-transitory memory devices may store further instructions for controlling the one or more processors to cause the communications unit is further configured to gather position data about the position of the monitoring unit within an environment, and transmit the position data to the remote computing unit.

In some embodiments, the monitoring unit may further include a second air quality sensor fluidically connected to the inlet and the outlet, and configured to generate second particle data regarding particles in air drawn through the inlet. The one or more non-transitory memory devices may store further instructions for controlling the one or more processors to cause the second air quality sensor to generate second particle data about particles in air drawn through the inlet, determine, based on the particle data and the second particle data, whether the particle data is offset from the second particle data by a first offset, and transmit information related to the determination of the first offset to the remote computing unit.

In some embodiments, the monitoring unit may further include wearable features that are configured to enable the monitoring unit to be worn by a person within that person's breathing zone.

In some embodiments, another monitoring unit may be provided. The other monitoring unit may include a case with an inlet and an outlet, an air quality sensor fluidically connected to the inlet and the outlet, and configured to generate data regarding particles in air drawn through the inlet, a communications unit with an antenna configured to transmit data between the monitoring unit and a remote computing unit, a temperature sensor configured to generate temperature data, a pressure sensor configured to generate pressure data, a relative humidity sensor configured to generate humidity data, an accelerometer configured to generate accelerometer data, a gyroscope configured to generate gyroscopic data, a microphone configured to generate sound data, a camera configured to generate imaging data, and a controller comprising one or more processors and one or more non-transitory memory devices.

In some embodiments, a method for monitoring conditions of an environment may be provided. The method may include generating, using an air quality sensor on a monitoring unit positioned within the environment, particle data regarding particles in the environment, transmitting the particle data from the monitoring unit to a remote computing unit outside the environment, and determining, based on the particle data generated by the air quality sensor, whether a first threshold has been exceeded.

In some embodiments, the transmitting may be performed simultaneously with the generating.

In some embodiments, the determining may be at least partially performed on the remote computing unit.

In some embodiments, the method may further include generating, using a temperature sensor, a pressure sensor, and a relative humidity sensor on the monitoring unit, temperature data, pressure data, and humidity data, respectively, transmitting the temperature data, pressure data, and humidity data from the monitoring unit to the remote computing unit, determining, based on the particle data, temperature data, pressure data, and humidity data, adjusted particle information, and determining, based on the adjusted particle information, and whether the first threshold has been exceeded.

In some embodiments, the method may further include generating, using an accelerometer, a gyroscope, and a microphone on the monitoring unit, accelerometer data, gyroscopic data, and sound data, respectively, transmitting the accelerometer data, gyroscopic data, and sound data from the monitoring unit to the remote computing unit, and determining, based on accelerometer data, gyroscopic data, and sound data, whether an activity is being performed within a first distance of the monitoring unit.

In some such embodiments, the method may further include determining, based on accelerometer data, gyroscopic data, and sound data, whether the activity is being performed by a wearer of the monitoring unit.

In some such embodiments, the method may further include generating, based on one or more of accelerometer data, gyroscopic data, and sound data, imaging data using a camera on the monitoring unit, and transmitting the imaging data from the monitoring unit to the remote computing unit.

In some embodiments, an apparatus for monitoring one or more environmental parameters including aerosol properties, gas concentrations, temperature, humidity or noise may be provided. The apparatus may be capable of wirelessly transmitting data generated by one or more sensors and may include (a) one or more sensor(s) for generating data corresponding to one or more environmental parameters such as aerosol properties, gas concentrations, temperature, humidity or noise, (b) a microprocessor/microcontroller to read the data and transmit wirelessly, (c) a screen to display the data, (d) an optional memory card to store the data, (e) a cloud server for receiving the data, applying, algorithms and displaying the data, and (f) an optional imaging device to take the image/record video while the data is being recorded.

In some embodiments, the data corresponding to measured aerosol properties may include one or more of particle mass concentrations (PM0.5, PM1, PM2.5, PM4, PM5, PM10), the particle number counts in different size bins, particle refractive index, fractal dimension, chemical composition, and other material properties.

In some embodiments, the apparatus may be placed on a person in the breathing zone to monitor personal exposure.

In some embodiments, the apparatus may be placed at different locations at an industrial site.

In some embodiments, the apparatus may be used to prevent exposure to a person above the action levels and permissible exposure limits as defined by NIOSH/OSHA.

In some embodiments, real-time alerts may be generated based on the data.

In some embodiments, the data may be transmitted wirelessly via WiFi, Bluetooth, cellular or LoRAwan.

In some embodiments, the apparatus may further include a camera that may be configured and placed to take images/record video while the monitor is running.

In some such embodiments, the camera may take an image or records video when an aspect of the data goes above a certain level.

In some embodiments, the apparatus may be used as a wearable exposure monitor for occupational safety and health applications.

In some embodiments, the apparatus may be used as an industrial site monitor.

In some embodiments, data from a network of monitors may be taken to create a map of air quality in real-time.

In some embodiments, the data is used to calculate the concentrations of certain elements/compounds including but not limited to silica, hexavalent chromium, and lead.

In some embodiments, the data may be used for process control for emission sources.

These and other features of the disclosure will be discussed in more detail below with reference to the drawings.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIGS. 4A and 4B depict plan and off-angle views of an example mobile monitoring unit; FIG. 4C depicts the example mobile monitoring unit positioned within a wearer's breathing zone.

DETAILED DESCRIPTION

Figure 1:
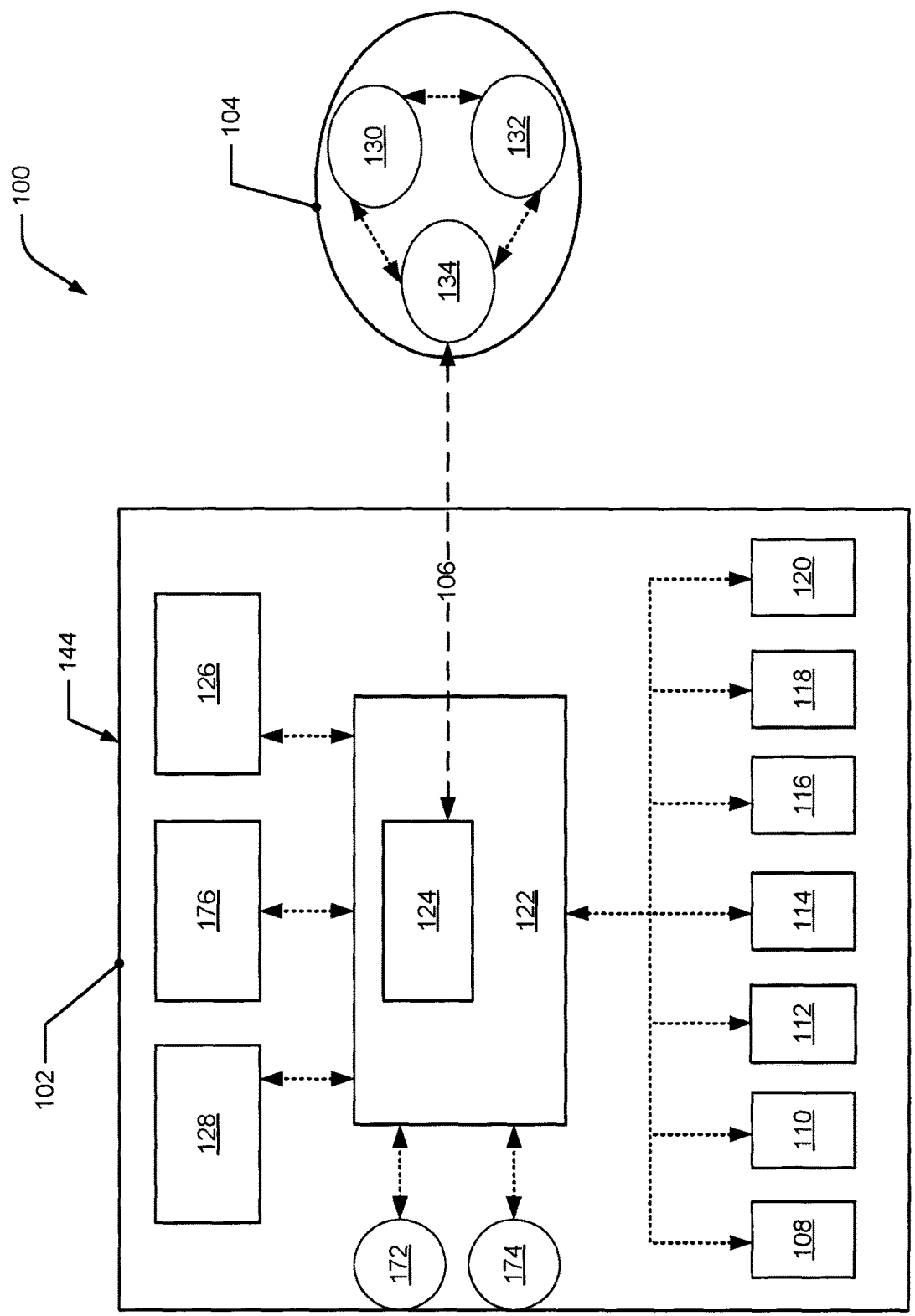
FIG. 1 depicts a first example system for monitoring environmental conditions.

In the following description, certain details are set forth in order to assist understanding the presented embodiments. The disclosed embodiments may be practiced without some or all of these details. Thus, while the disclosed embodiments will be described in conjunction with the certain details, it should be understood that these are not intended to limit the disclosed embodiments. Further, in some instances, well-known process operations have not been described in detail to clarify the disclosed embodiments.

Definitions

"Cloud computing" uses one or more servers, data stores, or other computational resources that are hosted remotely, i.e., not on an end user's desktop or laptop computer, handheld computational device, or other device directly accessible to the user. Cloud-based computational resources are generally accessible via a network such as the internet. Cloud-based resources may store, manage, and/or process data. Frequently, the resources are shared software and/or hardware. Cloud-based computational resources provide information, storage, and/or processing resources to computers and other devices upon request. Access to cloud resources may be by wired or wireless communication.

"Edge computing" uses one or more servers, data stores, or other computational resources that are hosted on site, locally, using a similar infrastructure as in cloud computing. As an example, edge computing may be performed using private networks where the user might not want data to go to the internet.

"Mobile Monitoring Unit" as used herein means a monitoring device that is not at a fixed location while monitoring. Typically, a mobile monitoring device moves about while monitoring. As examples, a mobile monitoring device may be worn by a user (it is wearable), be positioned on a flying device such as a drone, or positioned on a terrestrial vehicle.

"Sensor" as used herein means any device capable of detecting and/or measuring a physical property. Examples include a particle sizer, an air quality monitor, a specific matter sensor, a temperature sensor (e.g., thermocouple, resistance temperature detector, negative temperature coefficient thermistor), a relative humidity sensor (e.g., capacitive, resistive, thermally conductive), a pressure sensor (e.g., a piezometer, a manometer, etc.), a microphone (e.g., a dynamic, condenser, piezoelectric, carbon, ribbon), an inertial sensor (e.g., an accelerometer and/or gyroscope), and/or a gas sensor (e.g., a sensor configured to detect one or more specific gases such as carbon monoxide (CO), carbon dioxide ($CO_2$), Ozone, nitrogen oxides (NOx), volatile organic compounds (VOCs), hydrogen cyanide (HCN). Sensors may employ any of various transduction mechanisms including mechanical (including electromechanical), optical, chemical, biomimetic, and/or electrical.

"Stationary Monitoring Unit" as used herein means a monitoring unit that is positioned in a fixed location. In certain embodiments, a stationary monitoring unit is used in conjunction with a mobile monitoring unit. A stationary unit may be affixed to an immobile object, such as a wall, building, fence, pole, structural frame, piece of equipment (e.g., a generator). In some implementations, the stationary unit is movable so that it can be repositioned to other environments or locations within the same environment; during monitoring the stationary unit may remain at the fixed location.

"Wearable Monitoring Unit" as used herein means a type of mobile monitoring unit that is affixed to or affixable to a wearer's body or clothing. In certain embodiments, it is affixable within the breathing zone of the wearer, which may be defined as a hemisphere that extends in front of the wearer's face and that has a radius of approximately 15 to 30 centimeters (or approximately 6 to 11 inches) measured from the midpoint of a line joining the wearer's ears, which is around the wearer's nose and mouth. In certain embodiments, the wearable unit is relatively small, e.g., no dimension is greater than about 2 inches (5 cm) or about 3 inches (8 cm).

INTRODUCTION

In many industries and certain environments (e.g., cities and areas were people work and reside), individuals such as workers may be exposed to harmful conditions, such as aerosols, gases, volatile organic compounds (VOCs), temperature, humidity, and noise. In some industries, governmental or other regulations set limits of acceptable levels and exposures to such conditions and it is therefore desirable to detect and monitor these potentially hazardous conditions. These regulations may also require that some environmental conditions be periodically or consistently monitored in order to detect the presence of harmful conditions and to determine that conditions have exceeded a particular threshold. In some instances, an industrial hygienist or other person may perform testing or sampling in order to monitor and determine such conditions which may be input to one or more industrial hygiene reports.

There is a significant need for real-time understanding of occupational exposure risks. This includes occupational exposure risks during national and global health crises, such as the COVID-19 pandemic, and for challenges caused by various health situations. This also includes millions of workers using personal protective equipment (PPE) on a regular basis to help protect them from illnesses such as silicosis, lung cancer, heat stress, and/or hearing loss, for example. However, there are significant challenges in controlling, preventing, and/or assessing various exposures to such occupational exposure risks. For example, a significant difficulty in controlling exposures to crystalline silica is the current inability to rapidly assess exposure risk, because results typically take weeks to obtain using current analysis techniques. There is also a need to reduce occupational exposures because such exposures are not only damaging to worker health, but are resulting in economic losses, job losses, and lower productivity associated with compliance.

Additionally, many traditional techniques and monitors for detecting and monitoring environmental conditions have serious drawbacks. For instance, many monitors do not provide real-time monitoring, but instead collect data at one location which is later analyzed at another location, such as a laboratory. For instance, the industrial hygienist may take samples of a particular industrial location, like a construction site, and then send those samples to a laboratory for processing and analysis. Additionally, some traditional monitors and techniques are not performed within the appropriate locations. For instance, the most accurate airborne exposures are performed within a person's breathing zone (the hemisphere that extends in front of a person's face and that has a radius of approximately 15 to 30 centimeters (or approximately 6 to 12 inches) measured from the midpoint of a line joining the that person's ears, which is around the person's nose and mouth), but many monitors and techniques do not take measurements from within this area. Furthermore, traditional monitors and techniques have limited sensing and output capabilities. Some conventional monitors and techniques may be limited in the size and type of particles detected, and may only output raw, sensed data and not data relating to exposure levels, or time weighted averages of exposures. Many conventional monitors and techniques are also time-consuming and expensive, and therefore not practicable.

Example Systems

Disclosed herein are systems and techniques for monitoring environmental conditions. FIG. 1 depicts a first example system 100 for monitoring environmental conditions. System 100 includes a first monitoring unit 102, a remote computing unit 104 (e.g., a cloud computing unit), and a communications link 106 between the first monitoring unit 102 and the remote computing unit 104. The first monitoring unit 102 may be a mobile, stationary, or wearable monitoring unit. The first monitoring unit 102 may include one or more sensors, such as an air quality sensor 108, a temperature sensor 110, a pressure sensor 112, a relative humidity sensor 114, an accelerometer 116, a gyroscope 118, an acoustic sensor (e.g., a microphone) 120, or any combination thereof. In some embodiments, the first monitoring unit 102 may also include, additionally or alternatively, a camera and/or other sensors, such as an air sampler or gas sensors, which are discussed in more detail below. The first monitoring unit 102 also includes a processor 122 with a first communications unit 124, and includes a memory 126 and a power management unit 128 which may include a battery, and/or a power interface, such as a USB interface. The remote computing unit 104 may have one or more processors 130, one or more memories 132 that stores instructions, and/or a second communications unit 134. In certain embodiments, a cloud or other remote computing infrastructure may be substituted by a local or quasi-local computing infrastructure such as an edge network or a local mesh network.

The first monitoring unit 102 may be considered a local component while the cloud processor may be considered a remote component. "Local" in the context of this application means an area or environment that is being monitored or controlled. For example, the first monitoring unit 102 is typically deployed locally in the environment to be monitored, such as a factory or refinery. "Remote" in the context of this application means in a location outside of the monitored environment, such as a different room, building, city, or country. In some embodiments, computationally intensive processing may be conducted remotely, e.g., not on the local first monitoring unit 102 but instead on remote computing resource 104, such as a cloud computing resource. Doing the computationally intensive processing on the remote computing unit 104 may provide advantages in certain contexts. For example, it may preserve battery life of batteries in the first monitoring unit 102, allow for a relatively simple processor 122 or other computational resources on the first monitoring unit 102, decrease processing time, and/or allow for the use of other data or information that is stored within the remote computing unit 104. In certain embodiments, the processing and/or storage requirements for environmental monitoring are shared between local monitoring unit 102 and remote computing unit 104.

Various criteria and/or heuristics may be employed to divide computation between the local and remote resources. For example, the division can be tuned to balance power consumption (given the size of the device) versus data communication bandwidth. For example computations pertaining to the inversion of particle size data from the sensor response maybe processed locally while corrections to this data may be done remotely using cloud and/or edge resources. Similarly, for an activity detection algorithm, the high resolution data maybe processed locally and some aggregated data transmitted to the cloud or other remote location to determine activity. For noise monitoring, noise waveforms captured locally may be processed locally and only aggregated noise exposure (dBA) values transmitted to the cloud or other remote location. Activation of alarms may be triggered by local computation that compares locally generated measurements against thresholds that have previously been set remotely or fed into the device. If the device is disconnected, the device may still perform all the local notification functions, as needed.

The communication between local devices and remote units may be two-way. For instance, data generated by the sensors 108-120 (e.g., air quality data, temperature data, motion data, etc.) may be stored in the memory 126 on the first monitoring unit 102 and/or may be transmitted to the remote computing resource 104 as indicated by two-way arrow 106. Additionally, other sensor and first monitoring unit data and information may be transmitted to the remote computing unit 104, including sensor health, sensor operating parameters (e.g., measurement periods, sampling rates, power of a laser in the air quality sensor 108, etc.), battery parameters/health, position data and software version. The remote computing unit 104 may also transmit data and instructions to the first monitoring unit 102, such as sensor software or firmware updates, changes to sensor operating parameters, and alarms, for instance. The two-way arrows on the first monitoring unit 102 further illustrate the two-way data transmission between components of the first monitoring unit 102.

Various communication protocols and mechanisms for delivering information between the local monitoring units, e.g., between wearable and stationary monitoring units, and/or between the local monitoring units and remote units, e.g., the remote computing unit 104, may be used. In some instances short-range wireless communications may be used between a local monitoring unit and a local network unit such as a WiFi modem or other transceiver which may include, WiFi (802.11b/g/n 2.4 GHz/5 GHz), LiFi, Bluetooth (e.g., Bluetooth low energy, enhanced data rate), and near-field communications. In some instances, the local network unit may use a wireless or wired link to the internet. In some examples, communication between the local monitoring units and between the cloud computing unit and the local monitoring units may use low power, long range wireless IoT communication protocols such as LoRaWAN LPWAN (narrowband IoT (NB-IoT)), and Cat M1 (LTE Cat M1). Additionally, communication between the local monitoring units and between the cloud computing unit and the local monitoring units may use conventional cellular communications protocols such as 3G, 4G, and 5G. Similarly, the system may have hardware and/or software supporting global positioning satellite ("GPS") or other location determining protocol (e.g., by WiFi or any other signal triangulation determined from access points).

For instance, the first communications unit 124 on the first monitoring unit 102 may have cellular communications hardware for receiving and transmitting data over a cellular protocol. The first communications unit 124 may also have a GPS antenna that can establish a connection with multiple GPS satellites. Using data from communications with such satellites, the first communications unit 124 can determine the location of the first monitoring unit 102. The term "GPS" herein may mean the broader concept of a location system employing one or more satellites that transmit ephemeris (e.g., a table or data file that gives the calculated positions of a satellite at regular intervals throughout a period) and/or position fixing data to a GPS receiver or antenna on a device. The location of the monitoring unit may be calculated from the position fixing data on the unit itself—first communications unit 124 in this case. Multiple satellites may be used in the system with each one communicating ephemeris data and/or position fixing data. The same satellite may communicate both ephemeris data and position fixing data, or ephemeris data and position fixing data may be communicated through separate satellites. The satellites may be satellites in a GPS system, or it may be satellites in another satellite system such as the Russian Global Navigation Satellite System, the European Union Compass system, the Indian Regional Navigational Satellite System, or the Chinese Compass navigation system.

Some GPS systems use a very slow data transfer speed of 50 bits per second, which means that a GPS receiver, in some cases, has to be on for as long as 12 minutes before a GPS positional fix may be obtained. Once a positional fix is obtained, subsequent positional fixes may take much less time to obtain (assuming that the subsequent positional fix occurs within a sufficiently close interval), but this initial lock-on period requires that the GPS receiver be powered for the entire initial lock-on, which can be taxing on devices with small battery capacities.

As stated above, the remote computing unit 104 may have one or more processors 130, one or more memories 132 that stores instructions, and/or a second communications unit 134 that are all communicatively connected, e.g., wirelessly or hard-wired, to each other. In some instances, one or more servers may include the one or more processors 130, the one or more memories 132, and/or the second communications unit 134. Therefore, the term "server" is not limited to a single hardware device, but rather include any hardware and software configured to provide the described functionality. The second communications unit 134 may use any of the communications protocols described above for transmitting and receiving data from the local monitoring devices and any other device.

The one or more memories 132 may be any combination of one or more memory devices, short term, and/or long term memory. Aspects of the disclosure described below may be implemented by various types of hardware, software, firmware, etc. For example, some features of the disclosure may be implemented, at least in part, by non-transitory, machine-readable media that include program instructions, state information, etc., for performing various operations described herein. Examples of program instructions include both machine code, such as produced by a compiler, and files containing higher-level code that may be executed by the computer using an interpreter. Examples of non-transitory, machine-readable media include, but are not limited to, magnetic media such as hard disks with rotating media, floppy disks, and/or magnetic tape; optical media such as CD-ROM disks, digital versatile disk (DVD); magneto-optical media; semiconductor memory such as flash memory devices, nanosystems (including molecular memory ICs), or any type of media or device suitable for storing instructions and/or data. Hardware elements configured to store and/or perform program instructions may be read-only memory devices ("ROM") and/or random access memory ("RAM"). Similarly, any of these types of memory may be provided locally, such as on local unit 102.

Additionally, a computer program product implementation includes a machine-readable storage medium (media) having instructions stored thereon/in which can be used to program a computer to perform any of the processes of the implementations described herein. Computer code for operating and/or configuring the remote computing unit 104 to communicate with local monitoring units and/or to process data as described herein may be stored on any of the types of physical memory described above. Additionally, the entire program code, or portions thereof, may be transmitted and downloaded from a software source over a transmission medium, e.g., over the Internet, or from another server, or transmitted over any other conventional network connection (e.g., extranet, VPN, LAN, etc.) using any communication medium and protocols (e.g., TCP/IP, HTTP, HTTPS, MATT, Ethernet, etc.). It will also be appreciated that computer code for implementing implementations can be implemented in any programming language that can be executed on a client system and/or server or server system such as, for example, C, C++, Python, nodeJS, HTML, any other markup language, Java™, JavaScript®, ActiveX®, any other scripting language, such as VBScript, and/or many other programming languages as are well known may be used. (Java™ is a trademark of Sun Microsystems®, Inc.).

The one or more memories 132 of the remote computing unit 104 may include one or more databases for storing data. The databases can be implemented as single databases, a distributed database, a collection of distributed databases, a database with redundant online or offline backups or other redundancies, etc., and might include a distributed database or storage network and associated processing intelligence. In some embodiments, the cloud computing unit 104 may be able to access the databases of a data provider that provides or allows access to data collected or stored by that data provider, such as weather data from weather.com©.

In certain embodiments, the remote computing unit 104 may be configured with a high level of security. For instance, the United States Federal Risk Authorization Management Program (FedRAMP) may provide a standardized approach to assessment, authorization, security, and continuous monitoring for cloud products and services. This may include the National Institute of Standards and Technology (NIST) SP 800-53 security controls. The remote computing unit 104 may utilize processes and procedures that are FedRAMP compliant. In some embodiments, other protocols may be used for storage, security, and/or validation, including data stored across multiple computers or servers that are linked in a peer-to-peer network, such as blockchain or IOTA.

Figure 2:
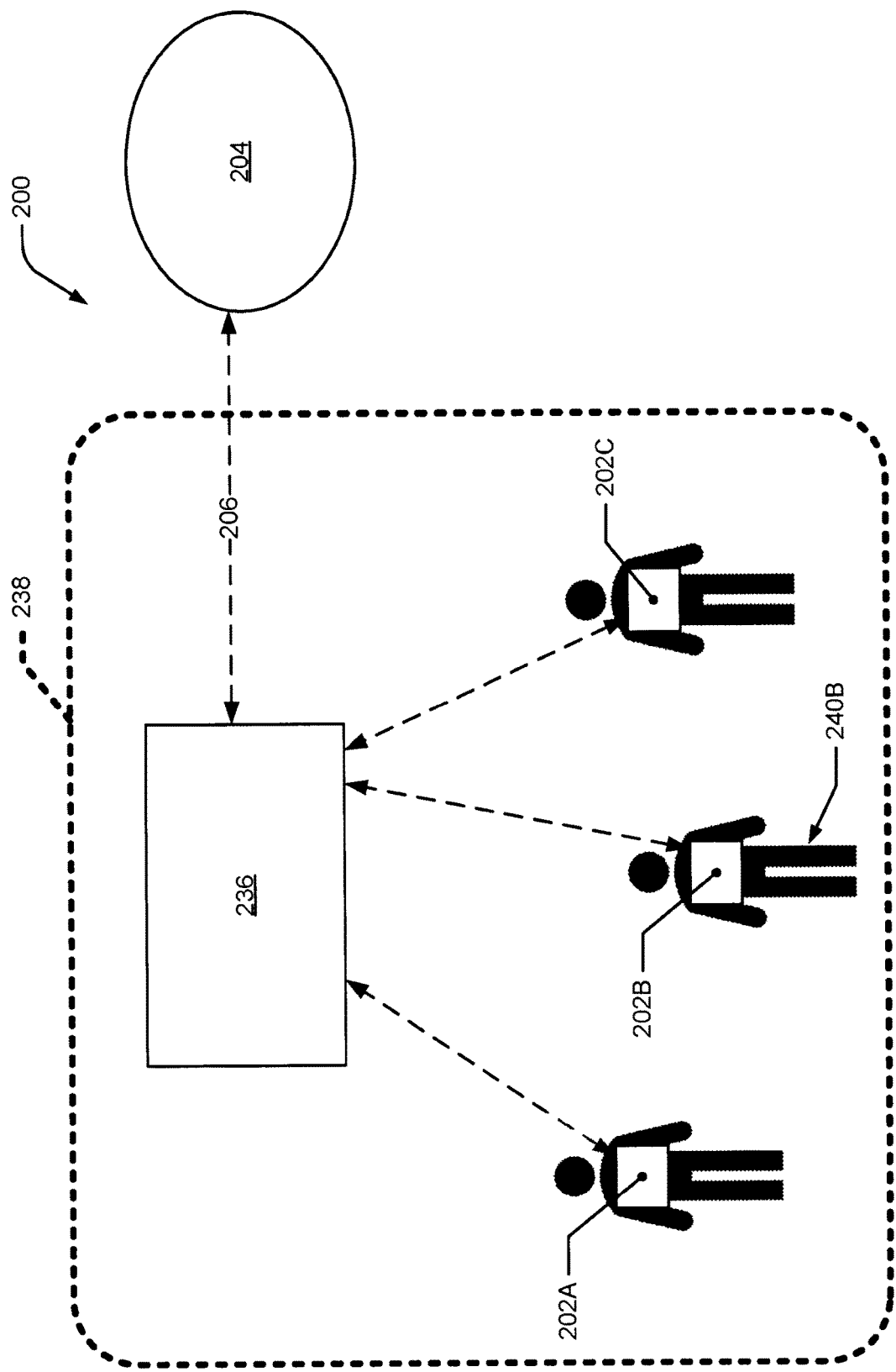
FIG. 2 depicts a second example system for monitoring environmental conditions.

Multiple local monitoring units may be interconnected in various ways. For example, one or more local mobile monitoring units may be directly communicatively connected with a local stationary unit that is directly communicatively connected with a remote computing unit. FIG. 2 depicts a second example system for monitoring environmental conditions. As can be seen, the second example system 200 includes three local mobile monitoring units 202A, 202B, and 202C, a stationary unit 236, and remote computing unit 204. The environment that is to be monitored is represented by the bold dotted line 238; in some embodiments, the area within this environment 238 may be considered the local area. Each mobile monitoring unit 202A-202C may be configured like mobile monitoring unit 102 such that they each include one or more sensors that generate data regarding measured and detected conditions, for example air quality, temperature, humidity, and/or pressure. Each mobile monitoring unit 202A-202C is also mobile and at least two are wearable by individuals, one of which is labeled 240B, in that person's breathing zone. Data may be transmitted between each mobile monitoring unit 202A, 202B, and 202C, and the stationary unit 236 as indicated by the dashed double-sided arrows.

The stationary unit 236 is positioned within the environment 238 in a fixed location relative to mobile monitoring units 202A-202C. The stationary unit also includes a communications unit (not depicted) such as those described above that enable it to transmit and receive data with each mobile monitoring units 202A-202C, and to transmit and receive data to and from the cloud computing unit 204 as indicated by double sided arrow 206. In some instances, the stationary unit 236 may be hard-wired to power and communications interfaces(s), such as DSL, Ethernet, and fiber-optic. The stationary unit 236 may therefore serve, in some embodiments, as a communications hub which presents multiple advantages. For example, depending on the configuration of the mobile monitoring units and the environment, the mobile units may not be able to connect directly with the cloud computing unit. For instance, the local monitoring mobile units may not have the communications protocol necessary to communicate directly over the Internet to the cloud computing unit (e.g., they may only have local WiFi communications protocol). In some instances, even if the mobile monitoring units do have the ability to communicate over the Internet (e.g., by having cellular capability), the mobile monitoring units may not have adequate reception to reach the Internet or other network. In such instances, it may be desirable to have a local stationary unit that has a wired or more powerful wireless connection that can communicate directly over the Internet or other network to the remote computing unit.

In some implementations, the stationary unit 236 may be a monitoring unit like monitoring unit 102 described above such that it contains one or more sensors to detect or measure a condition in the environment 238. In some other embodiments, the stationary unit 236 may be placed outside the environment 238 that is to be monitored, unlike depicted in FIG. 2.

Figure 3:
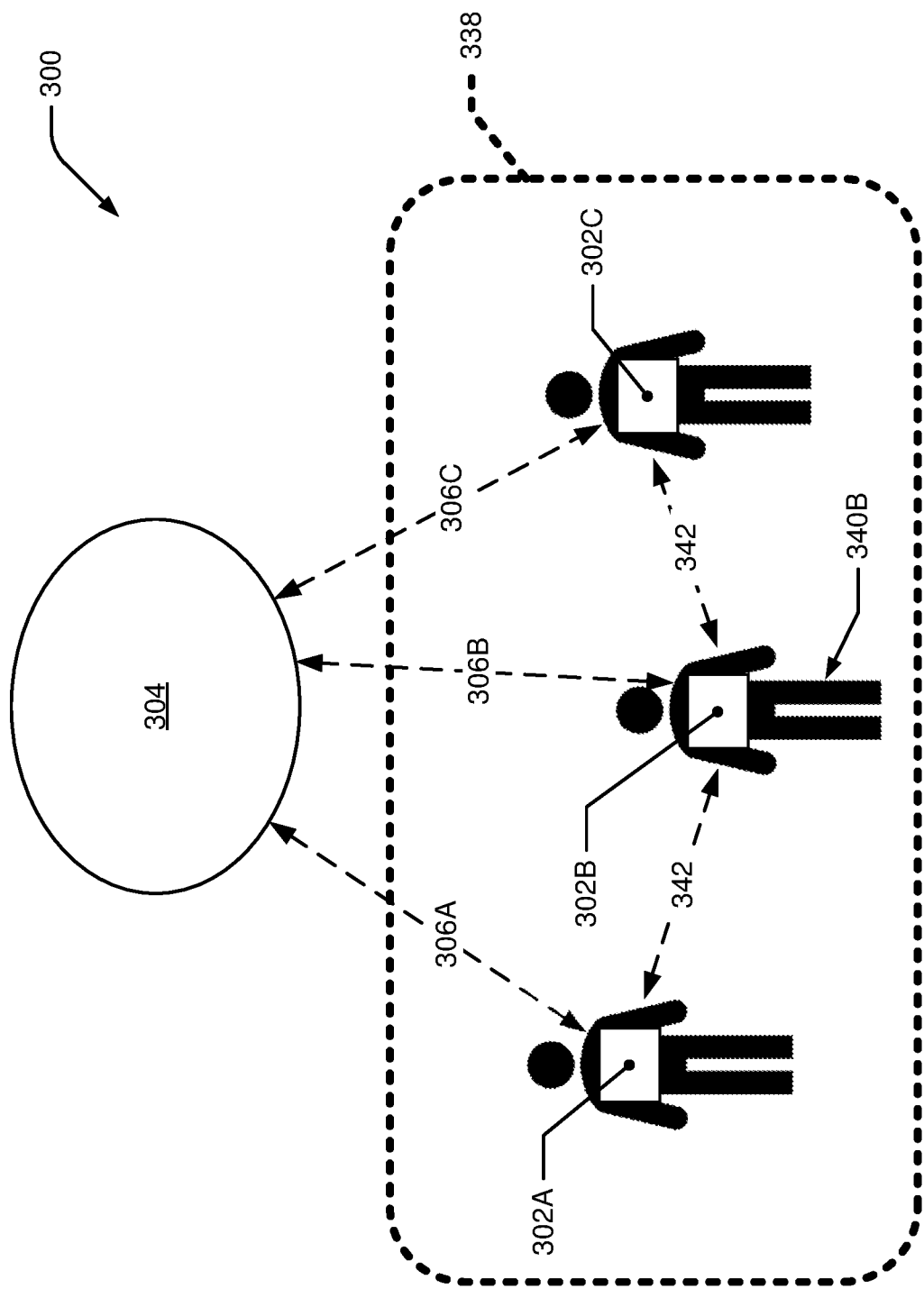
FIG. 3 depicts a third example system for monitoring environmental conditions.

In another network example, one or more local mobile monitoring units may be directly communicatively connected with the cloud computing unit as seen in FIG. 3 which depicts a third example system for monitoring environmental conditions. The third example system 300 includes three local mobile monitoring units 302A, 302B, and 302C and remote computing unit 304. The environment that is to be monitored is represented by the dotted line 338 in which the local mobile monitoring units 302A, 302B, and 302C are positioned. As with example system 200, each mobile monitoring unit 302A-302C may be configured like mobile monitoring unit 102 and each is mobile and at least two are wearable by individuals, one of which is labeled 340B, in that person's breathing zone. Similar to FIG. 1, data may be wirelessly transmitted directly between each mobile monitoring unit 302A, 302B, and 302C, and the cloud computing unit 304 as indicated by the dashed double-sided arrows labeled 306A-306C, respectively. This wireless communication includes any of the examples described above.

In some embodiments, as further depicted in FIG. 3, the mobile monitoring units 302A-302C may be wirelessly connected to each other, as indicated by double sided arrows 342. This enables data to be transmitted and received between each of the mobile monitoring units 302A-302C. This wireless communication protocols may again include any of the examples described above. In certain embodiments, three or more of the mobile monitoring units collectively communicate to form a dynamic network such as a mesh network.

Monitoring Units

Additional details of the monitoring units will now be presented. The monitoring units provided herein may be configured and implemented in various manners and are not limited to the combinations provided herein. For instance, a monitoring unit may include one or more of any of the sensors describe herein and may not, in some implementations, have an air quality sensor. Additionally, any monitoring unit may be implemented as a system; this may include, for example, at least some of its elements being positioned separate from a case or housing, but still communicatively connected, wirelessly or wired, to a controller of the system; such wireless communications may be implemented by the communications interfaces described herein. Some monitoring units, such as the first monitoring unit 102 of FIG. 1, may include a case that encompasses the components of the monitoring unit. FIGS. 4A and 4B depict plan and off-angle views of an example mobile monitoring unit. In FIG. 4A, the mobile monitoring unit 402 includes a case 444 that encompasses the unit's internal components, such as those described herein, a display for a user interface such as a graphical user interface (GUI) 446, an inlet 448, and/or an outlet 450. In FIG. 4B, the mobile monitoring unit 402 also includes a power interface 452, such as a USB interface, where a power cord may be connected to the mobile monitoring unit 402 to charge its battery, as well as inputs 454A, 454B, and 454C, that may be buttons and that provide, when actuated, an input to a component of the mobile monitoring unit 402 such as the processor 422 or a sensor. For example, input 454A may be a reset button that causes the mobile monitoring unit 402 to restart, input 454B may be a power button that causes the mobile monitoring unit 402 to turn on and off, and input 454B may be a configuration button that causes the mobile monitoring unit 402 to be programmed or configured. In some embodiments, the power interface 452 may also be a port configured to transfer data, which includes a cable port, such as the USB port. In some instances, the power interface 452 may be configured to charge wirelessly or charge through a docking station.

The case 444 may have various shapes, such as generally rectangular as depicted in FIG. 4A, as well as circular, oval, or any other shape. The size of the case 444, and thus the size of the mobile monitoring unit 402, may be less than three inches in each measurement dimension, and less than two inches in some embodiments. The size may also be small enough to fit into the palm of a user's hand. In some instances, the dimensions may be 3.0 in×2.75 in×1.25 in (L×W×H).

The case 444 may also include attachment features that enable the mobile monitoring unit 402 to be worn by and affixed to a user. These features may include a clip, clamp, chain, band, lanyard, wristband, buckle, slots to receive a strap, straps, ties, and the like. As stated above, these features enable the mobile monitoring unit 402 to be worn in the wearer's breathing zone. FIG. 4C depicts the example mobile monitoring unit 402 positioned within a wearer's breathing zone 456 which, as stated above, may be considered a hemisphere that extends in front of the wearer's face and that has a radius 458 of approximately 15 to 30 centimeters (or approximately 6 to 11 inches) measured from the midpoint of a line joining the wearer's ears, which is around the wearer's nose and mouth. In certain embodiments, the wearable unit is relatively small, e.g., no dimension is greater than about 2 inches (5 cm) or about 3 inches (8 cm).

As stated above, the monitoring unit 102 includes one or more sensors configured to detect, determine, and/or monitor one or more environmental conditions or metrics. To enable at least some of this detection for some implementations, the inlet 448 and the outlet 450 of the case 444 allow air, pressure, liquid, and other environmental elements to reach the one or more sensors. One of the environmental conditions detected by the monitoring unit 102 in some embodiments is particles in the air. The air quality sensor of some such monitoring units 102 (and/or the mobile monitoring unit 402) may be configured to detect and measure various parameters of particles in the air surrounding the monitoring unit 102. The air quality sensor 108 may be a counter sensor that has a laser which emits a beam through which particles pass and that measures and/or counts the beam pulses to determine particle counts and sizes.

Figure 5:
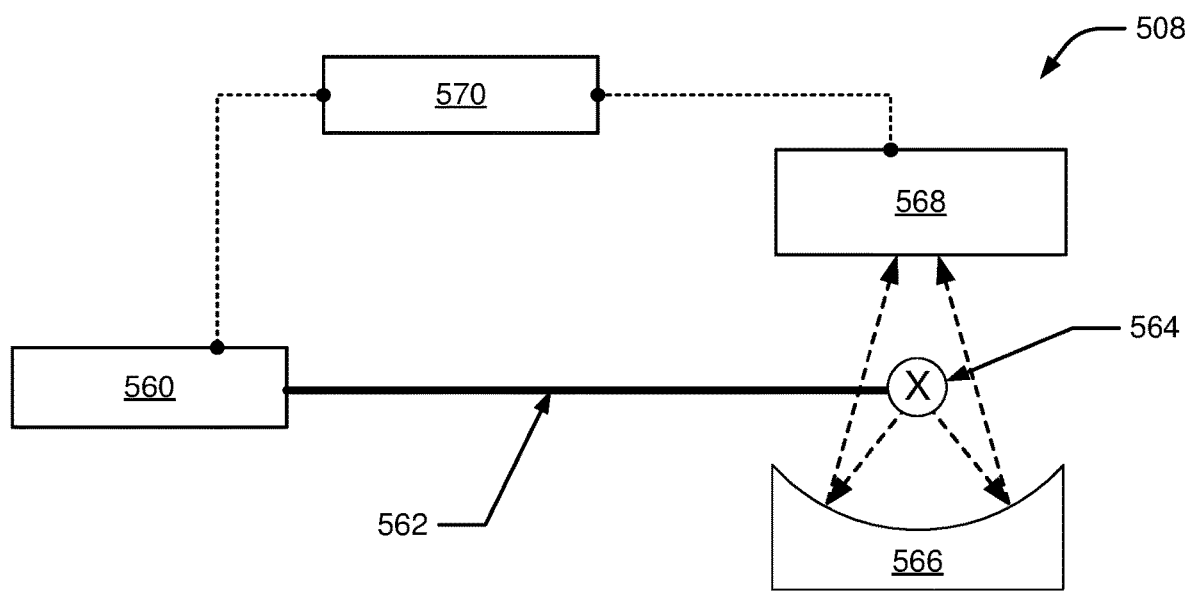
FIG. 5 depicts a schematic of an example air quality sensor.

FIG. 5 presents a schematic of an example optical air quality sensor. This sensor 508 may be used as air quality sensor 108 of FIG. 1, which may be included on the mobile monitoring unit 402. Here, the air quality sensor 508 includes a light source 560 such as a laser that emits a light beam 562 and is configured to allow particles (a single particle 564 is illustrated) to pass through the beam 562. Sensor 508 optionally includes a mirror 566 and a detector 568. The laser may be a diode laser source. In some embodiments, the air quality sensor 508 has a fan or pump to push or pull air into the air quality sensor 508, through the inlet 448, which, in some embodiments, directs particles to pass through the laser beam 562. In FIG. 5, the particles are shown travelling through the air quality sensor 508 in a direction perpendicular to the beam 562 and to the plane of the page, as indicated by the "X" in the particle 564. As the particle 564 passes through the beam 562, the particle 564 interacts with the beam 562 to cause light to scatter off the particle, onto the concave mirror 566, and into the detector 568 which is configured to detect and capture this optical signal as a measurable pulse.

The air quality sensor 508 generates signals responsive to the particles that pass through the beam 562. In some embodiments, the raw signals generated by the air quality sensor 508 include the number of pulses and the sizes of the pulses measured by the detector 568. The air quality sensor 508 may also include logic 570 (e.g., a processor and instructions) that is configured to interpret the measured pulses and generate additional data, such as particle count and particle size. For particle count, these measured pulses over a time period provide a frequency which may correlate to a particle count. Additionally, each pulse may correlate to a single particle and the total number of measured pulses can be correlated to the total number of particles that passed through the air quality sensor 508. Also, the measured pulse height may correlate with the particle size. In some implementations, the particle volume, and by implication the particle's mass, influences pulse height. The data generated about particle mass may not be the exact size, but rather may be categorized into one or more size "bins" which indicate that that mass of each particle falls within a specific size range. For example, the air quality sensor 508 may generate particle mass data for particle mass (PM) 0.3, PM0.5, PM1.0, PM2.5, PM4.0, PM5.0, and PM10, respirable mass concentration, and/or inhalable mass concentration. The respirable mass fraction may be defined in terms of the respirable particles that can reach the alveolar region of the lung; this may include a median value of a distribution of particle sizes of about 4.25 μm with a geometric standard deviation (GSD) of about 1.5; in some instances, about 50% of the particles with an aerodynamic diameter of about 4 μm will be in the respirable fraction. The inhalable mass concentration may be defined as the mass fraction of particles which can be inhaled by nose or mouth; this may include particles with an aerodynamic diameter less about 100 μm. In some examples, the air quality sensor 508 may detect particles that fall under each size bin, e.g., particles less than PM0.3 or less than PM2.5, and not the particle masses within the size bin. This generated data may also include the particle count for each size bin.

In some embodiments, the operating parameters of the air quality sensor 508 may be changed, including the laser power and the pulse height threshold. These adjustments may result in different detected bin sizes and frequency period. For example, decreasing the power of the laser may decrease the detectable size bins or a calibration coefficient of the sensor. Further, changing the air flow to the sensor may change the accuracy and operating range of the device. In certain embodiments, an additional dynamic flow system is incorporated to provide real-time dilution to increase the maximum concentration detectable by the unit. So if concentration is too high, the dilution system may mix sample air with filtered air to reduce the concentration of particles that are then measured by the sensor. An appropriately configured processor may invert the concentration based on the dilution factor to the original undiluted concentration.

In certain embodiments, a monitoring unit includes one or more duplicate sensors for, e.g., calibrating and determining inaccuracies and drift of one of the sensors. In some cases, a duplicate sensor is provided on a fixed monitoring unit. A comparison of simultaneous measurements by two sensors may indicate whether one of the sensors (e.g., one on a wearable unit) has drifted or is inaccurate if these simultaneous measurements are different from each other by a particular threshold. Similarly, during calibration, if these simultaneous measurements are within the particular threshold, then they may be properly calibrated and accurate. For example, it has been discovered that during operation of the air quality sensor 508, particles can deposit on and around the detector 568, mirror 566, and other aspects of the air quality sensor 508 which can cause inaccuracies in the sensor's measurements. The longer the air quality sensor 508 operates, the more particles that deposit within the sensor. In some implementations, referring back to FIG. 1, the monitoring unit 102 may have two duplicate air quality sensors 108. The first of these air quality sensors may be used for regular and continuous monitoring while the second air quality sensor may only be used periodically to provide a simultaneous duplicate measurement that can be compared to the measurements of the first air quality sensor.

The instructions stored on the one or more memories 126, or in the remote computing unit 104, may cause the processor 122 to take simultaneous measurements from two duplicate sensors, such as the two air quality sensors 108, for a particular time period and the measurements generated by these two sensors may be compared against each other to determine whether they differ more than a threshold which may indicate that the first sensor has become inaccurate or drifted. In some instances, the detected inaccuracy or drift of the first sensor may be used as a correction factor to adjust the measurements of the first sensor. For example, if it is determined that the first sensor is off by 5%, then a 5% correction factor can be applied to its subsequent measurements.

In some embodiments, in addition or alternatively to one or more air quality sensors, the first monitoring unit 102 may include one or more non-particle sensors, such as those stated above. This may include the temperature sensor 110 for determining a temperature around the unit and which may be a thermocouple, resistance temperature detector, negative temperature coefficient thermistor, for example; the pressure sensor 112 for determining the pressure around the unit and which may be a pressure transducer, a pressure transmitter, a pressure sender, a pressure indicator, a piezometer, and a manometer; and/or the relative humidity sensor 114 for determining the humidity around the unit and which may be capacitive, resistive, and thermally conductive sensor. As discussed in more detail below, the data from these sensors may be used to correct and adjust the data generated by other sensors. For example, the detected particle count may be affected by, or dependent upon, temperature, relative humidity, and/or pressure, and the instructions stored on the one or more memories 126, or in the cloud computing unit 104, may cause the processor 122 or the one or more processors 130 in the cloud computing unit 104 to adjust, based on one or more of the temperature, relative humidity, and pressure, the detected particle count to a determined particle count.

Other sensors of the monitoring unit, like discussed above, may include an accelerometer 116, such as a triaxial, a bulk micromachined capacitive, electromechanical, and the like; a gyroscope 118 such as a rate and rate-integrating; and/or an acoustic sensor 120 such as a microphone which may be a dynamic, condenser, piezoelectric, carbon, or ribbon.

The instructions stored on the one or more memories 126, or in the remote computing unit 104, may cause the processor 122 to operate any one of the sensors on the first monitoring unit 102, to store the data generated by each of the sensors on the one or more memories 126 on the unit, and to transmit the data generated by each of the sensors to another unit, such as another mobile monitoring unit, the stationary unit, and/or the cloud computing unit 104. In some of the embodiments that include the display 446, the instructions may also cause at least some data generated by the sensors to be displayed on the display, such as particle count, temperature, and/or relative humidity, for example. Instructions stored in the cloud computing unit 104 may also cause the processor to change the operating parameters of any one of the sensors, such as the sample rate of the temperature sensor 110.

The display 446 may be configured to display information to a person, such as a wearer of a mobile monitoring unit. In some implementations, the display 446 may be a liquid crystal display (LCD) or a light emitting diode (LED) display (e.g., an OLED display); the display 446 may also be black and white, or color. In some embodiments, displays may show sensor reading values (e.g. PM concentration), risk factors, temperature/humidity data, visual indicators of risk (e.g. red for dangerous levels of high concentration, green for safe levels), and real time TWA analysis.

In some embodiments, the first monitoring unit 102 may also include a camera that may face out from the case of the monitoring unit for capturing imaging data such as photographs, video, or both. Referring back to FIG. 4, the monitoring unit 402 includes a camera 472 that faces out from the case 444; FIG. 1 also includes the camera 172. In certain embodiments, a camera may have a rotatable angle of view; for example, a camera may be mounted on a hinged or similar part. Like the sensors, the camera 172 is communicatively connected to the processor 122. Some example cameras include omnivision image sensors with appropriate lenses, such as wide angle lens, which may be used to image a large area. The instructions stored on the one or more memories 126, or in the remote computing unit 104, may cause the processor 122 to operate the camera 172 to record video and/or photographs, store them on the one or more memory 126, and to transmit the video and/or photographs to the remote computing unit 104. Instructions stored in the cloud computing unit 104 may also cause the processor to change the operating parameters of the camera 172, such as its operating mode to capture video or photographs, as well as the rate at which videos and photographs are taken, such as photographs every 10 seconds, every 30 seconds, and video at different framerates, such as 24 frames per second (fps), 30 fps, 60 fps, 120 fps, 240 fps, and 300 fps.

In some implementations, a camera's operation is tied to local sensor outputs. In certain embodiments, the camera only record images/video when the sensor parameters, as interpreted by camera control logic, trigger the camera to record. One application of a camera is to diagnose an issue or condition that may have caused a detected increase in particulate matter or noise. The camera control logic may control camera operation in a way that gathers only relevant images/videos (e.g., when sensor readings indicate a need for additional information about the local environment or the activities currently being conducted).

As noted above, the first monitoring unit 102, including the communications unit 124, may have a location or positioning sensor, such as a GPS antenna that may determine the position of the first monitoring unit 102. This GPS antenna may be integrated with a processing chip that includes the processor 122 and the memory 126. The location of the monitoring unit may also be obtained using other means, such as with Bluetooth or Wi-Fi communications.

In some embodiments, the first monitoring unit 102 may include a notification mechanism that is configured to present to a person with a notification, such as an alarm or alert. For stationary monitoring units, this may include presenting persons within a particular spatial proximity from the stationary monitoring unit with the notification; for mobile monitoring units such as wearable monitoring units, this may include presenting the wearer of the monitoring unit with the notification.

The "notification" may be one or more of an alarm, alert, message, an auditory output, an electronic communication, an electromagnetic communication, a visual output, and a tactile output. Notifications may be provided through a variety of media, and may, in some cases, require further action by an intermediate device before being perceptible by the person. For example, the monitoring unit may have a notification mechanism that includes a display or lights that are configured to display graphics or light up in order to catch the attention of a person (the notification, in this case, may refer to a signal that is sent to the lights or display that cause these components to light up or display graphics to a person; it may also refer to the light or graphics that is emitted or displayed by components receiving the signal in response to the signal). In FIG. 1, the notification mechanism 174 is represented by circle 174. In some examples, the monitoring unit may have a notification mechanism that includes a speaker or other device capable of generating auditory output that may be used to provide the notification (the notification in this case may be a signal that is sent to a speaker or other audio device; it may also refer to the actual audio output that is generated by the audio device in response to the signal).

In some other or additional examples, the notification mechanism may include a wireless interface and the notification may take the form of an electronic or electromagnetic communication, e.g., a wireless signal, that is sent to another device, e.g., a monitoring unit or a smartphone, associated with the person (the notification in this case may be an electromagnetic signal; it may also refer to any audio, visual, tactile, or other output generated by the receiving device in response to receipt of the signal). In such scenarios, the notification may still be generated or initiated by the notification mechanism even if the intended recipient device of the communication fails to be activated or otherwise fails to convey the notification to the person. The notification mechanism may be configured to generate and/or provide one or more notifications to the user, and may include one or more components that may be used to generate audio, visual, tactile, electromagnetic, or other types of notifications.

As stated above, the power management unit 128 seen in FIG. 1 may include a battery. In some implementations, the battery may be rechargeable, such as a lithium-ion, nickel cadmium, or nickel metal hydride for instance. The battery is configured to provide a reasonable discharge time under normal operation, such as about 4 hours, 8 hours, 10 hours, and 12 hours. The battery may also be configured to provide information regarding the state of the charge (SOC) and state of health (SOH) of the battery. This information may include charge acceptance, internal resistance, voltage, and self-discharge. The battery of the power management unit 128 is used to power any feature of the monitoring unit 102, such as the processor 122, the notification mechanism 174, the communications unit 124, and any one of the sensors. In some embodiments, one or more of the sensors on the monitoring unit 102 may be "active" such that it requires an external source of power to operate. The air quality sensor 108 described above, including sensor 508 in FIG. 5, may be an active sensor because it may use a pump or fan to push or pull air into and through a chamber of the sensor. One or more of the sensors on the monitoring unit 102 may be passive in that it detects and responds to an input from the physical environment, such as detecting vibrations, light, heat, and radiation, for instance. For example, the temperature sensor 110, the pressure sensor 112, and the relative humidity sensor 114 may be passive sensors.

In some embodiments, the monitoring unit 102 may include a filter sample cartridge and pump, represented as item 176 in FIG. 1. The pump is configured to push or pull air into the filter sample cartridge which collects the particulates and elements in the air. The filter sample may be removed from the monitoring unit 102 and analyzed offline, such as in a laboratory or remote location. The analysis results may be entered as data into the cloud computing unit 104 or to the monitoring device 102 and used to calibrate, adjust, and/or correlate data generated by the monitoring unit. For example, the air quality sensor 108 and the filter sample cartridge and pump may be simultaneously operated, and the particle count and size data detected and/or generated by air quality sensor 108 can be compared to the size, particle count, and other particle information measured by and determined from filter sample cartridge results. This correlation may be used in subsequent monitoring when a monitoring unit is working in the same environment. For instance, the correlation may indicate that the particle count data generated by the air quality sensor 108 is offset from the actual particle count of the air by a first correction factor and this first correction factor can be applied to future data generated by the air quality sensor 108 so that the detected results align with the results measured by filter sample cartridge. In another instance, filter sample results may indicate the type or types of particles that were detected, such as silica or lead, and these known particles can be correlated with the detected particles and other data generated by the monitoring unit.

The operation of the filter sample cartridge and pump, such as the flow rates and operation times, may vary and may be configured to provide comparative sensor data. For example, the filter sample cartridge and pump may be caused to operate, by the processor executing instructions in the memory or the cloud computing unit, and collect air samples while the air quality sensor 108 is also operating. In some embodiments, the filter sample cartridge and pump are integrated into a mobile monitoring unit and a stationary monitoring unit. In some other embodiments, the filter sample cartridge and pump may be separate from any monitoring unit, but may be positioned in close proximity to the monitoring unit in order to sample air and provide correlation data like described above.

Figure 6:
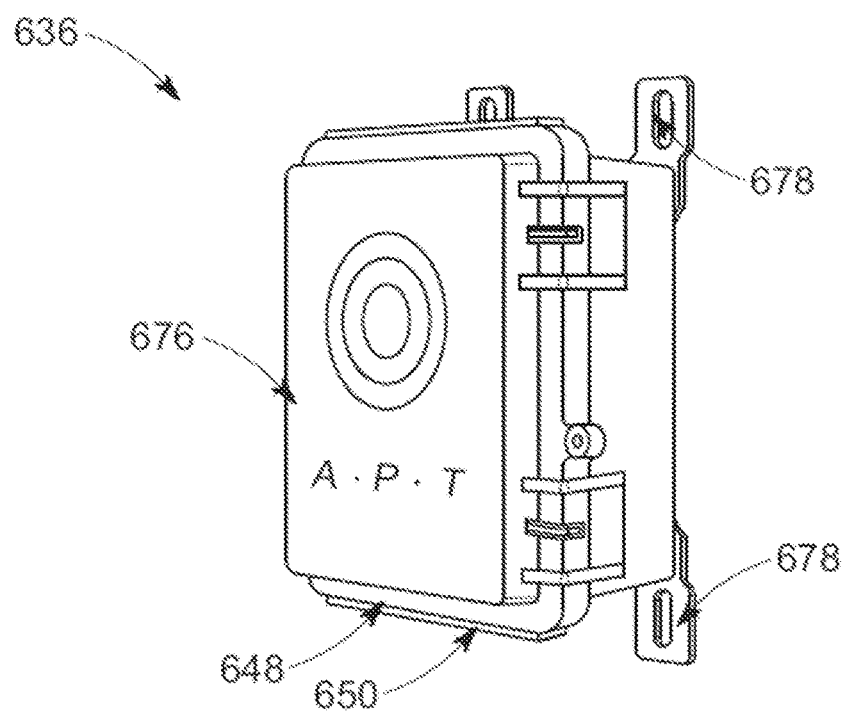
FIG. 6 depicts an example stationary monitoring unit.

As mentioned above, some monitoring units may be considered stationary monitoring units that are non-wearable and fixed in a position. FIG. 6 depicts an example stationary monitoring unit 636 which may be like stationary monitoring unit 236 described above. In some embodiments, the stationary monitoring unit 636 may have the same features as the monitoring unit 102 of FIG. 1, such as the air quality sensor 108, the temperature sensor 110, the pressure sensor 112, the relative humidity sensor 114, the communications unit 124, and/or the power management unit 128. However, the communications unit 124 of the stationary unit 636 may be different than that of the mobile monitoring unit, such as having hard-wired communications interfaces, e.g., for DSL, Ethernet, and fiber-optic connections; it may also have more powerful wireless antennas than a mobile monitoring unit. The power management unit 128 may also be configured to receive hard-wired power, such as from a wall outlet or building electricity, which may be 110 volts or 220 volts, and may be 15 amp and 20 amp circuits.

Some stationary units may also have a different case than mobile monitoring units. As seen in FIG. 6, stationary monitoring unit 636 includes a hinged lid 676 and mounting features 678 for securing the stationary monitoring unit 636 to a fixed location, such as a wall or post. The hinged lid 676 allows for direct access to the unit's components, such as its buttons and the power management unit (which may be a battery or hard-wiring), as well as offering the weather protection for the unit. In some instances, the stationary monitoring unit 636 has an inlet 648 and an outlet 650, like described above, in order to allow the unit's sensors to detect environmental conditions. For additional weather protection, the inlet 648 and outlet 650 may be positioned on the bottom of the unit.

As stated above, some embodiments of the monitoring units may have any combination of the sensors described herein, and the features and aspects of the monitoring unit may be implemented as a system. This may include some embodiments of the monitoring unit not having an air quality sensor. Additionally, this may include some of at least some of the monitoring unit's elements, such as a sensor, being physically separate from a case or housing of the monitoring unit, but still communicatively connected, wirelessly or wired, to a controller of the monitoring unit.

As discussed in more detail below, in some embodiments, the monitoring unit may have one or more acoustic sensors and be configured for detecting noises and/or sources of such noises; in some embodiments the monitoring unit may have a plurality of sensors, such as a temperature sensor, a humidity sensor, a heart rate sensor, an impedance sensor, and/or a light sensor, and/or be configured to determine an estimated heat stress; in some embodiments the monitoring unit may have one or more cameras configured to record still images and/or videos, and/or be configured to detect activities in an environment. In some embodiments, one or more of the monitoring unit's sensors may be used to make direct determinations of the metrics or conditions detected by the sensors, or the sensors may be used to make determinations related to other metrics or conditions. For example, acoustic signals detected by a monitoring unit's acoustic sensor may be used with the images and/or video recorded by a camera to determine an activity generating the acoustic signals. In another example, a gas detected by a monitoring unit's gas sensor may be used with an air quality sensor to assist with determining the source of an emission.

Example Data Analysis Techniques

The monitoring systems and apparatuses described herein may use various data analysis techniques, which may be implemented as executable processes or algorithms, to measure and/or determine desired metrics. These metrics may provide raw data, signals, or other information. Examples of measured metrics may include particle count, particle size, particle mass, temperature, relative humidity, pressure, acoustic signals, gases detected, concentrations of gases, heart rate, irradiance, motion data, and/or location data, for instance. The determined metrics may be calculated values that include, for example, the types of materials detected (e.g., silica, lead) and metrics that have been adjusted or corrected to account for other variables (e.g., a particle count adjusted to account for the pressure and humidity).

Various computational techniques described herein may use multiple inputs. As mentioned herein, some of these inputs include the raw sensor data generated by the one or more sensors of a monitoring unit. This data can include, for example, a particle count over a time period and particle size (e.g., particle masses within bin sizes PM 0.3, PM0.5, PM PM1.0, PM2.5, PM4.0, PM5.0, and/or PM10), temperature, humidity, pressure, acoustic signals (e.g., generated by an acoustic sensor), inertial signals (e.g., generated by a gyroscope or accelerometer), position data (e.g., GPS position data), and/or camera or video data. In some instances, this data may be raw or converted data. For example, as described above, the air quality sensor 108 may generate a pulse frequency which can be converted to a particle count over time, and may generate a pulse height which can be converted to particle mass size.

In addition to the data sensed by a monitoring unit, the techniques may also use data that was not sensed by the monitoring unit. This can include publicly available data which may be weather feeds and air quality indices, as well as particle compositional information from one or more material safety data sheets (MSDS). MSDSes may include information as to which hazardous materials, and at what percentages, are included in various materials; MSDSes may also indicate the acceptable OSHA exposure levels for the hazardous materials. For example, a MSDS for concrete may indicate that it includes 0-90% silica (by weight) and 15-25% calcium hydroxide (by weight), and may list the OSHA permissible exposure limit (PEL) based on a time-weighted average (discussed below). All of this data may be stored within a memory or database of the remote computing unit 104, or may be accessible by the one or more processors of the remote computing unit 104 such that it can be used by the one or more processors of the remote computing unit 104.

Similarly, computational techniques may use historical data from the same or other monitoring units. For instance, the data generated by one monitoring unit may be transmitted to and stored within the cloud computing unit 104 which can later be used by the cloud computing unit 104 for determinations related to that same monitoring unit. In some other instances, the data generated by one monitoring unit may be transmitted to and stored within the cloud computing unit 104 which can later be used by the cloud computing unit 104 for determinations related to other monitoring units. For example, one monitoring unit may have generated data at a specific location at one time and at a later time, this data may be used for another monitoring unit at that same specific location. Additionally, the data generated by one monitoring unit may be transmitted to other monitoring units that are currently with the same environment, like described above and depicted in FIG. 3.

In some implementations, one or more inputs include data and/or signals captured using sensors and/or an application on a user's phone, mobile device, and wearable electronic device, which may include using that device's sensor data, e.g., accelerometer, gyroscopic, and/or acoustic data, combined with separate monitoring unit (mobile or stationary) readings. In some instances, the techniques may run on the cloud with data aggregated from the phone and/or the monitoring unit.

In some embodiments, inputs to computational techniques may include data related to an activity or task being performed near a monitoring unit. For example, one or more of the sensors on the monitoring device may generate data that is related to or indicative of a particular activity or task. This may include the gyroscope, accelerometer, and/or microphone generated motion data and/or signals that can be associated with various activities or tasks, such as jackhammering, an explosion, and/or a gas release. In some instances, the data may indicate that a wearer of a mobile monitoring unit is performing the task or activity. For example, the gyroscope, accelerometer, and/or microphone may indicate that the wearer is jackhammering. In a similar example, the microphone of one mobile monitoring unit may indicate that the wearer is near, but not performing, the task, like jackhammering. Data from a microphone may further be indicative of particle sources from nearby operating machinery based on characteristic noise signatures of different equipment and/or machinery.

The techniques described herein may also, in some embodiments, use sensor parameters as inputs. This may include sensor health, battery parameters/health, current software version, and operating parameters, e.g., measurement periods, sample rate, and/or power of the laser for the air quality sensor 508.

The apparatuses and techniques of the present disclosure may provide any of various outputs. The content and form of an output variations may depend on the mechanism of presentation, such as via a dashboard, display, GUI, notifications of a notification mechanism, messages sent to user devices (e.g., text messages, email messages, phone calls to a user's phone), and instructions to a facility where the monitoring unit resides (e.g., shut down a machine that might be contributing to a dangerous condition, activate a system such as a ventilation system that can mitigate a dangerous condition, provide announcement to all personnel, etc.). Unless specified, the outputs described herein may be presented in any of these means.

In some embodiments, data characterizing particles may be an output of the apparatuses and techniques. This can include total particle counts, the time period of the total particle counts, particle concentration binned by size, particle mass per bin size, particle refractive index, particle fractal dimensions, chemical composition, particle volume, particle surface area, particle size distribution, particle mass within a known cutoff curve (e.g., PM 2.5, PM 4.0). Additional data from any of the sensors on the monitoring unit may be output, such as non-particle environmental information including temperature, humidity, pressure, gas composition, auditory signals (e.g., decibels). Output data may also include motion data, location data (e.g., GPS coordinates), communications information (e.g., signal strength to a communications node, like a cell tower, WiFi hub, or GPS satellites), battery data (e.g., charge level, lower battery, undergoing charging), and/or sensor data (e.g., whether a sensor is on and whether a sensor has malfunctioned), for example.

Some embodiments may output corrected data that may be considered raw data adjusted by one or more "correction factors." For example, as referenced herein, some detected raw data may be dependent on environmental factors, such as temperature, pressure, relative humidity, gas composition, and/or noise. For example, a given value of a particle count or mass may not raise a flag under normal ambient conditions, but when coupled with an elevated concentration of $CO_2$ or $O_2$ may deserve special attention/action. In other examples, the compositions of particles may be known or estimated, and only one or a few components warrant monitoring. Using the composition information along with measured particle mass, programmed computational techniques may provide levels of one or more potentially problematic components. Some correction factors are further discussed below.

Information relevant to making a decision for health and safety may also be an output in some implementations. This may include whether any exposures exceed safety limits that may be set by, for instance, OSHA or other administration or entity. These exposures may be based on instantaneous peak exposures as well as time-weighted averages. For instance, some exposures may be lower exposure limits (LEL), upper exposure limits (UEL), acute (or airborne) exposure limits (AEL), combustible limits, and short-term exposure limits (STEL), ceiling limits, action level, permissible exposure level (PEL) or any other irregularities in sampled data that can be captured. Additionally, any quantifiable risk factors in comparison to previous historical data, trend analysis, ventilation factors, or other risk factors, depending on the environment, may be output. Such outputs may be based on data that a mobile unit has detected. In some instances, the outputs may be a prediction as to when that exposure limit may be reached in the future. For example, one output may be a notification to the wearer of a mobile monitoring unit that the wearer has not, but is expected to exceed an PEL in an additional X minutes or hours given the current and/or past detected conditions.

In some embodiments, the techniques and apparatuses described herein may output a time-weighted average (TWA) of an exposure, which indicates the average exposure to a material over a fixed time interval, such as an 8-hour workday. Some TWAs may be equal to the sum of the portion of each time period (as a decimal, such as 0.25 hour) multiplied by the levels of the substance or agent during the time period divided by the hours in the workday (e.g., 8 hours or 4 hours). Many safety regulations use TWA units, and these TWAs may provide an estimated exposure over a period of time even though measurements may not have been continuous over that entire period of time. For example, a monitoring unit may generate data for only 6.5 hours during an 8-hour period (which may be caused by a variety of reasons, such as device failure or shutdown for a period, and the monitoring unit moving outside the environment for an amount of time) and an 8-hour TWA can be calculated using the 6.5 hours of generated data. TWAs are discussed further below.

Outputs may include calculated particle information that is outside the detected range(s) provided by an air quality or particle sensor. In some implementations, an air quality sensor may provide particle counts and particle size data only for discrete particle diameters ranges or size bins, and therefore cannot directly or precisely provide data regarding particles that do not correlate directly with these discrete size bins. However, it may be desirable to provide particle count and/or size data for particles that are not directly measured by the sensor's size bins because, for instance, some exposure limits or regulations are in terms of these other particle sizes. The techniques and apparatuses described herein may be able to output calculated particle information, e.g., particle counts and size, for particles that are not within the discrete size bins of the sensors. For example, the air quality sensor may provide particle counts and size data for particles of 1 micron or smaller, 2 microns or smaller, and 5 microns or smaller and therefore cannot directly provide data regarding particles within these size bins, such as particles of 1.5, 3, or 4 microns or smaller. But a safety regulation may specify an exposure limit regarding particles outside these detected size bins (1, 2, and 5 microns), such as 4 microns or smaller. The techniques described herein may use the detected data for the discrete size bins, e.g., of 1, 2, and 5 microns, to determine and output calculated particle information, e.g. particle count, about particles not correlated exactly with these discrete size bins, such as particles of 4 microns or smaller. In certain embodiments, this is achieved by interpolating the data between size bins and/or by fitting the size distribution to a unimodal or multimodal lognormal size distribution.

As mentioned above, the apparatuses and techniques may determine an activity or task likely being performed near a monitoring unit, and output information related to or based on that activity. For example, using data from one or more of an accelerometer, a gyroscope, and/or a microphone (e.g., on a mobile monitoring unit worn by a user), a technique determines the activity that the wearer is engaged in (or that is being performed in the vicinity of the wearer) for an industrial setting. For example, as discussed herein, jackhammering may have a characteristic noise signature (as detected by a microphone on the mobile monitoring unit, a stationary monitoring unit, or both) and a characteristic motion signature. So when appropriate acoustic signals are coupled to the vibration detected from the motion sensors, e.g., the accelerometer and/or the gyroscope, the technique may infer that the person wearing the sensor is using a jackhammer. If, by contrast, the signal is just the noise (no associated motion detected by the inertial sensor), the technique determines that jackhammering is being done in the vicinity of the individual.

By correlating particle exposure to activity of the individual or the activity being carried out in the vicinity, an industrial hygienist or safety officer, or other individual or system can make appropriate safety or policy decisions. As discussed below, the relationship between air quality and activity may be implemented as a pre-trained model such as a machine learning model.

Alerts, alarms, and other notifications may also be outputs by the techniques and apparatuses. As mentioned above, alerts for problematic environmental conditions detected by the techniques may be provided by the notification mechanism in the form of, for example, tactile, auditory, visual, and/or combinations thereof. These alerts may be generated within the monitoring unit itself, at a remote site or monitoring unit (e.g., the cloud computing unit 104), or a combination. An alert may be a generic alarm and may also be a notification for a specific intervention. For example, the specific alert may be that a user should remove himself from the area, turn on engineering control, wear personal protective equipment ("PPE") or take one or more actions. As noted above, the alert may also include a prediction about when one or more applicable exposure limits will occur.

Outputs of the techniques and apparatuses may also include instructions to local mobile and/or stationary monitoring units. These instructions may be related to hazardous or otherwise problematic environmental conditions detected or determined. For example, in response to a mobile monitoring unit detecting an exposure at or above an AEL, instructions may be issued to that mobile monitoring unit to gather additional information, such as to cause the camera to capture images, e.g., still or video, to activate a microphone to capture acoustic signals, or to activate other sensors to gather data, such as the accelerometer and/or gyroscope, which can be used to correlate output from sensors to activities. This gathered information may assist with diagnosing a source of exposure as well as with offering solutions and/or corrective actions regarding exposures. From some industrial hygiene perspectives, goals may by not only to identify if an exposure limit has been exceeded, but also what solutions may prevent that exposure in the future. This gathered information can also be used to identify particular areas and activities of high exposures and/or to warn and offer possible controls at these areas (limiting exposure, engineering controls, etc.).

As discussed in greater detail below, outputs may also include maps that depict detected and/or determined metrics, such as particle concentrations, from monitoring units in an environment. These maps may be snapshots of a single time, or a time-lapse representation of detected and/or determined metrics over time.

Various computational processing operations may be employed to convert input data to appropriate outputs. Examples of such operations include machine learning, application of conversion factors, and/or various other forms of data inversion. Suitable computational logic on the sensing unit and/or a remote computational resource is used to perform these operations.

In certain embodiments, data inversion may be employed in various manners, such as to provide particle information outside the sensed range (e.g., for particles 4 microns or smaller as mentioned above). Some examples of suitable data inversion logic include the method of moments and/or machine learning (e.g., artificial neural networks). Machine learning techniques, for example, may employ a training set including data outside directed measured ranges (e.g., at 4 microns or smaller) along with data at directly measured ranges (e.g., 2.5 microns or smaller) to learn how predict results at desired points outside the directly measured ranges from data at the directly measured ranges.

Computational processing for applying correction factors, as implemented by appropriate logic, may take various forms. For example, a process may take particle count or mass readings for a particular type of particulate and convert it to a reading for a particular type of material that makes up only a fraction of materials in the particles that are directly measured. For example, if a material of interest (e.g., silica or a particular heavy metal such as cadmium) is X % of total particle mass, volume, or count, the computational process converts a direct reading of particle information (count, mass, or volume) to a reading for the material of interest. In some cases, the computational process applies a simple conversion factor. In a specific case, if silica is the compound of concern and it makes up only 15% of the mass of the particulate matter being detected, the sensed particle mass may be multiplied by 0.15 to determine the mass of silica in the sensed particles.

As an example, computational logic may be configured to account for a material of interest being X % of total particle mass, volume, or count. For example, if silica is the compound of concern and it is only 15% of the mass of the particulate matter being detected, the sensed particle mass may be multiplied by 0.15 to determine the mass of silica in the sensed particles. As mentioned, appropriate conversion factors may be obtained by various techniques such as from material safety data sheets for the material under consideration. Alternatively, sample particles may be chemically analyzed. For example, previously collected samples—such as actual air sample sent to a lab—are analyzed to determine chemical composition.

In certain embodiments, the converted particle information is utilized in determining whether to trigger an alarm or other action. For example, an MSDS or other source of compositional data may indicate that a particular type of particle (generated in a particular occupational setting) has only 15% silica or other hazardous particulate content. If occupational requirements specify less than X mass of silica exposure per eight hours (e.g., 50 micrograms per m$^3$), a particle mass of X/0.15 will trigger action.

Correction factors other than those based on particle composition may be employed. Examples include corrections based on local environmental conditions; e.g., temperature, pressure, humidity, and the like. Such local conditions may, in some embodiments, be determined using sensors included in the devices described herein. Such corrections may be appropriate when operating in extreme conditions (e.g., very high temperature and humidity) and/or when the sensors are particularly sensitive changes in local conditions. The corrections may be determined by calibration, machine learning, etc.

In some cases, computational logic uses an expression that is more complicated than a simple coefficient or multiplier applied to measured values. For example, the logic may employ an expression having multiple terms and/or be non-linear. In such cases, corrective factors may be applied to a whole expression used for correction, or just one or a few terms in the expression. For example, based on instantaneous measured conditions (e.g., temperature, humidity, pressure, etc.) computational logic may adjust some coefficients or other parameters in linear or nonlinear way in the expression.

In some implementations, the processing logic is configured to account for sensor drift or other time variations in sensor behavior. Any of the above-referenced sensors, such as particle counters, can become less accurate because of various factors, such as particulates depositing on particle detectors. For some particle counters, it has been found that the level of drift due to deposition may be dependent on size and/or concentration of particles, and it may be non-linear with time; e.g., the impact of particle concentration goes as the power of 2. If a sensor's drift or degradation over time is known, the computational logic may account for this and adjust sensor output measurements accordingly. The result may be implemented as a calibration or a correction.

In some implementations, sensor drift adjustment or calibration is accomplished using two sensors on the unit and one operates only periodically and that measurement is compared to the other sensor. In another approach two sensors are used, with the one being evaluated being on a mobile unit and the other on a fixed unit; the mobile unit passes by the fixed unit and detected data is compared and accounted for. In either approach, if differences in readings from the two units vary over time, the output of the regularly used unit is adjusted to account for the difference. In certain embodiments, the logic is configured to characterize sensor health based on the reading; e.g., replace sensor if the readings are off by X amount.

In certain embodiments, the computational logic is configured to compare data against threshold/alarm conditions that are triggered using various sources of detected data alone or in combination with other known or detected environmental conditions. For example, detected particle information may be used in conjunction with composition data or other data about other environmental conditions in a comparison against threshold/alarm conditions. In certain embodiments, the computational logic compares directly or indirectly measured data against threshold conditions that triggers a further device action at the location of the condition. Examples of such actions include camera activation or modified operation, microphone activation, motion detection, or other local action of the unit or an associated device such as a user's phone.

In certain embodiments, computational logic is configured to generate maps of detected or determined metrics or conditions in an environment, such as air quality in a work area or other location. The logic may be configured to generate such maps using only limited information, from one or more sensors, typically from multiple sensors. Such maps may be generated using an appropriate model such as a statistical model (e.g., produced by Kriging) or machine learning model (such as an artificial neural network). The maps are produced by interpolating detected or determined metrics, such as air quality values (e.g., particle concentrations) or other conditions, in positions between measuring unit locations (fixed and/or mobile). To provide interpolated information from data provided at only a few discrete locations, a model may be trained using data provided at many different locations beyond simply those of installed sensors in the final system. In certain embodiments, a mapping routine may evolve or improve over time by using additional training data acquired by moving wearable sensors providing real time readings of detected or determined metrics, such as particle concentration, at various locations aside from the fixed monitors that might continually detect concentration at fixed locations. In some embodiments, a single model is used for calculating air quality values at all points in the interpolation space (e.g., a work area). In other embodiments, multiple separate models are used for each of multiple interpolation positions.

Figure 7:
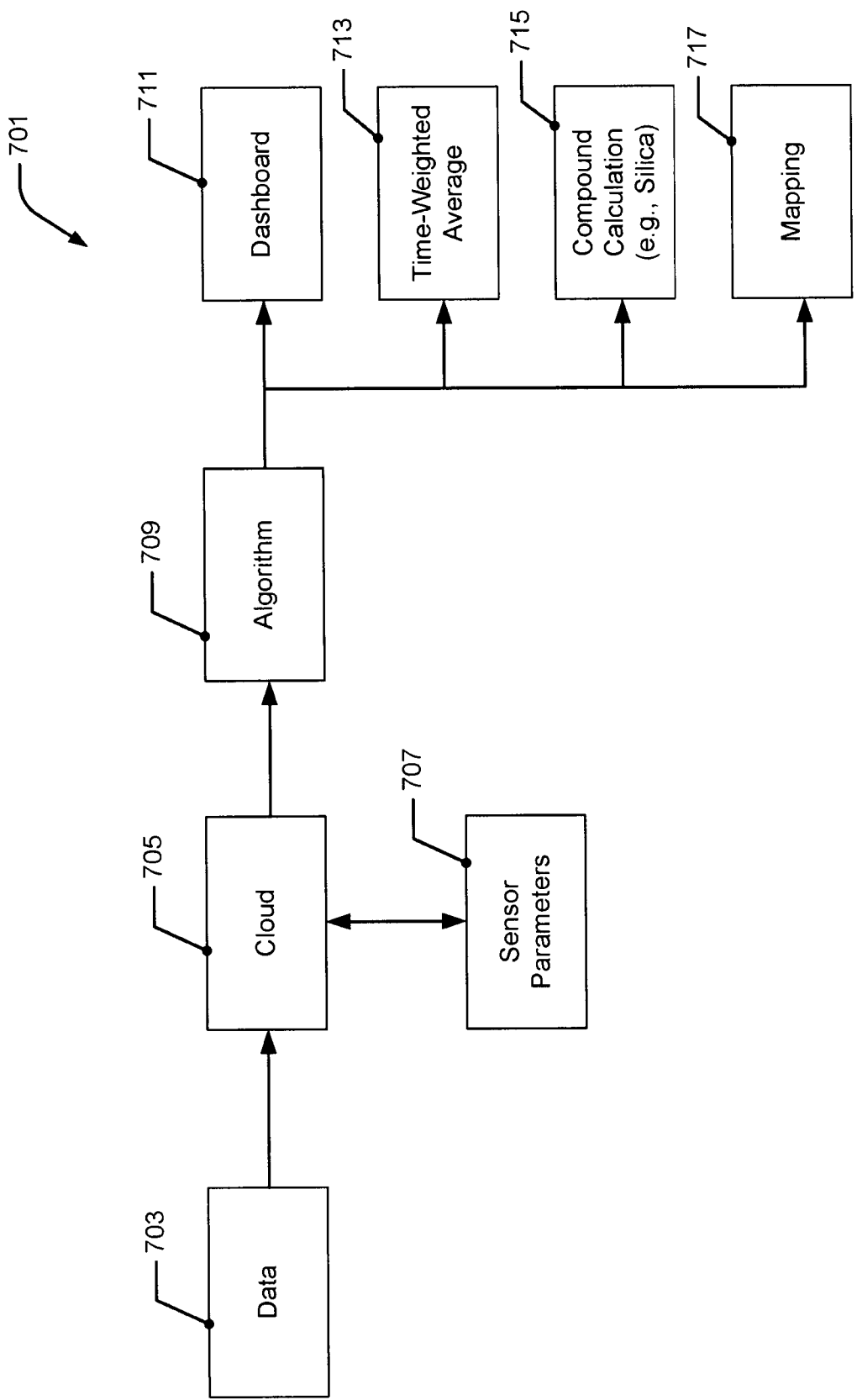
FIG. 7 depicts a computational framework for implementation various analyses as described herein.

FIG. 7 presents an example of an architecture for a system 701 that provides computational resources for one or more monitoring units. In this example, most or all of the relevant computing and/or data storage is provided remotely, e.g. on the cloud as indicated by block 705. Data 703, which includes at least some data from a local monitoring unit, typically including a mobile monitoring unit, is provided to remote processing and/or storage resources such as cloud 705. Other information such as sensor parameters (shown in block 707) may also be provided to or stored on the remote processing resources. Sensor parameters may include any of various types of information about the remote sensors and may be useful in interpreting sensor data 703 and/or generating accurate outputs from processing algorithms. Examples of sensor parameters include correction factors of particular sensors, conversion information for determining concentrations of particular components of sensed particles, parameters for reconfiguring operation of the monitoring units, etc. Using the data 703 and optionally sensor parameters 707, one or more algorithms 709 may provide one or more outputs. As examples, algorithms 709 may include statistical models, machine learning models, regression models, classification trees, random forest models, simple expressions (linear or non-linear), look up tables, and the like. In the depicted embodiments, processing logic for implementing algorithm(s) 709 includes instructions for implementing any one or more of a dashboard 711, time-weighted average values 713 of particle counts or other local conditions, material or compound (e.g., silica mass per unit volume of air) concentration values 715, and/or location mapping 717 (e.g., air quality maps for particular locations of provided data 703).

Additional example techniques with various monitoring unit or system configurations will now be discussed. In some embodiments, a monitoring unit, or a system having a monitoring unit, may be configured for use in determining a source of a sound in an environment. In various contexts, it may be advantageous to detect acoustic signals, determine whether those acoustic signals have exceeded a threshold magnitude (e.g., decibel level) or some other characteristic (e.g., a frequency-dependent characteristic), and determine whether those acoustic signals have caused, or will cause, an acute and/or cumulative exposure risk. Similar to the description herein, determining the source of the sound(s) exceeding the threshold may assist with reducing or mitigating the sound. Exposure to acoustic signals, i.e., sounds or noise, can be hazardous, both acutely and cumulatively over time, and various standards exist for determining thresholds of unacceptable exposures. For instance, the United States Occupational Health and Safety Administration ("OSHA") has set a noise exposure limit in the workplace to a time-weighted average of 90 decibels (dBA) over an eight-hour period. https://www.osha.gov/SLTC/noisehearingconservation/loud.html OSHA has also set other shorter-time exposure limits, which may be considered acute exposure limits, of, for example, 100 dBA over a two-hour period, and 115 dBA over a period equal to or less than 15 minutes. https://www.osha.gov/laws-regs/regulations/standardnumber/1910/1910.95.

Figure 14:
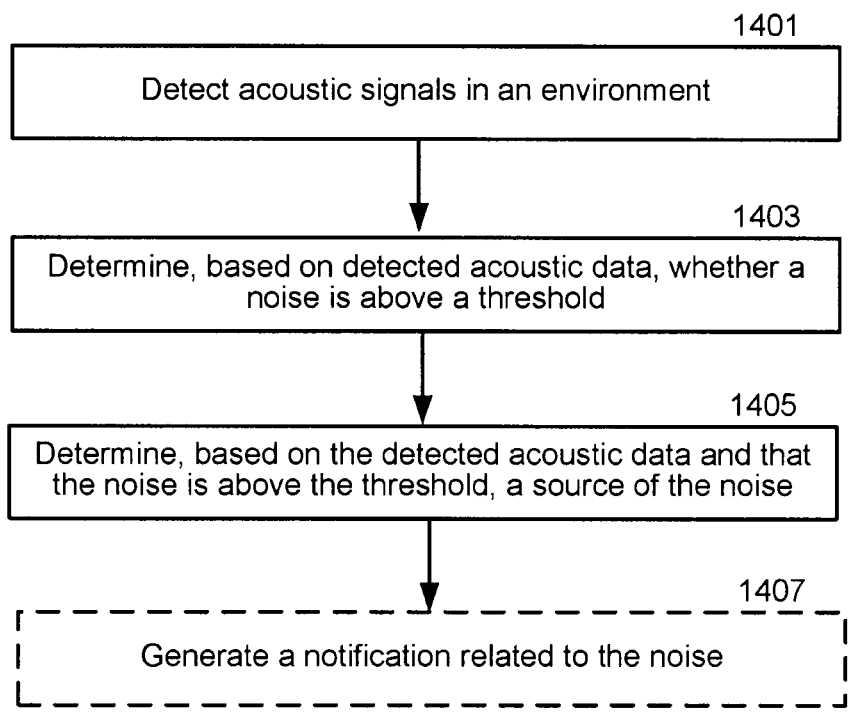
FIG. 14 depicts an example technique for monitoring acoustic data.

FIG. 14 depicts an example technique for monitoring acoustic data. In block 1401, acoustic signals in an environment may be detected. Some implementations of a monitoring unit, or a system having a monitoring unit, may have at least one acoustic sensor configured to detect acoustic signals, such as a microphone described herein (e.g., a dynamic, condenser, piezoelectric, carbon, and/or a ribbon microphone). In block 1403, instructions stored on the memory of the monitoring unit, or a system having a monitoring unit, and/or the memory of a remote computing unit may be configured to cause one or more processors to determine whether the detected acoustic signals have exceeded one or more thresholds, and/or will exceed one or more thresholds in the future, i.e., a predictive determination. These thresholds may be, for instance, one or more acute thresholds (e.g., an instantaneous sound above a particular level, such as 120 dBA, or a sound that occurs for a relatively short period of time, such as less than or equal to an hour, over a particular decibel level), one or more cumulative thresholds (e.g., a time weighted average of sounds exceeding a level over a period of time, such as an average of 90 dBA over eight hours), or both.

The instructions configured to cause one or more processors to determine whether the detected acoustic signals will exceed one or more thresholds, i.e., a predictive estimate, may be based on previously detected and stored data, and a determination of whether that data is associated with exceeding one or more thresholds over one or more future time periods. This predictive estimate, or predictive model, may be accomplished with various techniques, such as parametric, non-parametric, and semi-parametric models. As an example, such models may be trained using data from industry where the sensor is used or from other source. In some such implementations, the instructions may be able to cause the determination of whether a user may exceed a cumulative noise exposure threshold in a particular amount of time. For example, based on detected acoustic data over a first time period, such as the first 6 hours of a worker's shift, the predictive estimate may determine that the worker's noise exposure will exceed OSHA's 90 dBA over an eight hour period in the next two hours if corrective or other remediation measures are not taken.

As noted in block 1405, instructions stored on the memory of the monitoring unit, or a system having a monitoring unit, and/or the memory of one or remote computing unit may also be configured to cause one or more processors to determine a source of one or more sounds, including the source of one or more sounds that have exceeded one or more thresholds. The source may be a noise generating item inside or outside the environment, such as equipment, machinery, vehicles, explosions, or work activities (e.g., jackhammering), and many of these sources have unique acoustic characteristics that can be detected, stored, and used for this determination, which may be considered stored acoustic data. In some implementations, this determination may therefore be based, at least in part, on associating the detected acoustic data with those of the known, stored acoustic data that are associated with various sources. This association, which may be a comparison or other analysis, may be performed in different manners, such as comparing the frequencies, amplitudes, wavelengths, cycles, peaks, troughs, wave shapes, and the like, of the detected acoustic data with those of the stored acoustic data to determine whether the detected acoustic data has similar properties, e.g. within ±10%, ±25%, or ±5%, to the stored acoustic data, in order to associate or estimate whether the detected acoustic data matches the stored acoustic data for one or more sources. In some instances, the association between the detected and stored acoustic data may be made with algorithms and/or modeling, such as machine learning, neural networks, sound processing, and/or language translations. These algorithms and/or modeling may be trained with separately recorded acoustic data that is associated with equipment, machinery, vehicles, explosions, and/or work activities.

This determination of a source that generated acoustic data may, in some implementations, be triggered by, or made in response to, determining that one or more sounds that have exceeded one or more thresholds.

In some embodiments, determining the source that generated a detected acoustic data that is above a threshold may employ data from one or more additional sensors, such as those described herein, including a camera sensor, temperature sensor, location sensor, air quality sensor, or a gas sensor. Data provided by one or more of these sensors may further enable this source determination. For example, an air quality sensor and/or gas sensor may detect the presence of emissions associated with diesel exhaust which, when combined with the detected acoustic data, can be used to determine that the source of the detected acoustic data is associated with diesel machinery, such as a vehicle or heavy equipment. In another example, the location sensor can provide location-related information that can be used, for instance, to associate the location of monitoring unit with nearby noise generating items as well as the geography where the monitoring unit is positioned. For instance, the location-related information may indicate that a monitoring unit worn by a worker is within a particular distance to a known noise generating element, such as a locomotive or cement mixer, which can be used to determine that the source of the detected acoustic data is the known noise generating element. The location data may include, for instance, GPS data, location data within a particular environment such as a mine or a building, and/or an indication of whether the monitoring unit is inside or outside.

In some embodiments, the one or more acoustic sensors may be used to make additional determinations, such as the directionality of the detected acoustic data. This can be used to determine, alone or together with other determinations and/or data, the location of the emitted sound and what equipment or other sound generating items may be present in that location. In some implementations, multiple acoustic sensors may be used to triangulate the location of the emitted sound.

In another example, the camera (e.g., image and/or video camera), may provide imaging data that can be used to further assess the source of the detected noise data. The imaging data generated by the camera may be stored on a memory on the monitoring unit, or a system having a monitoring unit, and/or a remote computing unit, and/or instructions stored on such memories may cause processors to analyze that imaging data to determine the presence of noise emitting items, such as analyzing the presence and/or type of equipment, vehicles, or machinery, for instance. In some implementations, the temperature sensor may provide temperature data that again can be used to assist with determining the source of detected acoustic data, such as the proximity to a heat generating piece of equipment.

In some embodiments, image and/or video data from one or more cameras may also be used to determine the location and/or orientation of a person with respect to the detected acoustic signals. For example, the images may indicate that a person wearing a monitoring unit having one or more acoustic sensors and a camera is facing, or partially facing, a noise emitting source, such as an operating generator. This determination may be based, in some instances, on comparing the generated image and/or video data with stored image and/or video of the location or environment.

Detected acoustic data may also be used, in some embodiments, to determine proper functionality of equipment, vehicles, or other machinery and/or predict maintenance or malfunctions of items. In some such instances, stored acoustic data may include recordings of properly functioning and/or improperly functioning equipment which can be associated, correlated, and/or compared with detected acoustic data in order to perform various determinations of the equipment's functionality and/or maintenance. For example, the acoustic sensor may detect acoustics generated by a compressor and instructions may be configured to cause a processor to determine whether that compressor is functioning properly, needs maintenance, or when such maintenance is needed. Similar to above, this determination may be performed in different manners, such as comparing the frequencies, amplitudes, wavelengths, cycles, peaks, troughs, wave shapes, and the like, of the detected acoustic data with those of the stored acoustic data to determine whether the detected acoustic data has similar properties, e.g. within ±10%, ±25%, or ±5%, to the stored acoustic data, in order to associate or estimate whether the detected acoustic data matches the stored acoustic data for one or more sources. In some instances, the association between the detected and stored acoustic data may be made with algorithms and/or modeling, such as machine learning, neural networks, sound processing, and/or language translations. These algorithms and/or modeling may be trained with separately recorded acoustic data that is associated with the functionality (e.g., proper or improper functioning) of equipment, machinery, vehicles, explosions, and/or work activities.

In some embodiments, a notification may be generated in response to one or more of the above-described determinations regarding acoustics. In FIG. 14, optional block 1407 represents the generation of a notification after the above-referenced determinations are made. The notification may be presented by the notification mechanism described herein in any of the above-described forms. For example, these notifications may be an alarm, alert, message, an auditory output, an electronic communication, an electromagnetic communication, a visual output, and/or a tactile output. In some instances, the message may include information relating to noise exposures that have exceeded a threshold, noise exposures that may exceed a threshold in a particular time in the future (e.g., 30 minutes after issuing the notification), or potential remediations or other corrective actions associated with the detected acoustic data. For example, a notification message may be provided to a person wearing a monitoring unit that they have been exposed to one or more noises that have exceeded a threshold, that their noise exposure will exceed a threshold if they remain in the environment for an additional period of time, or that the person should take an action, such as to move away from a noise producing item or to use hearing protection.

In some instances, the notification may be provided to other devices or other persons not wearing the monitoring unit, such as a remote computing unit, another worker, a supervisor, a health and safety worker, or the like. In some instances, the notification may be provided to all monitoring units or remote devices within a particular spatial proximity to the monitoring unit that detected the acoustic data. For example, if one monitoring unit detects acoustic data that exceeds a threshold, then a notification about this acoustic data may be sent to mobile devices and/or monitoring units within a geographic region around the one monitoring unit.

In some embodiments, a monitoring unit, or a system having a monitoring unit, may be configured for use in determining an estimated heat stress in an environment. Heat stress typically represents the net heat load to which a person is exposed; heat stress can be caused by exposure to extreme heat or work in hot environments, and can result in heat-related illnesses such as heat exhaustion, heat stroke, heat cramps, or heat rashes. For instance, heat stroke is a serious heat-related illness that can occur when the body is unable to control its temperature which can occur when the body's temperature rises rapidly, the sweating mechanism does not work properly, and/or the body is unable to cool down. It is therefore useful in some situations to monitor and determine, in real-time, heat stress to which persons may be exposed as well as to predict potential heat stress risk to a person.

Heat stress can be determined or estimated using various factors such as environmental factors, e.g., temperature, humidity, wind, radiant heat, metabolic heat, or clothing worn by a person. The environmental factors, in some instances, may be considered a wet bulb globe temperature (WBGT) calculation that can include climatic variables of humidity, temperature, solar radiation, and/or wind speed in a rational thermodynamic heat exchange model. The calculated WBGT can also be adjusted, in some situations, to a WBGT effective by accounting for the clothing worn because clothing can affect the rate and amount of heat exchange between a person and the ambient environment by, for example, convection, conduction, radiation, and/or sweat evaporation. The metabolic work rate may represent some impacts to the body core temperature from the internal heat produced because of exertion.

Some embodiments of the monitoring unit, or a system having a monitoring unit, provided herein are configured to estimate a heat stress in an environment. The monitoring unit, or a system having a monitoring unit, may directly measure some heat stress related factors, such as temperature, humidity, body temperature, body impedance, heart rate, and/or access other related information such as a monitoring unit's location, cloud cover, clothing, or irradiance. In some embodiments, heat stress can be estimated using temperature and/or humidity data in an environment. This estimate can be calculated by making assumptions on typical values of other parameters in the environment such as a typical clothing factor. Solar radiation and/or windspeed data maybe estimated from other data based on location data, such as from a location sensor which may include a GPS antenna. In some implementations for indoor operations, such as steel mills and casting operations, typical values of all other parameters may also be known.

Figure 15:
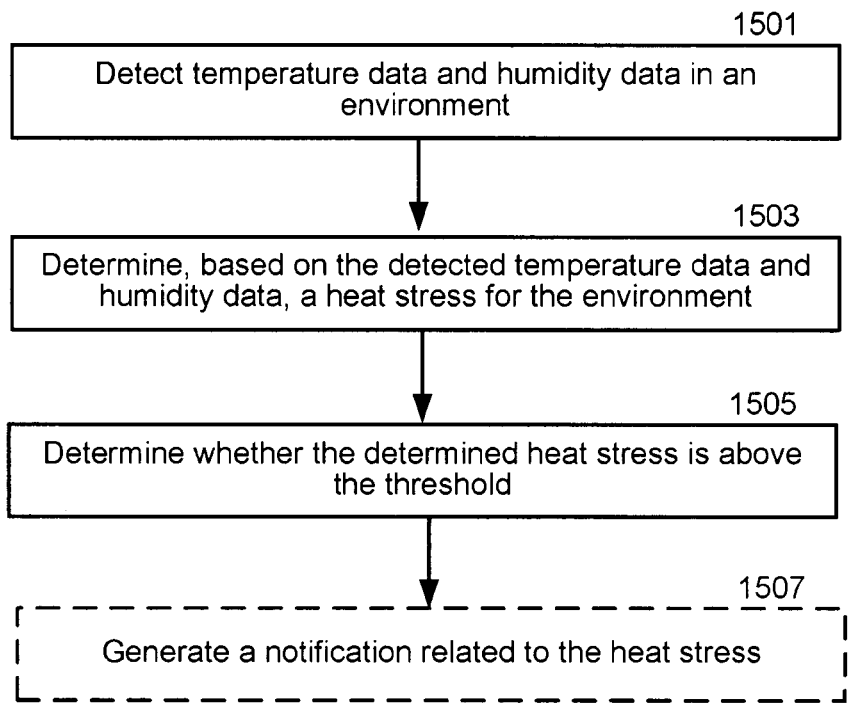
FIG. 15 depicts an example technique for determining heat stress.

FIG. 15 depicts an example technique for determining heat stress. The monitoring unit, or a system having a monitoring unit, may, in some embodiments, have a temperature sensor configured to generate temperature data and a relative humidity sensor configured to generate humidity data, as described herein. In block 1501, the temperature and humidity data are detected in the environment. The temperature sensor and relative humidity sensor may generate temperature and humidity data in an environment which is stored on a memory of the monitoring unit, a remote computing unit, or both. The temperature data may be ambient temperature around the monitoring unit or a body temperature of a person. For some wearable monitoring units, the temperature sensor may be a part of the monitoring unit, while in some other implementations, the temperature sensor may be separate from a housing of the monitoring and connected through wired or wireless connections to the monitoring unit.

In block 1503, instructions stored on a memory of the monitoring unit, or a system having a monitoring unit, and/or a remote computing unit, may be configured to cause one or more processors to determine, based on the received temperature and humidity data, an estimated heat stress in the environment. This may include estimating the WBGT using the detected temperature and humidity data, and approximating other aspects of the WBGT model, such as estimated irradiance, wind speed, and/or clothing.

In some embodiments, the monitoring unit, or a system having a monitoring unit, may include other sensors that generate data used in the heat stress determination. These sensors may include a heart rate sensor, a light sensor (e.g., a photoelectric device, a photosensor, a photodetector, and/or other sensor configured to convert light photons into current), a location sensor, or a body impedance sensor. The heat stress determination may use the data generated by these sensors in various manners, such as using heart rate data generated by the heart rate sensor and/or the body impedance sensor to determine a metabolic work rate of a person, using light intensity data generated by the light intensity sensor to determine irradiance on the monitoring unit or person, or location data to determine whether a person is indoors or outdoors, which may affect irradiance and/or wind, for example. In some instances, data generated by the body impedance sensor may be used to determine a hydration level of a person. The location data may also be used, in some embodiments, to access and gather climate or other environmental conditions of the environment from remote sources, such as weather stations or weather sites. These climate conditions may include, for instance, wind speeds and/or direction, humidity, cloud cover, and/or solar irradiation which can affect the heat stress determination. The location sensor may be a sensor configured to gather location of the monitoring unit by GPS, WiFi, Bluetooth, or other wireless means.

In block 1505, a determination is made as to whether the estimated heat stress is above a threshold. Thresholds may be set by various governmental agencies and may be based on, for instance the percentage of work performed by a worker or the type of workload, such as rest, light, moderate, heavy, and very heavy. Some example limits include _WBGT of 31 C and 28 C for light and moderate work-load on a continuous (100%) basis. In some embodiments, a determination of the percentage of work performed by a worker may be based, at least in part, on data from an accelerometer and/or gyroscope, including movement or activity data. In some implementations that use a heart rate sensor, an intensity of work performed may be determined from heart rate data of a worker.

In some instances, the heat stress determination may account for clothing worn by a person. Clothing may, for example, have different categories for heat stress related purposes, such as work clothes (e.g., long sleeves and pants, standard cotton shirt/pants), coveralls (e.g., with only underwear underneath, cotton or light polyester material), double-layer woven clothing, Spunbond Meltblown Spunbond (SMS) polypropylene coveralls, polyolefin coveralls (e.g., micro-porous fabric), or limited-use vapor-barrier coveralls (e.g., encapsulating suits, whole-body chemical protective suites, firefighter turn-out gear). The heat stress determination may be adjusted by applying an adjustment factor based on the type of clothing worn.

A person may provide an input as to their clothing, or estimated type of clothing, which can be received by the one or more processors and applied in the determination. This may also be provided by other information that can be stored on the memory, such as calibration, settings, or start-up information provided by a non-user of the monitoring unit, such as a different worker, e.g., a superintendent or supervisor, or safety employee. In some embodiments, a clothing may be provided by other means, such as automatically retrieving clothing related information from a data store of a clothing manufacturer, employer, job site, joy or work type, etc., or based on sensor data, such as a location data.

In addition to instantaneous and real-time determinations of heat stress, some implementations may also determine a predictive, or future, heat stress. The memory may therefore store instructions that are configured to cause one or more processors to determine whether the detected heat stress related factors, e.g., temperature and humidity, will exceed one or more heat stress thresholds over one or more future time periods. This predictive estimate, or predictive model, may be accomplished with various techniques, such as parametric, non-parametric, semi-parametric models, and/or machine learning models. In some such implementations, the instructions may be able to cause the determination of whether a user may exceed a heat stress threshold in a particular amount of time. For example, based on detected temperature and humidity data over a first time period, such as the first 6 hours of a worker's shift, the predictive estimate may determine that the worker's heat stress exposure will exceed a threshold over an eight hour period in the next two hours if corrective or other remediation measures are not taken.

In some implementations, a predictive determination may be based on trend analysis. For example, if a WBGT is increasing, it may be determined that if the present rate of temperature increase persists, the worker will cross a threshold in a particular amount of time. In another example, the predictive determination may be based on a weather forecast combined with current sensors readings. If the weather forecasts hotter temperatures, then based on a current detected temperature, it may be determined whether the threshold will be exceeded at a later time that day.

In some embodiments, a notification may be generated in response to one or more of the above-described determinations regarding heat stress. In FIG. 15, optional block 1507 represents the generation of a notification after the above-referenced determinations are made. The notification may be presented by the notification mechanism described herein in any of the above-described forms. For example, these notifications may be an alarm, alert, message, an auditory output, an electronic communication, an electromagnetic communication, a visual output, and/or a tactile output. In some instances, the message may include information relating to heat stress that has exceeded a threshold, heat stress that may exceed a threshold in a particular time in the future (e.g., 30 minutes after issuing the notification), or potential remediations or other corrective actions associated with the heat stress. For example, a notification message may be provided to a person wearing a monitoring unit that their heat stress has exceeded a threshold, that their heat stress will exceed a threshold if they remain in the environment for an additional period of time, that the person is at risk for a heat stress related illness, such as heat stroke, or that the person should take an action, such as hydrating, taking a break, or moving to shade.

In some instances, the notification may be provided to other devices or other persons not wearing the monitoring unit, such as a remote computing unit, another worker, a supervisor, a health and safety worker, or the like. In some instances, the notification may be provided to all monitoring units or remote devices within a particular spatial proximity to the monitoring unit that detected the acoustic data. For example, if one monitoring unit detects heat stress that exceeds a threshold, then a notification about this heat stress may be sent to mobile devices and/or monitoring units within a geographic region around the one monitoring unit.

In addition, or alternatively, to the above description related to a camera, some embodiments of a monitoring unit, or a system having a monitoring unit, provided herein may use a camera to assist, at least in part, with making various determinations. The camera may, in some embodiments, be a part of a stationary, a wearable, or a mobile monitoring unit, or separate from a housing of a monitoring unit and/or communicatively connected to the monitoring unit through a wired or wireless connection. In some implementations, a camera may be configured to generate image data (e.g., still images) and/or video data, which may be collectively referred to herein as "image/video data", "image/video", or "images/video", that can be analyzed to determine an activity performed in an environment.

Determination of an activity occurring in an environment may be performed in various manners. In some implementations, this may include associating imaging/video data generated by the camera with known, stored imaging/video data that are associated with various activities. This association, which may be a comparison or other analysis, may be made with algorithms and/or modeling, such as machine learning, neural networks, and/or other image processing. These algorithms and/or modeling may be trained with separately recorded imaging/video data that is associated with equipment, machinery, vehicles, explosions, work activities, worker movements such as walking, stepping, lifting, falling, loading, unloading, climbing, or descending.

Similar to above, in some implementations, a camera's operation may be tied to local sensor outputs. In certain embodiments, the camera may record images/video may be triggered by one or more thresholds described herein being exceeded (e.g., particulate matter concentration, heat stress, gas level, acoustic). For example, if particulate matter concentrations as detected by the air quality sensor described herein, exceed a particular threshold, then the camera may be triggered to record images and/or video for a certain amount of time after that triggering.

Alternatively, or additionally, in some embodiments, the camera may record images/video within a particular time before and/or after sensor parameters have exceeded or will exceed a threshold, or have provided another indication to capture and store images/video. For example, when a monitoring unit is operating, the camera may always be recording images/video and only storing on the memory the images/video taken within a set period from any given point in time. For instance, the camera may always be recording images/video and only storing the images/video five minutes in the past of any given point in time; at time 10:00 am, the images/video from 9:55 am to 10:00 am are stored. Storing some historical images/video assists with determining activities and other events that may occur around the monitoring unit and/or camera. When one or more of the thresholds provided herein may be exceeded, the instructions may be configured to cause the camera to retain the stored historical imaging/video data and to record and store additional imaging/video data until an indication is received to stop such recording, such as from a power button or a user input. This stored imaging/video data may be used to analyze the activity or source that may be associated with the threshold being exceeded. For example, imaging/video data may be used to associate detected acoustic data exceeding a threshold with a corresponding noise producing event, such associating a loud noise with equipment falling onto the ground.

Accordingly, any of the monitoring units described herein and any of the determinations described herein may use imaging/video data to assist with any determination. This may include assisting with a determination associated with a threshold being exceeded, or a separate determination, such as determining an activity within the environment, or both.

Figure 16:
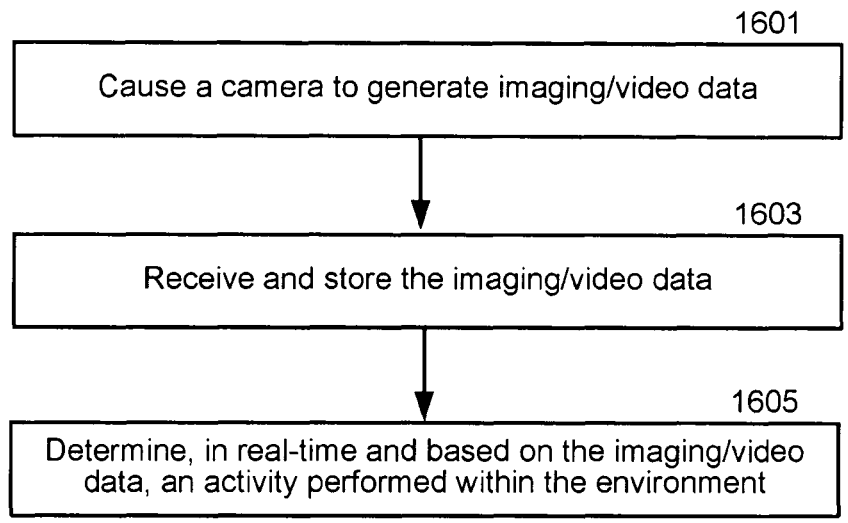
FIG. 16 depicts an example technique for determining an activity performed in an environment.

FIG. 16 depicts an example technique for determining an activity performed in an environment. In block 1601, instructions stored on a memory of the monitoring unit or in the system causes a processor to cause the camera to generate imaging/video data as described herein. This may be, in some instances, according to a trigger, such as detecting and/or determining that a metric or condition is above a threshold. In block 1603, the imaging/video data is received and stored by a memory on the monitoring unit, remote computing unit, or aspect of the system. In block 1605, a determination is made, in real-time and based on the imaging/video data, of an activity performed within the environment. This determination is made according to the description herein.

Various industries, emissions, and/or other activities are subject to visible emissions standards and there is a need for monitoring and determining whether visible emissions have exceeded the relevant standards. In some embodiments, the imaging/video data may be used to monitor and/or determine such visible emissions, including dust or other particulate matter within, entering, or exiting an environment. For some visible emissions standards, the United States Environmental Protection Agency has used the Method 9 technique to determine opacity by, in some instances, taking opacity readings of plumes at 15-second intervals and averaging 24 consecutive readings. Some of the cameras provided herein are configured to take imaging/video data, including according to the Method 9 technique, in order to monitor and determine some visible emissions standards.

In some embodiments, the imaging/video data may be combined with data from other sensors to monitor and determine visible emissions. This may include gathering data from one or more cameras plus, for example, one or more air quality sensors and/or gas sensors. In some instances, particulate concentration data from the air quality sensor imagining/video data from a camera can be used to determine the opacity of an environment (including of a plume of emissions), the direction of the emissions or other particulate matter including whether some is being emitted inside the environment, flowing into the environment, or flowing out of the environment. In some embodiments, the other sensor may include a sensor configured to measure distances, such as a LiDAR ("light detection and ranging" or "laser imaging, detection, and ranging") sensor which may also be considered 3-Dimensional laser scanning or laser scanning. Some such sensors illuminate a target with a laser beam, including emissions and particulate matter that passes through the laser beam, and measuring the reflection with a sensor. Differences in laser return times and wavelengths can be used to make various determinations about the emissions, such as concentration, direction, and speed.

As mentioned above, in some embodiments the camera may be positioned in the monitoring unit and at least some of the determinations may be made on one or more processors in the monitoring unit. In some embodiments, alternatively or additionally, the imaging/video data generated by the camera may be transmitted by the communications interface to a remote computing unit and at least some of the determinations may be made on one or more processors in the remote computing unit.

Additionally, or alternatively, to gas sensors provided herein, in some embodiments, a monitoring unit, or a system having a monitoring unit, may have one or more gas sensors configured to generate chemical composition data of a gas in the environment. The gases may include, for example, oxygen, carbon dioxide, carbon monoxide, hydrogen sulfide, methane, and/or combustible gases. These monitoring units, or systems having a monitoring unit, may be configured to make real-time detections and determinations of the gas in the environment. This may include, for instance, instructions stored on a memory to cause one or more processors to determine and measure, in real-time, the presence and/or concentration of the gas in the environment and/or in some implementations, determine a source of the gas. In some instances, determining the source of the gas may include accessing gas information stored on a memory of the monitoring unit and/or a remote computing unit, and associating the detected gas with the gas information. This association may take various forms, such as a look-up table or database which associate gases with sources that emit such gases (e.g., a table that provides sources that emit detected propane), mapping a gas concentration as the unit is moved through an environment and identifying a potential direction of the source by analyzing the gas concentration gradients.

This association may, in some implementations, use information from other sources, such as accessible public information (e.g., a weather site or stations), stored information (e.g., climate data, data indicating the type of equipment used in the environment, or stored location data such as that the environment is a mine in a state) or sensor data, such as location data, air quality data, or temperature data.

In some embodiments, the instructions stored on a memory may further be configured cause one or more processors to determine whether the determined concentration of the gas in the environment is increasing or decreasing, and/or whether that concentration has exceeded a threshold. In some such implementations, a notification may be issued when the threshold has been exceeded, when the concentration of the gas is increasing, including at a particular rate, and/or when the concentration of the gas is decrease, including at a particular rate.

In some embodiments, the gas sensor may be a part of any of the other monitoring units and/or systems described herein and provide additional data that may be useful in any of the determinations or detections. For example, the presence and concentration of one or more gases may assist with determining a source of acoustic noise in an environment. Using detected acoustic data and chemical composition data of the gas may provide further information and data, such as associations between noises and emitted gas, e.g., a sound of an operating diesel engine and one or more gases in diesel exhaust, that can be used to associate detected sounds with sources of those sounds. In another example, the presence and concentration of one or more gases may assist with determining activities in an environment in a similar manner; by providing additional data that can associate detected images/video with one or more gases. For example, associating an image of a cracked pipe with detected natural gas to determine the presence of damage to the pipe.

Figure 17:
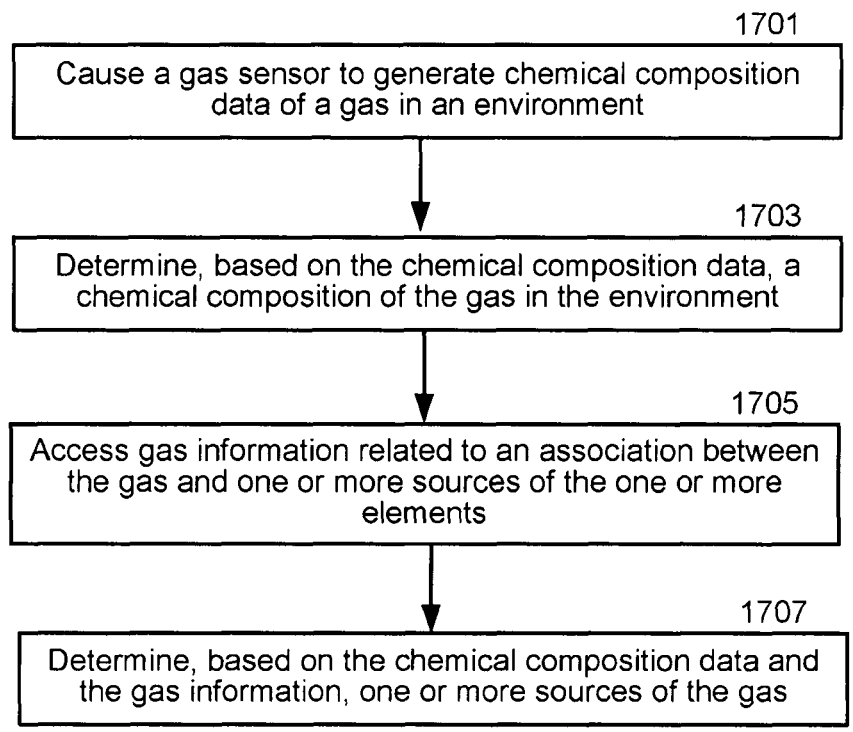
FIG. 17 depicts an example technique for determining a source of a gas in an environment.

FIG. 17 depicts an example technique for determining a source of a gas in an environment. In block 1701, instructions stored on a memory of the monitoring unit or in the system causes a processor to cause the gas sensor to generate concentration data of a gas in the environment, described herein. This may be, in some instances, according to a trigger, such as detecting and/or determining that a metric or condition is above a threshold. Although not included in FIG. 17, this data is received and stored by a memory on the monitoring unit, remote computing unit, or aspect of the system. In block 1703, a determination is made, based on the gas and the concentration data, a chemical composition of the gas in the environment, as described herein. In block 1705, the gas information is accessed, as provided herein, and in block 1707 a determination is made as to one or more sources of the detected gas, as also described herein.

A monitoring unit, or a system having a monitoring unit, may include any combination of the sensors provided herein and the monitoring unit, or a system having a monitoring unit, and/or a remote computing unit may be configured to make any of the detections or determinations described herein that are associated with the sensors. This may include, for example, a monitoring unit having a camera and a plurality of gas sensors each configured to detect and measure a different gas. In another example, the monitoring unit may include a camera, humidity sensor, temperature sensor, a location sensor, and an acoustic sensor. This monitoring unit and/or a remote computing unit communicatively connected to the monitoring unit may be able to make any determination with respect to these sensors, such as determining an activity in the environment or an estimated heat stress.

Additionally, any of the monitoring units and sensors provided herein may be used as part of various systems. This may include a system having one or more of any of the sensors and/or one or more of any of the monitoring units provided herein. For example, a system may include monitoring unit with an acoustic sensor, a temperature sensor, and a humidity sensor, and a camera separate from the monitoring unit, but configured to generate video/images of the environment and communicatively connected with one or more processors of a remote computing unit and/or the monitoring unit.

Similar to above, in some embodiments computational logic may be used to generate maps of anything detected, measured, and/or determined described herein, such as detected acoustic signals, determined heat stress, detected or determined gas concentrations, air quality, particulate matter, sources of any type of emission, or areas in which such measured quantities have exceeded a threshold, for example. The logic may be configured to generate such maps using only limited information, from one or more sensors, typically from multiple sensors which may be stationary or mobile sensors. Such maps may be generated using an appropriate model such as a statistical model, e.g., Kriging, or machine learning model, e.g., an artificial neural network. The maps may be produced by interpolating the detected or determined item, e.g., acoustic signals, between measuring locations (fixed and/or mobile). To provide interpolated information from data provided at only a few discrete locations, a model may be trained using data provided at many different locations beyond simply those of installed sensors in the final system. In certain embodiments, a mapping routine may evolve or improve over time by using additional training data acquired by moving wearable sensors providing real time readings of the measured and/or determined items at various locations aside from the fixed monitors that might continually detect and/or determine the items at fixed locations. In some embodiments, the generated map may represent the amounts or concentrations of the detected, measured, and/or determined item within an area of the environment.

For example, this control logic may use a bidirectional multi-layer perceptron (MLP) long short term memory (LSTM) network to perform a spatio-temporal interpolation. The LSTM network has been used for use in natural language processing and performs efficient treatment of time-series data. The item measured by sensors, or determined, at sampled locations at time t may serve as an input to the model while the interpolated concentrations at time t at various locations (which may be test locations) is the output. The bi-directional LSTM, in addition to the item measured, or determined, at time t, will also take into account historic measurements/determinations and/or future measurements/determinations to perform the interpolation. The analysis of past and/or future measurements/determinations may allow, in some instances, the model to be robust to changes in the environment, such as changes to air flow directions and to different activities within the environment.

In some embodiments, training of the model may be carried out using a high-density sensor network placed in a lab environment with controlled or a mobile sensor where the coordinates of the mobile sensor, the time and the measured/determined quantity are being recorded. This high-density sensor network or mobile sensor data may be collected over a period of time, such as hours, days, or weeks, to ensure adequate data points for training and testing are gathered. Once fully trained for a given location (test location), the accuracy of the algorithm for performing the spatio-temporal interpolation may be evaluated using only data form the sampling sensor location.

In some instances, mapping may be based, at least in part, on the measured or determined item and the location of a measurement point (e.g., the location of a sensor). The location may be the relative location between different measurement points, the relative location within the environment, and/or the absolute geographic location on the Earth (e.g., latitude and longitude coordinates from, for example, GPS measurements). Additional data may include geographic and/or environmental information of the environment, such as a layout of the environment, topography, geographic features (e.g., for outside areas, trees, barriers, hills, walls, buildings; e.g., for inside areas, walls, windows, doors, ceilings), or gas flows (e.g., for outside areas, wind speeds and/or direction, or other climate information; e.g., for inside areas, windows, air intake and/or outlet locations, HVAC locations, and/or gas flows).

In some embodiments, the instructions may be further configured to cause the processors to determine a location of a source of the detected air particles, gas, or acoustic signals as described above. This may include the relative and/or absolute locations of such estimates. Some implementations may determine this by locating one or more maximal of a detected signal in an environment which, in some cases, will correspond to the source of the signal, i.e., the source of the detected air particles, gas, or acoustic signals.

Figure 18:
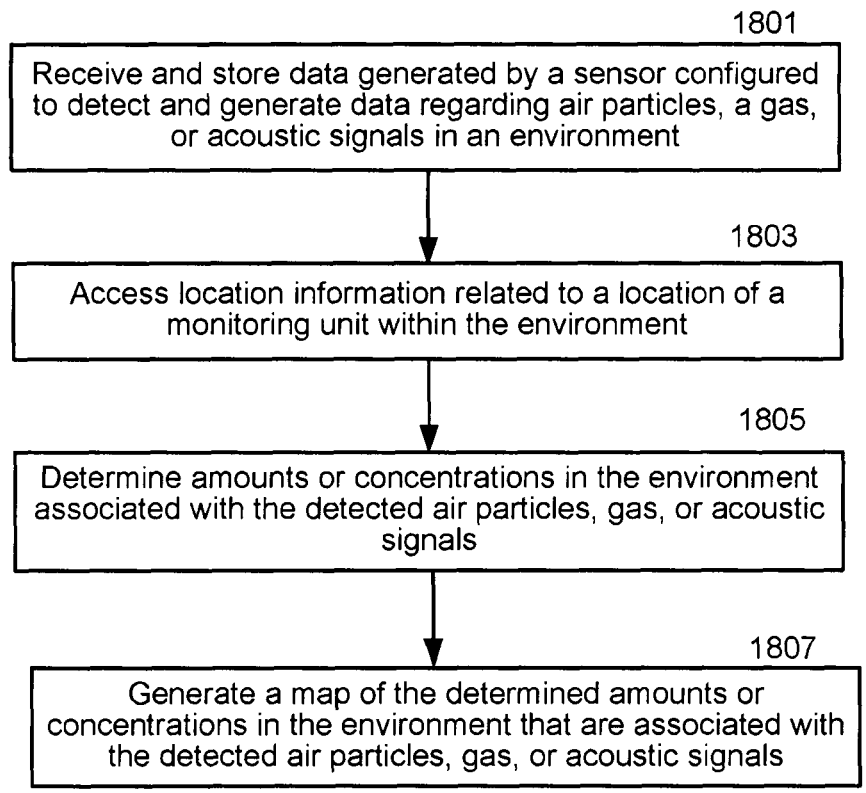
FIG. 18 depicts an example technique for generating a map of detected and/or determined metrics or conditions in an environment.

FIG. 18 depicts an example technique for generating a map of detected and/or determined metrics or conditions in an environment. In block 1801, data that is generated by a sensor is received and stored by a memory on the monitoring unit, remote computing unit, and/or other aspect of a system. This data may be data regarding air particles, a gas, or acoustic signals in the environment, such as any of those described herein. Although not included in FIG. 18, this data is received and stored by a memory on the monitoring unit, remote computing unit, or aspect of the system. In block 1803, location information is accessed relating to a location of the monitoring unit within the environment, as described herein. In block 1805, a determination is made, based on the data generated by the sensor and the location information, amounts or concentrations in the environment that are associated with the detected air particles, a gas, or acoustic signals, as provided herein. In block 1807, a map may be generated of the determined amounts or concentrations, in the environment, that are associated with the detected air particles, gas, or acoustic signals in the environment, as also described herein.

Some embodiments provided herein may also be configured to perform monitoring and determining relating to a boundary of an area. This is sometimes referred to as "fence line monitoring" and can involve one or more sensors positioned at or near an area's boundary in order to detect and determine various metrics and/or conditions crossing and/or present at the boundary. This may include, for instance, monitoring particulate matter or gases generated inside an area that cross the boundary and exit the area, as well as particulates or gases that enter the area; this may also include determining whether the particulate matter or gases exiting the area exceed one or more thresholds, such as various emissions standards.

A system configured to perform such monitoring and/or determining related to a boundary of any area may include one or more sensors positioned at or near the boundary. This positioning may be at or on the boundary, inside the boundary within a particular distance from the boundary, or outside the boundary within a particular distance from the boundary. These distances may be based, in some examples, on various regulations and rules, such as the United States Code of Federal Regulations (CFR), including 40 CFR section 63.658(k)(4)(i), and/or those developed by States and/or various local air quality management districts. This may include, for example, monitoring particulate matter within about 2,000 or 1,000 feet from the boundary. This may also include monitoring total amounts of various particulates or gases that have exited or entered the area.

The one or more sensors may be a part of a monitoring unit, as described herein, or may be a standalone sensor communicatively connected to a controller. In some embodiments, each sensor may be configured to detect particulate matter, such as the air quality sensor provided herein, or to detect gases, such as the gas sensors included herein. The system may be configured to detect the presence, amounts, and/or concentrations of particulate matter and/or gases at or near the boundary as based on sensor data generated by the one or more sensors, and received and stored by the processor, and configured to determine whether the detected presence, amounts, and/or concentrations of particulate matter and/or gases at or near the boundary exceeds a threshold. The detections and/or determinations may be made in any way provided herein.

Some embodiments of this system may also be configured to determine whether the detected air particles and/or gas are exiting or entering the environment. This determination may use the data generated by the sensors, as well as location data representative of the sensor location, such as the sensor's location relative to the boundary or absolute position. This determination is made, in some instances, by doing a mass balance of the particles and/or gas on one boundary as compared to another part of a boundary, such as a boundary opposite the one boundary; this comparison may depend, in some instances, on wind direction data and/or air flow data, including wind direction data in and/or around the environment. For example, if the wind direction is North-South around and in an environment having north and south boundaries, then a concentration of particles and/or gas detected by the sensors on the north boundary may be subtracted from the concentration detected along the south boundary to yield the concentration generated from within the facility. Similar determinations can be made on a dynamic basis depending on the wind direction and/or air flow patterns obtained either from external data or measured locally by one or more wind vanes and anemometers.

In some embodiments, this determination may also use wind or air flow data related to air flow within, around, and/or outside the area. This air flow data may assist with determining whether the detected particulate matter and/or gas was generated inside or outside the area, or is increasing or decreasing. It may also assist with determining the path of travel of the particulate matter and/or gas. The air flow data may be from a weather station communicatively connected to the processor and which may be a part of the system, from publicly available weather data, from an anemometer or other wind speed sensor, or other external sources including any of those provided herein (e.g., an external website or public server, a remote computing unit). In some instances, the air flow data may include flow rates and/or information related to the direction of the air flow, such as compass directions or directional components relative to the sensor or area.

Figure 19:
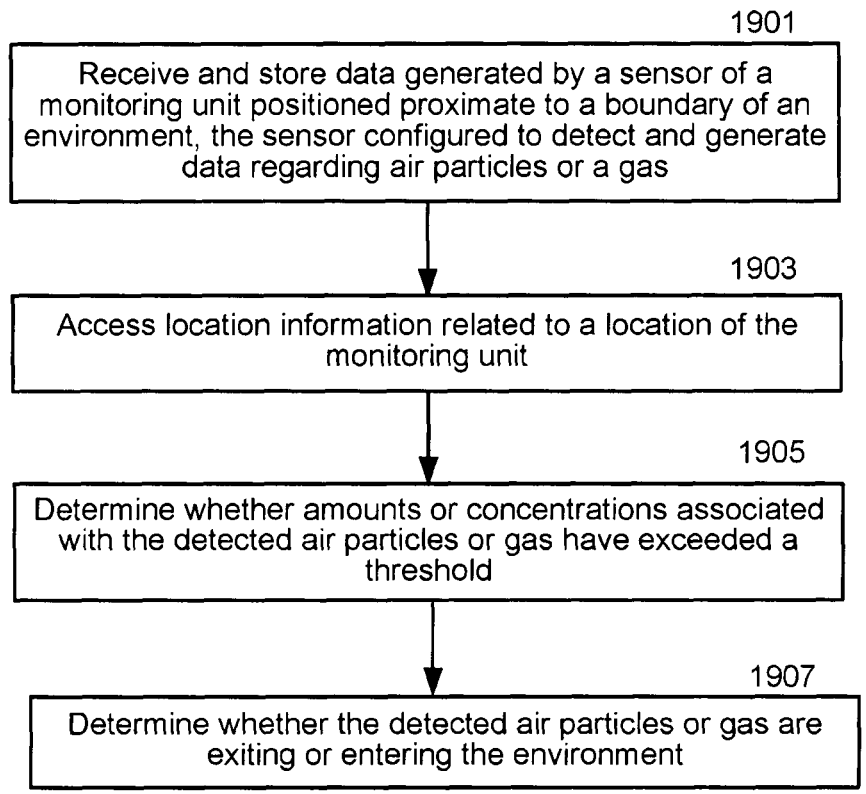
FIG. 19 depicts an example technique for monitoring and determining various aspects relating to a boundary of an area.

FIG. 19 depicts an example technique for monitoring and determining various aspects relating to a boundary of an area. In block 1901, data that is generated by a sensor is received and stored by a memory on the monitoring unit, remote computing unit, and/or other aspect of a system. This data may be data regarding air particles and/or a gas, such as any of those described herein. Although not included in FIG. 19, this data is received and stored by a memory on the monitoring unit, remote computing unit, or aspect of the system. In block 1903, location information is accessed relating to a location of the monitoring unit within the environment, as described herein. In block 1905, a determination is made, based on the data generated by the sensor and the location information, as to whether amounts or concentrations in the environment that are associated with the detected air particles or gas have exceeded a threshold, as provided herein. In block 1907, a determination may be made as to whether the detected particles or gas are exiting or entering the area.

Although not shown in FIG. 19, the system may also include a notification mechanism, such as that described herein, configured to generate a notification regarding the detected particulate matter and or gas. This notification may indicate, for example, that particulate matter or gas is detected (e.g., detecting the presence of dust), or that detected particulates or gases have exceeded a threshold. The notification may take any of the forms mentioned herein, such as an alarm or an electronic message to a worker in the area.

In some embodiments, the system may also include a camera configured to generate images and/or video, and/or a laser sensor, that can be used to determine the opacity of air at or near the boundary. This determination may be made in any way described herein. Machine learning algorithms may be used to determine existence of a plume and then determine an opacity of the plume. Some examples of machine learning algorithms include Convolution neural networks for analysis of the image data to determine opacity of the plume. This opacity determination may assist with determining whether dust or other particulate matter has been generated within the area and is exiting the area.

Figure 20:
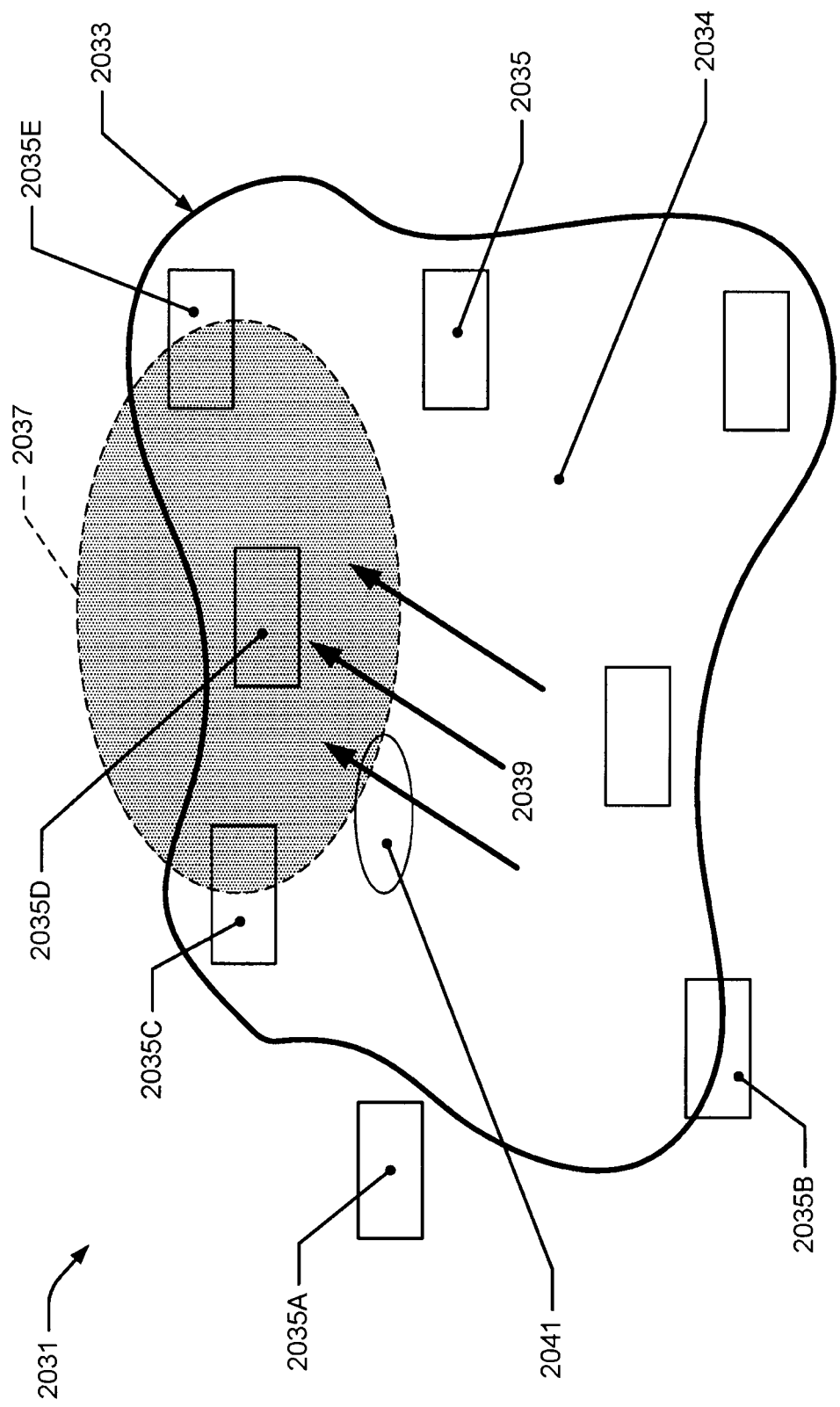
FIG. 20 depicts another example system.

FIG. 20 depicts another example system. Here, this system 2031 is configured to perform monitoring and/or determining relating to a boundary 2033 of an area 2034 encompassed by the boundary 2033. This system 2031 includes a plurality of sensors 2035, which may be considered any of the monitoring units provided herein. These sensors 2035 are positioned at or near the boundary 2033, including outside the boundary 2033, e.g., sensor 2035A, on the boundary 2033, e.g., sensor 2033B, and within the boundary 2033. Each of these sensors may be configured to detect particulate matter or gas. In some embodiments, each of these sensors 2035 may instead be a monitoring unit as described above which may include multiple sensors, such as an air quality sensor and a gas sensor.

As provided herein, this system 2031 is configured to detect the presence, amounts, and/or concentrations of particulate matter and/or gas which is represented by a shaded ellipse 2037. Here, this particulate matter and/or gas 2037 is around sensors (or monitoring units) 2035C, 2035D, and 2035E which are configured to detect the presence, amount, and/or concentration of this condition and also to make any of the determinations provided herein, such as whether the concentrations of this particulate matter and/or gas 2037 exceeds a threshold. As also illustrated, air flow (represented by arrows 2039) is occurring inside the boundary 2033 and the system 2031 may be configured to use this air flow data, and/or in some instances location data of the sensors 2035, to determine whether this particulate matter and/or gas 2037 is flowing out of or into the area 2034. In this Figure, the particulate matter and/or gas 2037 is flowing out of the area 2034.

In some embodiments, a system may be configured to perform the boundary monitoring/determining, and the mapping as provided herein.

Similar to described above, in some embodiments, a system may be provided that includes multiple sensors and is configured to determine a source of a gas or particulate matter in an environment. In some embodiments, the system may be configured to determine a concentration of a detected particle and what the particle is or represents. This may include varying levels of speciation information, such as chemical composition, elemental composition, and/or optical composition. For example, this may include determining whether the detected particle is organic or inorganic, or what the elemental composition of the particle is, such as whether it is aluminum or zirconium, for instance.

In some embodiments, the system may include a first sensor positioned in the environment and configured to generate particle data regarding particles in the environment, which may be the air quality sensor described herein, a second sensor positioned in the environment and configured to determine speciation data of the detected particles, and/or a third sensor positioned in the environment and configured to determine elemental composition data of the particles. Based on the detected and/or determined information by the sensors, instructions stored on a memory of the system may cause a processor of the system to determine a source of the detected particles. This may be done, for example, using a chemical mass balance model to appropriate the elements to respective sources based on an emissions inventory stored on one or more memories. This may include accessing a look-up table, database, or other stored information that associates the detected and/or determined information with characteristic elements of known sources, such as associating detected carbon with smoke, or detected carbon with vehicle smoke. These determinations may also be made using machine learning or other algorithms provided above, such as neural networks.

In some embodiments, the system may also access and use air flow data, and/or location data when making these determinations. The air flow data may include a direction and flowrate of wind or other air movement in the environment. This data be able to identify a location of a source of the detected particles, including a location relative to one or more sensors that detected such particles. The system may also, in some embodiments, determine a contribution of one or more of the determined sources to an air quality of the environment. In some instances, the particles may be elemental, composites, organic or inorganic, and the determinations may also be made in real-time.

Referring to FIG. 20 as an illustrative example, in some embodiments the system 2031 may be a system configured to determine a source of the emissions 2037 which may be considered particulate matter. In some such embodiments, each item 2035 may be considered one of the first, second, and/or third sensors, and/or a monitoring unit having one or more of the first, second, and/or third sensors, that are positioned within or around an environment 2034. The system 2031 may therefore be configured to detect and/or determine the presence of the particulate matter 2037 and determine a source 2041 of the particulate matter 2037.

In some embodiments, the system may have at least one particle sensor, such as the air quality sensor provided herein, a black carbon sensor, a total carbon sensor, and/or a trace element sensor. Using data from these sensors, the sensor is configured to determine a source of detected particles. As provided, this determination may be performed by a source apportionment (receptor) model such as a chemical mass balance or positive matrix factorization. In some implementations, these determinations may also be made in real-time on the remote computing unit (e.g., the cloud), and/or on an edge device.

User Interfaces

The data generated and information determined by one or more monitoring units and/or the remote computing unit may be presented in various manners. In some instances, data and information may be presented on the monitoring unit itself, similar to described above. Referring back to FIG. 1, this data and information may be presented via the notification mechanism 174 and, referring back to FIGS. 4A and 4B, via the display 446. For example, the display 446 of a mobile monitoring unit 402 may display particle size, particle counts, particle mass concentration, size distribution, volume concentration, size distribution, particle composition/type, time weighted averages, exposure risk factors, safety risk factors, real time mapping, geolocation data, and time. Additionally, data and information presented to a wearer may include an alert or alarm, such as flashing lights and sounds.

Figure 8:
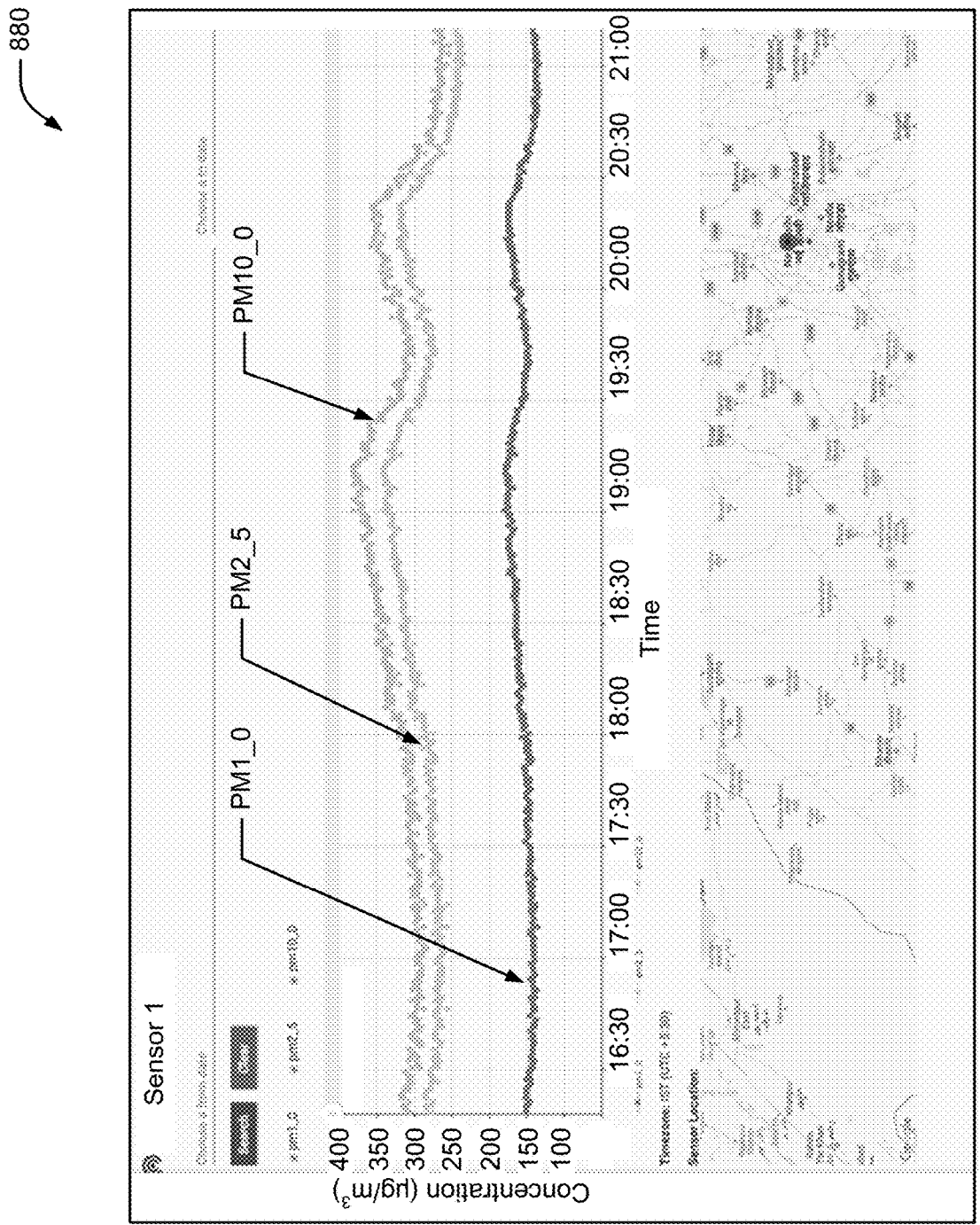
FIG. 8 depicts a first example dashboard.

The generated data by one or more monitoring units and determined information may also be displayed in a dashboard on an electronic device, such as a computer, laptop, table, smart phone, and the like. The dashboard may include any of the data measured and information determined as described above. For example, FIG. 8 depicts a first example dashboard. The dashboard 880 includes a graph which displays detected particulate concentrations, in micrograms per meter cubed ($\mu g/m^3$), over time for three different size bins of particles, PM1.0, PM2.5 and PM10.0. As can be seen, the detected particulate concentrations for each size bin changes over time, with a maximum peak between time 19:00 and 19:30, and another increase between time 20:00 and 20:30. The dashboard 880 also includes a map showing the geographical location of the monitoring unit in real time and historically.

The dashboard may be interactive such that a user can select and access historical and real-time data of mobile monitoring units and stationary units. For example, the dashboard may allow a user may to select a historical location of a mobile monitoring unit and then display the data and information that were generated and determined for that location. Referring to FIG. 8, the data in the chart may be the data generated by a monitoring unit at the location depicted in the map.

Figure 9:
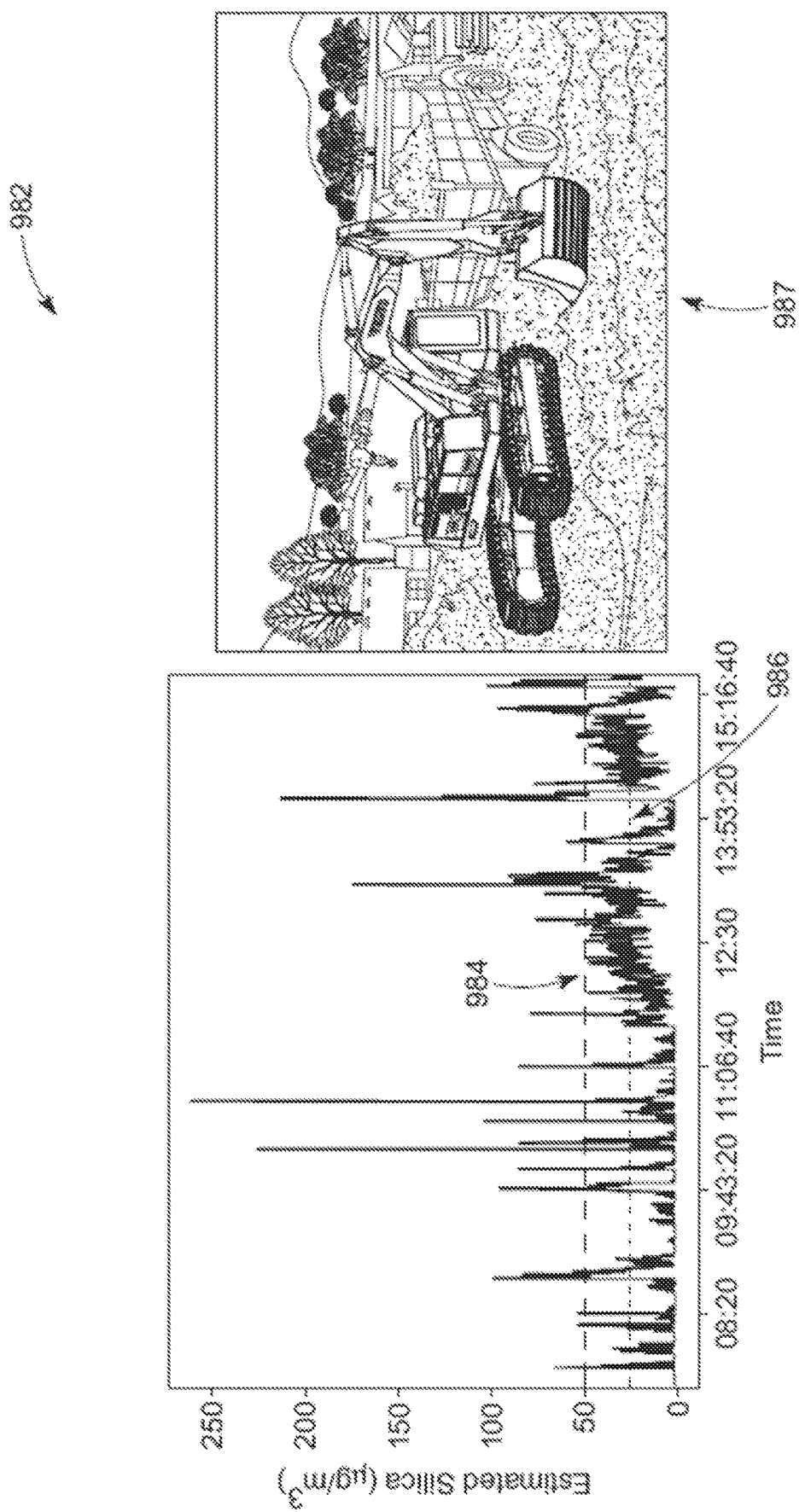
FIG. 9 depicts a second example dashboard.

The dashboard may also display time-weighted average information. In certain embodiments, the image/video taken by a camera as directed by sensor output maybe displayed on the dashboard along with the sensor output relevant to the image. See item 987 in FIG. 9. FIG. 9 depicts a second example dashboard; here, the chart depicts estimated silica measurements made by a mobile monitoring unit worn by a user over time, approximately 8 hours. The mobile monitoring unit may use the air quality sensor 108 described above to detect total respirable dust over a time period and a correction factor may be applied to determine the estimated amount of silica within the detected respirable dust. In this instance, as indicated in FIG. 9, it is assumed the respirable dust contains 32.6% to 40% of silica (this may be obtained by a material safety data sheet (MSDS) for that respirable dust stored in or accessible by the cloud computing unit). The detected respirable dust can then be adjusted using this assumption in order to obtain the estimated silica, in micrograms per meters cubed, over the time period. The data shown in the chart represents that estimated silica, which is the measured respirable dust data adjusted by the assumed silica percentage of that respirable dust.

As noted above, the measured data may be used to determine the time-weighted average (TWA) which indicates the average exposure to a material over a fixed time interval, such as an 8-hour workday. In FIG. 9, the eight hour time weighted average (TWA) was obtained for the measured respirable dust, which is 58.13 $\mu g/m^3$. Because it is assumed that the measured respirable dust contains an assumed silica percentage of 32.6 to 40, the measured respirable dust is multiplied by this percentage to determine an estimated silica TWA, which is 18.95 to 23.25 $\mu g/m^3$.

The second example dashboard 982 may also include level thresholds of detected exposures, such as permissible exposure limits and action levels. For instance, FIG. 9 includes a permissible exposure limit line 984 which may indicates the permissible amount of exposure for silica, which is illustrated as 50 $\mu g/m^3$. Although the estimated silica 8-hour TWA (18.95 to 23.25 micrograms per meter cubed) is below this threshold, dashboard 982 shows that the mobile monitoring unit detected numerous short-term exposures that were higher than this threshold, such as between times 9:43:20 and 11:06. Determining specific instances higher than the permissible exposure limits is advantageous for monitoring and taking corrective actions to improve health and safety of an environment. For instance, if these exposures were determined for a jackhammer operator, these instances can be used to assess which work conditions may have caused these exposures and to take corrective action to prevent or stop these exposures, such as using different safety measures in these conditions in the future, as well as issuing real-time warnings to the user during these exposures.

Similarly, another level threshold may be an action level threshold which indicates when an action should be taken with respect to the exposure. FIG. 9 includes action level threshold 986 which represents the level at which an action should be taken based on the detected conditions. These actions can include, for instance, instituting additional monitoring, turning on or installing engineering or safety controls, issuing a notification (e.g., that exposures are above a particular level), and the like. The action level threshold may also be below the exposure limit threshold in order to prevent the exposure limit threshold from being reached.

Figure 10:
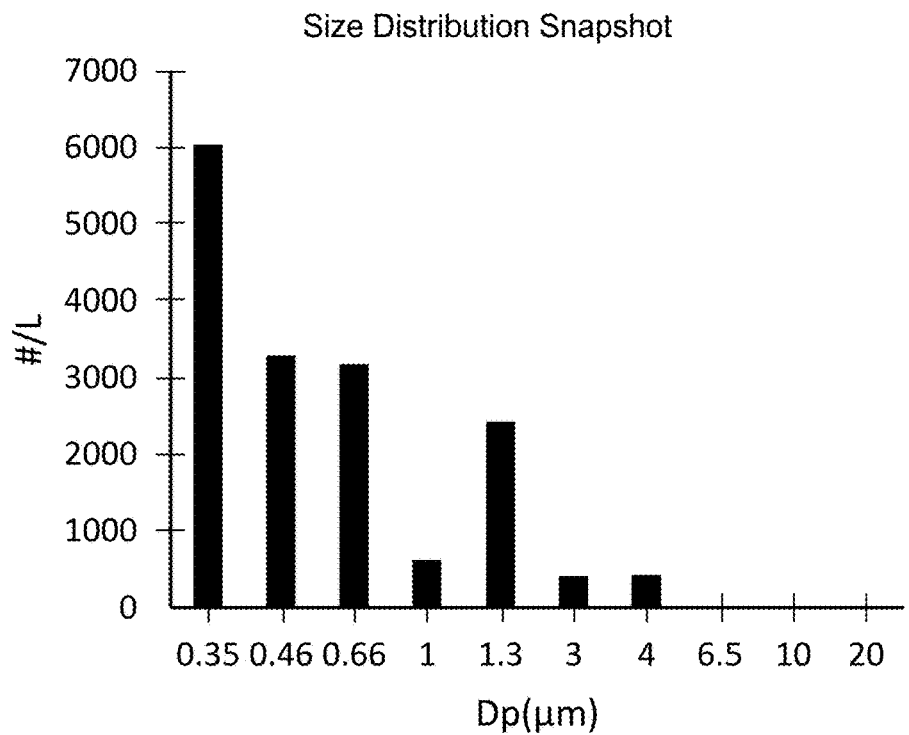
FIG. 10 depicts a histogram of a size distribution snapshot for the air quality sensor of a monitoring unit.
Figure 11:
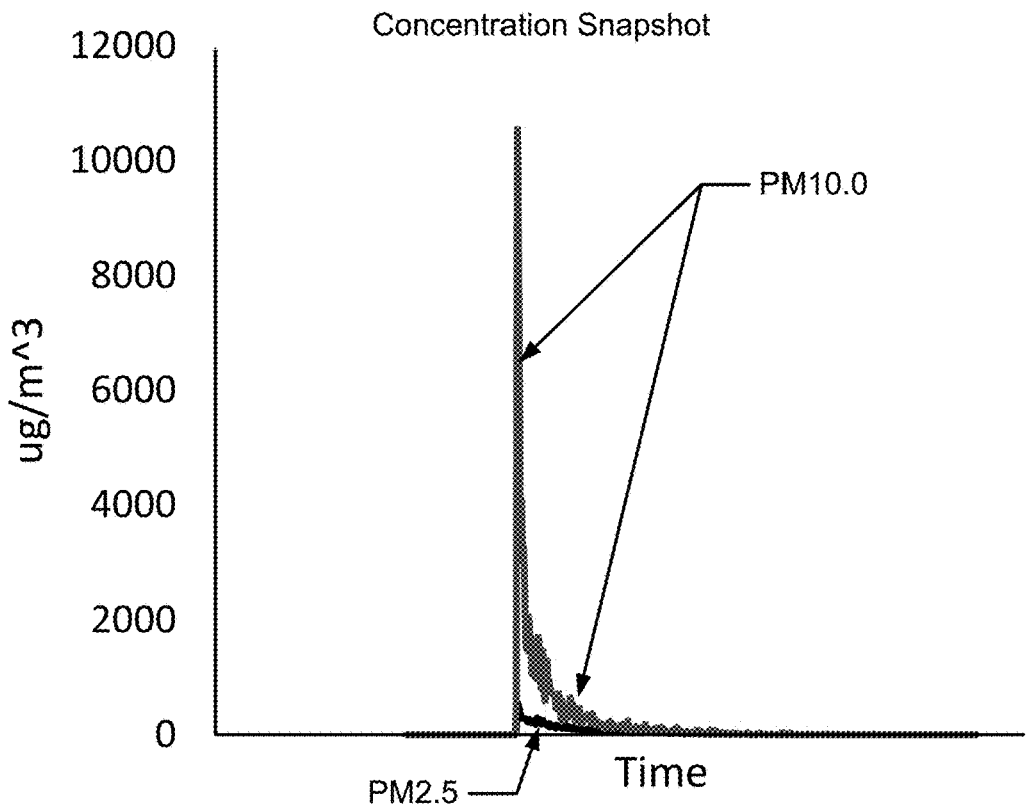
FIG. 11 depicts a concentration snapshot of detected particles of different sizes over a time period.

The dashboard may also present real-time concentration and size distributions. FIG. 10 depicts a histogram of a size distribution snapshot for the air quality sensor of a monitoring unit. Here, the vertical axis shows the number of particles per liter and the horizontal axis shows the diameter of the particle, in micrometers (μm). The time or time period which is depicted can vary. In some embodiments, the "snapshot" may be the measurements at a specific time or may be an average of the readings over a time period. For example, the air quality sensor may take measurements every 500 milliseconds and the snapshot may be the average of those measurements over 1 second, or 5 seconds. In FIG. 10, the numbers per liter (#/L) of detected particles of various sizes is seen. For instance, 6,000 particles per liter of particles having a diameter of 0.35 μm has been detected, and approximately 750 particles per liter of particles having a diameter of 1.3 μm has also been detected. Similarly, FIG. 11 depicts a concentration snapshot of detected particles of different sizes over a time period. Here, two particle masses are seen, PM10.0 and PM2.5, and over this illustrated time period, the concentration of particles with mass PM10.0 was much higher than the concentration of particles of mass PM2.5.

In some embodiments, the dashboard may also present a map that illustrates concentrations of one or more metrics within a particular area or environment. These metrics may be any measured or determined item described herein, such as particulate matter, specific particles and compounds, e.g., silica or carbon monoxide, temperature, sound, and relative humidity. In some implementations, the graphical representation may look similar to a heat map with differently colored or shaded gradients indicating different concentrations levels of the one or more metric(s). The map's graphical representations may be generated using the above techniques, such as interpolations of data generated by sensor readings. In some of these embodiments, measurements of one or more environmental conditions are taken at specific, known locations and values of the one or more metrics in between these locations may be interpolated. For example, a plurality of monitoring units may measure environmental conditions that include particulate matter, temperature, pressure, and relative humidity at a plurality of known locations within an environment, and the levels of a metric, such as particulate matter, may be determined at those known locations and in-between those known locations using the techniques described above. The plurality of monitoring units may be communicatively connected with each other, like in FIG. 3, and may also be communicatively connected with the cloud computing unit which may perform some or all of the interpolations and techniques described herein.

Figure 12:
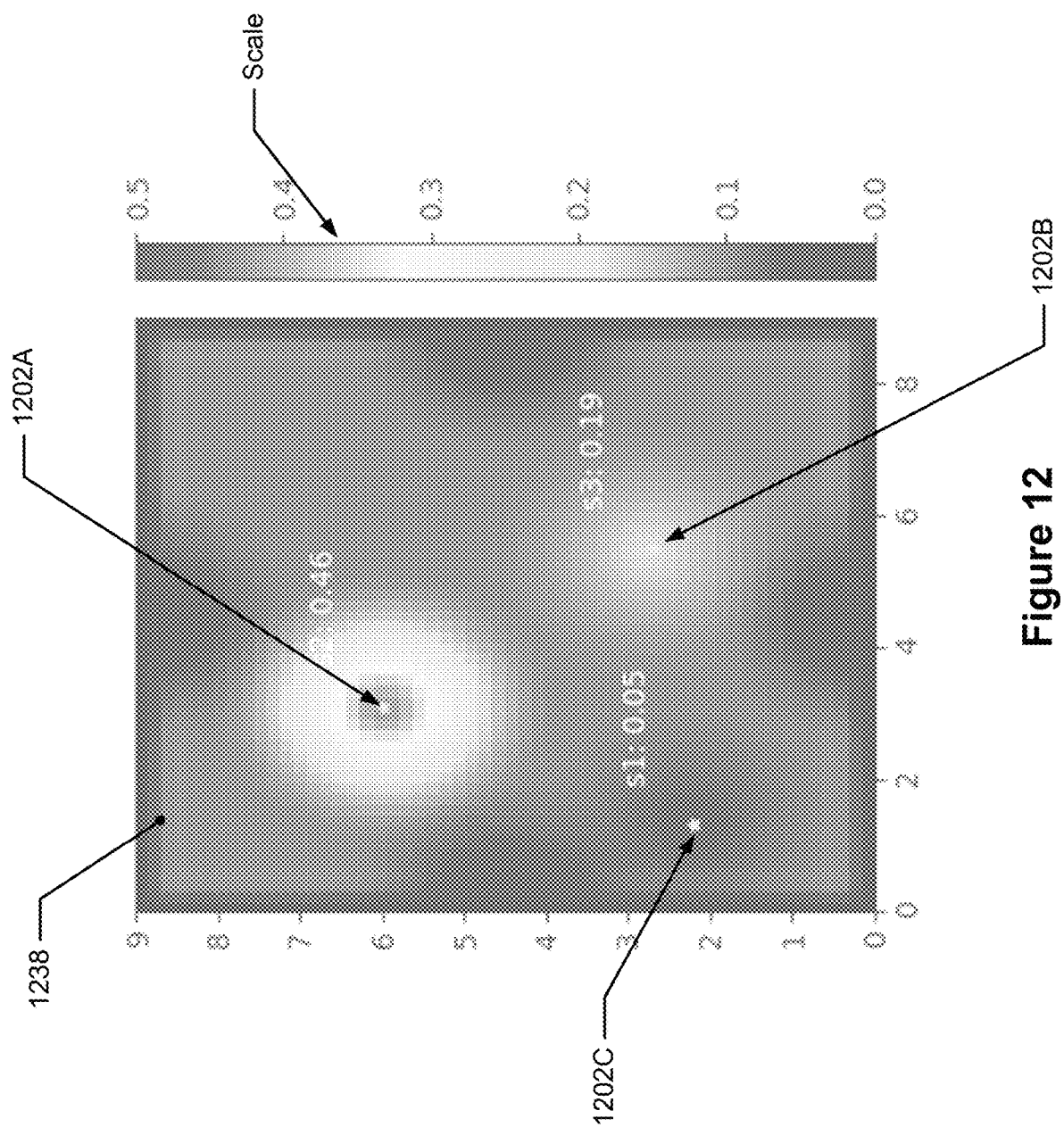
FIG. 12 depicts an example dashboard map.

FIG. 12 depicts an example dashboard map. Here, the depicted environment 1238 is a rectangular room which includes multiple monitoring units 1202A-1202C, represented as stars, positioned throughout the environment 1238. The levels of a metric, based on the data gathered by the sensors of each monitoring units 1202A-1202C, is graphically represented in the room according to the vertical gradient scale on the right; higher levels of the metric are generally indicated in lighter color while lower levels are generally depicted as darker. As can be seen, the highest levels of the metric are around the monitoring unit 1202A (0.46 generic measurement units (GMU)), with the next highest levels around monitoring unit 1202B (0.19 GMU), and with lowest level around monitoring unit 1202C (0.05 GMU). As stated above, each monitoring unit measures one or more environmental conditions at its location and the metric is determined at and in between those known locations using techniques described above.

Based on the displayed information in FIG. 12, it may be inferred that an event occurred around monitoring unit 1202A which caused the highest levels of the metric to occur at that general location in the environment. For example, each of the monitoring units 1202A-120CH may have air quality sensors 1208 configured to detect and count particulate matter, as described above, and the metric depicted in FIG. 12 may be detected and interpolated particulate matter. In this example, the particulate matter is highest around monitoring unit 1202A and lowest around monitoring unit 1202C.

Figure 13A:
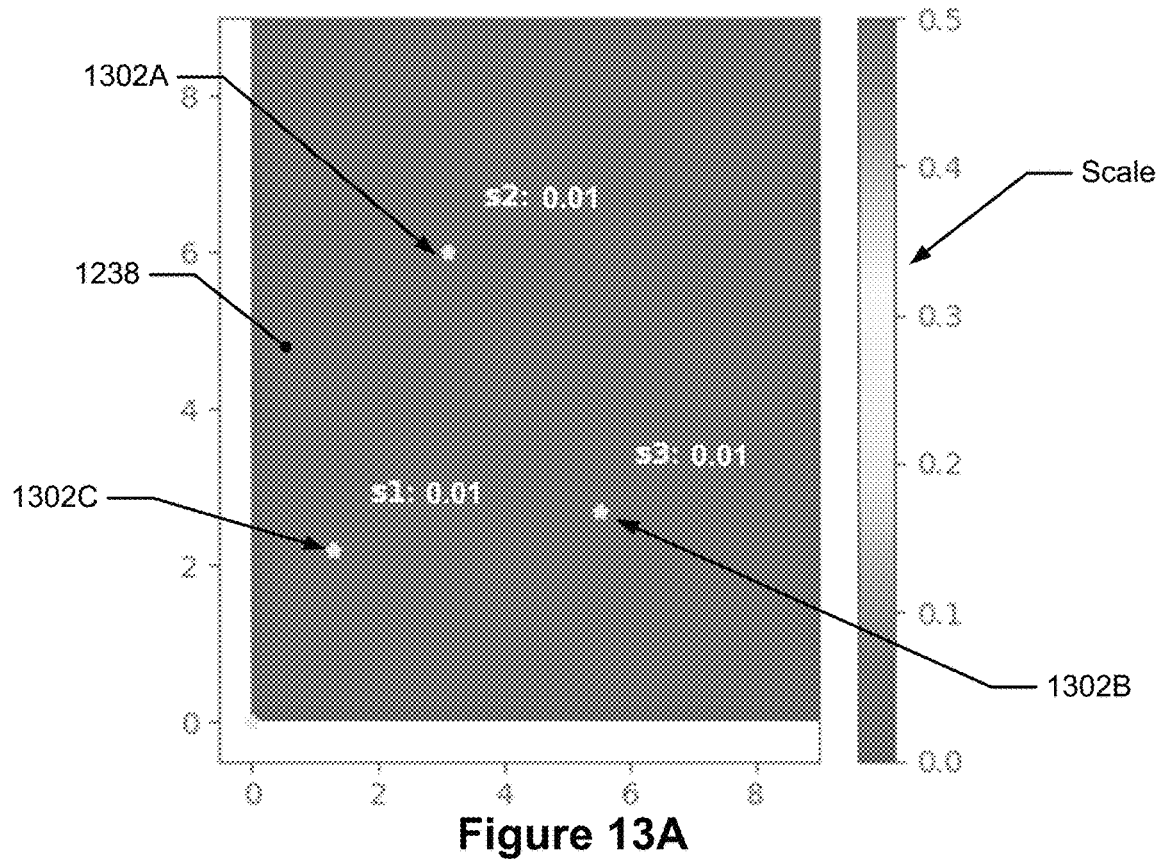
FIGS. 13A-13C depicts an example map sequence.
Figure 13B:
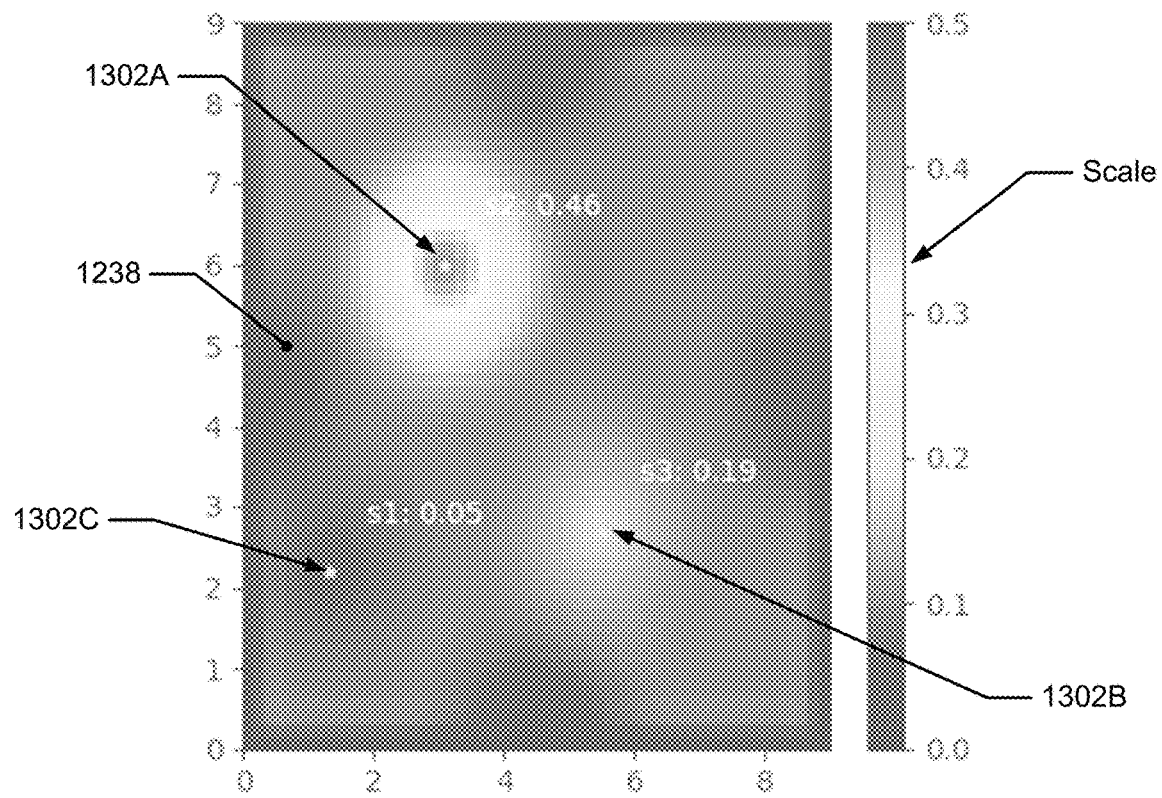
Figure 13C:
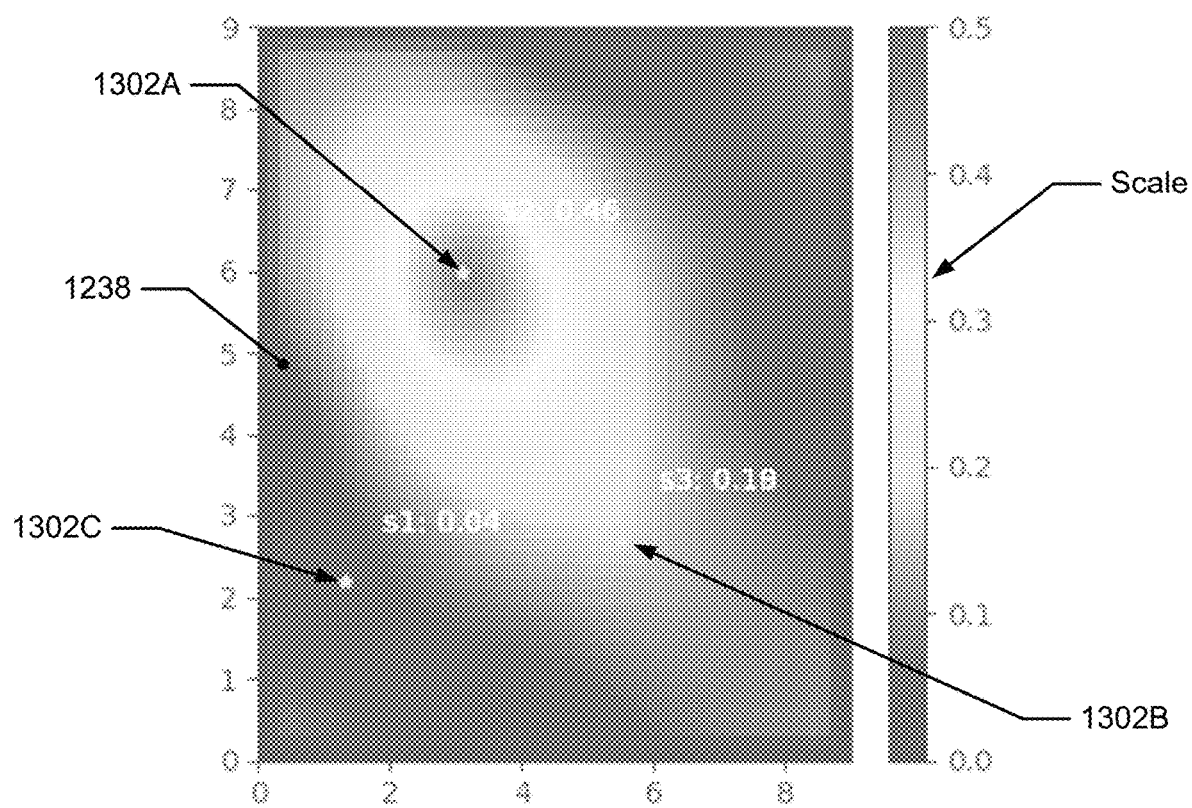

In some instances, the dashboard map may provide a snapshot at a particular time. In some other instances, the dashboard map may illustrate a sequence of a metric's levels within an environment over a period of time. FIGS. 13A-13C depict an example map sequence. Similar to FIG. 12, the depicted environment 1338 in FIGS. 13A-13C is a rectangular room which includes multiple monitoring units 1302A-1302C, represented as stars, positioned throughout the environment 1338. Again, like with FIG. 12, the levels of a metric, based on the data gathered by the sensors of each monitoring units 1302A-C, is graphically represented in the room according to the vertical gradient scale on the right; higher levels of the metric are generally indicated in lighter color while lower levels are generally depicted as darker.

Each of FIGS. 13A-13C may be considered a snapshot of the metric at different sequential times. In FIG. 13A, the first in the sequence at time 1, all the monitoring units 1302A-C are reading negligible levels, about 0.01 GMU at each unit. In the second sequence of FIG. 13B, an event has occurred in which a metric's levels have increased in the depicted environment 1338. As can be seen, the highest levels of the metric are seen around monitoring unit 1302A, about 0.46 GMU, with the next highest level around monitoring unit 1302B, about 0.19 GMU, and the lowest levels around monitoring unit 1302C, about 0.05 GMU.

In FIG. 13C, the levels of the metric detected by monitoring units 1302A and 1302B have remained the same, the have the levels around monitoring unit 1302A has increased and grown in size. Between these two Figures, the levels of the metric indicate that the metric has moved within environment 1338 and also increased in level. This sequence illustrates how differing levels of a metric within an environment over time can be illustrated by a dashboard. The dashboards are not limited to a schematic of a room, but can also illustrate concentrations using other representations, such as a geographical map. In FIGS. 13A-13C, a particulate generating event occurred around monitoring unit 1302A and these Figures illustrate the movement and increase of particulates within the environment 1338.

Additionally, as described above, the depicted concentrations or levels of a metric may also be based on monitoring units that are moving, stationary, or both. The examples of FIGS. 12 and 13A-C depict stationary monitoring units, but the same illustrations may utilize mobile monitoring units as well. Based on the known locations of the monitoring units, whether they are stationary or mobile, the values of metrics between these locations can be interpreted and graphically represented on a map. In some such examples, the map may also indicate the various locations or paths of the monitoring units while is some other examples, the map may not include the locations of any of the monitoring units.

As mentioned above, the data gathered by monitoring units and outputs described herein can be used for industrial hygiene reports. In some instances, the dashboards may display the information for some industrial hygiene reports. These reports can include, for example, end of shift analysis such as total TWA and silica TWA; instantaneous and acute exposure analysis during the shift and associated images/videos pertaining to the instantaneous exposure; risk factors determined by the data gathered including the exposure data, the activity data, and the image data; information on the sampling time (start time, end time); task or activity; influencing factors; process parameters; surrounding environments; specific events during the sampling period; objective data; insights regarding the root cause of the exposures; suggestions for effective remediation measures; and exposure levels.

Example Applications

The apparatuses and techniques described herein can be used for numerous applications. For instance, these apparatuses and techniques assist with safety in a variety of occupations, such as mining, construction, agricultural, pharmaceutical, industrial, manufacturing, firefighting, and the like. In these occupations, an individual worker's instantaneous, real-time, and TWA exposures to various hazardous materials, such as coal, silica, lead, chromium (VI), hazardous aerosols, gases, volatile organics, CO, $CO_2$, Ozone, $SO_2$, NOX, VOC, HCN, methane, radon, radioactive particles, and other potentially hazardous materials such as those identified in the American Conference of Governmental Industrial Hygienists (ACGIH) Threshold Limit Values/Biological Exposure Indices (TLVs/BEIs) tables, may be determined using mobile monitoring devices worn by the workers and positioned within occupational locations, such as within a mine, around a construction site or refinery, and within a manufacturing plant. This may allow for real-time monitoring of a worker's exposure to hazardous materials, for alerts or alarms to be issued to a worker, manager, or safety personnel, and for corrective actions to be taken such as instituting more monitoring, increasing or decreasing engineering controls such as fans or filters to remove the hazardous materials from an area. It may also be used to determine when worker must be wearing PPE and when it is safe to remove PPE. It may also be used to determine safe return of worker to a process area after a hazardous process has completed and it is safe for workers to enter the area.

These apparatuses and techniques may also be useful to public health and safety. For example, these monitoring units may be positioned around and worn by people in cities, homes, and municipalities for the monitoring and/or detection of harmful and hazardous materials. This may include detecting and determining city-wide pollutants from automobiles, and area wide particulates and hazardous materials produced by a fire. This may also include monitoring and determining an area's risk assessment COPD, asthma, and/or other health conditions.

The apparatus and techniques described herein may also be used to control the ventilation in a building effectively. In this case the system output may be used to drive a control to change ventilation rates in a building or mine or any enclosed environment.

The apparatus and techniques described herein may be used for early detection of equipment failure, infrastructure failure, or hazard. For example, small particle detection/VOC detection in a data center may be an early indication of a fire.

During natural or manmade disasters, such as emergencies, explosions, combustion, and/or wildfires, that affect outdoor air quality, the apparatuses, techniques, systems, and/or monitoring units may be used to measure, monitor, and/or make various determinations regarding outdoor and/or indoor air quality in an environment that may contain pollutants, such as pollutants caused by or related to wildfire smoke, a natural or manmade disaster, emergency, explosion, combustion. For example, wildfire smoke may spread to areas where outdoor workers perform their work and it is advantageous, or potentially required, for employers to monitor the workers' exposures levels and to potentially take corrective action, such as requiring the use of PPE or requiring work to stop. In a specific example, the State of California in 2020 issued regulations related to exposures to wildfire smoke which including, among other things, requiring employers to make reasonable efforts to protect workers. As of the filing of this application, some regulations can be found at: https://www.dir.ca.gov/dosh/wildfire/Worker-Protection-from-Wildfire-Smoke.html Accordingly, in some embodiments, the apparatuses, techniques, systems, and/or monitoring units may be configured to determine real-time air quality, including particle data including PM2.5, of an environment that contains pollutants, including any byproduct of combustion, such as wildfire smoke or toxic fumes, and to determine real-time potential exposure risks in that environment. The air quality determination may be based, in some instances, on at least particle data of the air quality sensors described herein. Some implementations may also base these determinations on location data, weather or environmental data such as wind data, imaging and/or video data (which may include determining an opacity of the environment), or any of the other data provided herein. In some implementations, a system or monitoring unit may have a notification mechanism configured to issue a notification indicating when a particular threshold has been exceeded. For example, if it is determined that an air quality index (AQI) for PM2.5 is greater than or equal to 151, then a notification may be issued. This notification may be issued, in some instances, on a monitoring unit worn by a worker, such as the issuance of information on a display, and/or generation of sounds or lights. This notification may also be issued, in some implementations, on or by any mobile or stationary monitoring unit, or other device such as a cell phone, computer, and/or emergency warning system.

In some embodiments, a determination of real-time potential exposure risks in an environment may be based on multiple sensors and/or monitoring units within the environment. This may enable monitoring of various metric or threshold exceedances, such as exceeding PM2.5, across an area to further determine potential high-risk areas and scenarios related to timing, location, or process occurring in the area and environment. This may be application to assess and determine various risks across a large area and/or workforce where other hyper-local data is not available, accessible, or in existence.

Similar to provided above, a determination may also be made, based on detected data and/or accessed information, of whether the AQI for an area is approaching, or is estimated to exceed a limit at a future time; this may be considered a predictive determination. Such predictions may be based on detected data, such as data from one or more air quality sensors, as well as location data, weather or environmental data such as wind data, imaging and/or video data (which may include determining an opacity of the environment), or any of the other data provided herein. The prediction may be made in any of the manners described above.

Unless the context of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein. The term "substantially" herein, unless otherwise specified, means within 5% of the referenced value. For example, substantially perpendicular means within +/−5% of parallel.

In certain embodiments, the systems and methods described herein are configured to track a person's location as either indoors or outdoors. In certain embodiments, the systems and methods described herein are configured to determine if the indoor environment is air-conditioned or not. This may be based on RSSI data from cellular systems and/or GPS data, along with temperature, humidity data and/or and their changes. A person entering indoor may see a drop in cellular and GPS RSSI. Using temperature and humidity changes linked to the above changes, the air conditioning of the indoor environment maybe detected. In some cases, a camera may further be used to make the indoor/outdoor determination using image recognition.

In some applications, the ability to monitor noise exposures experienced by an individual or at a given location is determined using acoustic signals captured using the microphone. The logic for detecting noise exposure may implement various metrics, triggers, outputs, etc. in manners similar to the particle exposure embodiments described above.

Various computational elements including processors, memory, instructions, routines, models, or other components may be described or claimed as "configured to" perform a task or tasks. In such contexts, the phrase "configured to" is used to connote structure by indicating that the component includes structure (e.g., stored instructions, circuitry, etc.) that performs the task or tasks during operation. As such, the unit/circuit/component can be said to be configured to perform the task even when the specified component is not necessarily currently operational (e.g., is not on).

The components used with the "configured to" language may refer to hardware—for example, circuits, memory storing program instructions executable to implement the operation, etc. Additionally, "configured to" can refer to generic structure (e.g., generic circuitry) that is manipulated by software and/or firmware (e.g., an FPGA or a general-purpose processor executing software) to operate in manner that is capable of performing the recited task(s). Additionally, "configured to" can refer to one or more memories or memory elements storing computer executable instructions for performing the recited task(s). Such memory elements may include memory on a computer chip having processing logic. In some contexts, "configured to" may also include adapting a manufacturing process (e.g., a semiconductor fabrication facility) to fabricate devices (e.g., integrated circuits) that are adapted to implement or perform one or more tasks.

What is claimed is:

1. A system comprising:
    a monitoring unit positioned within an environment and including an acoustic sensor configured to generate detected acoustic data regarding acoustics in the environment; and
    a controller comprising one or more processors and one or more non-transitory memory devices that store instructions for controlling the one or more first processors to:
        receive and store the detected acoustic data,
        determine, based on the detected acoustic data, whether a noise is above a threshold, and
        determine, based on the detected acoustic data and that the noise is above the threshold, an estimated source of the noise.

2. The system of claim 1, wherein the estimated source of the noise is an activity performed in the environment.

3. The system of claim 1, further comprising a second sensor configured to generate second data, wherein:
    the sensor is selected from the group consisting of: a camera, a temperature sensor, a location sensor, an air quality sensor, and a gas sensor, and
    the one or more non-transitory memory devices stores further instructions for controlling the one or more processors to:
    receive and store the second data, and
    determine, based at least in part on the acoustic data and the second data, the source of the acoustics in the environment.

4. The system of claim 3, wherein:
    the second sensor is a location sensor configured to generate location data about a location of the monitoring unit, and
    the one or more non-transitory memory devices stores further instructions for controlling the one or more processors to determine, based at least in part on, the source of the noise.

5. The system of claim 1, further comprising a notification mechanism configured to present a person with a notification related to the detected acoustic data, wherein:
    the one or more non-transitory memory devices stores further instructions for controlling the one or more processors to cause, based on the detected acoustic data, the notification mechanism to present the person with the notification related to the detected acoustic data.

6. The system of claim 1, wherein the one or more non-transitory memory devices stores further instructions for controlling the one or more processors to determine whether a second noise will exceed a second threshold over a period of time in the future.

7. The system of claim 6, wherein the second noise is the noise.

8. The system of claim 1, wherein:
    the one or more non-transitory memory devices further stores acoustic information relating to associations between acoustic data and sources of acoustics, and
    the determination of the estimated source of the noise is further based on the acoustic information.

9. The system of claim 1, wherein the one or more non-transitory memory devices further stores acoustic information:
    relating to associations between acoustic data and functionality of sources of acoustics, and
    to determine whether a source of acoustics is functioning properly and/or should be maintained.

10. The system of claim 9, wherein the sources of acoustics include operating machinery, vehicles, or equipment.

11. A system comprising:
a monitoring unit positioned within an environment and including a temperature sensor configured to generate temperature data, and a relative humidity sensor configured to generate humidity data;
a notification mechanism configured to present a person with a notification related to a heat stress determination; and
a controller comprising one or more first processors and one or more first non-transitory memory devices that store instructions for controlling the one or more first processors to:
receive and store the temperature data and the humidity data,
determine, based on the temperature data and the humidity data, an estimated heat stress in the environment,
determine whether the estimated heat stress in the environment is above a threshold, and
cause, based on the heat stress determination, the notification mechanism to present the person with the notification related to the heat stress determination.

12. The system of claim 11, wherein the temperature data is ambient temperature around the monitoring unit.

13. The system of claim 11, wherein the temperature data is a body temperature of a person.

14. The system of claim 11, further comprising one or more additional sensors selected from the group consisting of a heart rate sensor and a light intensity sensor, wherein the determination of the estimated heat stress in the environment is further based on data generated by the one or more additional sensors.

15. The system of claim 11, wherein:
the one or more non-transitory memory devices further stores instructions to access climate information relating to climate information in the environment, and
the determination of the estimated heat stress in the environment is further based on the accessed climate information.

16. A system comprising:
a monitoring unit positioned within an environment and including a camera configured to generate image/video data of the environment; and
a controller comprising one or more first processors and one or more first non-transitory memory devices that store instructions for controlling the one or more first processors to:
cause the camera to generate image/video data,
receive and store the image/video data, and
determine, in real-time and based on the image/video data, an activity performed within the environment.

17. The system of claim 16, wherein:
the controller is positioned in the monitoring unit, and
the determination is made by the controller in the monitoring unit.

18. The system of claim 16, further comprising:
a first communications unit with an antenna configured to transmit data between the monitoring unit and, directly or indirectly, a remote computing unit, and
the remote computing unit positioned outside the environment and containing one or more second processors, one or more second communications unit, and one or more second non-transitory memory devices that stores instructions for controlling the one or more second processors, wherein:
the one or more first non-transitory memory devices further stores instructions for controlling the one or more first processors to transmit, using the first communications unit, the image/video data to the remote computing unit, and
the one or more second non-transitory memory devices stores instructions for controlling the one or more second processors to:
receive and store the image/video data, and
determine, based on the image/video data the activity performed within the environment.

19. The system of claim 16, further comprising an air quality sensor configured to generate particle data regarding particles in the environment and communicatively connected with the controller, wherein the one or more non-transitory memory devices further stores instructions to:
determine, based on the particle data generated by the air quality sensor, whether a first exposure threshold has been exceeded for the monitoring unit, and
cause the camera to take image/video data when a determination is made that the first exposure threshold has been exceeded.

20. A system comprising:
a monitoring unit positioned within an environment and including a gas sensor configured to generate concentration data of a gas in the environment; and
a controller comprising one or more first processors and one or more non-transitory memory devices that store gas information and instructions for controlling the one or more first processors to:
cause the gas sensor to generate concentration data of the gas in the environment,
receive and store the concentration data,
determine, based on the concentration data, a chemical composition of the gas in the environment,
access gas information, wherein the gas information relates to an association between the gas and one or more sources of the gas, and
determine, based on the chemical composition of the gas in the environment and the gas information, one or more sources of the gas.

21. The system of claim 20, wherein the one or more non-transitory memory devices further stores instructions for controlling the one or more first processors to determine whether the chemical composition is increasing or decreasing.

22. The system of claim 20, wherein the one or more non-transitory memory devices further stores instructions for controlling the one or more first processors to determine whether the chemical composition if the gas is above a threshold.

23. A system comprising:
a monitoring unit positioned within an environment and including:
a sensor configured to detect air particles, a gas, or acoustic signals in the environment and generate data regarding the detected air particles, the gas, or acoustic signals, and
a first communications unit with an antenna configured to transmit data between the monitoring unit and, directly or indirectly, a remote computing unit; and
a controller communicatively connected with the sensor and comprising one or more first processors and one or more first non-transitory memory devices that store instructions for controlling the one or more first processors to:

receive and store the data generated by the sensor,
access location information relating to a location of the monitoring unit within the environment,
determine, based on the data generated by the sensor and the location information, amounts or concentrations in the environment that are associated with the detected air particles, a gas, or acoustic signals, and
generate a map of the determined amounts or concentrations, in the environment, that are associated with the detected air particles, gas, or acoustic signals in the environment.

24. The system of claim 23, wherein the determined amounts or concentrations include datapoints interpolated from the data generated by the sensor.

25. The system of claim 23, wherein:
the one or more first non-transitory memory devices further store instructions for controlling the one or more first processors to access geographic information of the environment, and
the determination is further based on the geographic information of the environment.

26. The system of claim 23, wherein:
the one or more first non-transitory memory devices further store instructions for controlling the one or more first processors to access air flow data related to air flow within the environment, and
the determination is further based on the air flow data.

27. The system of claim 26, wherein the air flow data includes a flow rate and a direction of an air flow within the environment relative to the location of the monitoring unit within the environment.

28. The system of claim 26, wherein the air flow data includes data from one or more external sources.

29. The system of claim 23, wherein the one or more first non-transitory memory devices further store instructions for controlling the one or more first processors to determine, based on the data generated by the sensor, a location of a source of the detected air particles, gas, or acoustic signals in the environment.

30. A system comprising:
a monitoring unit positioned proximate to a boundary of an environment and including:
a sensor configured to detect air particles or a gas and generate data regarding the detected air particles or the gas, and
a first communications unit with an antenna configured to transmit data between the monitoring unit and, directly or indirectly, a remote computing unit;
a notification mechanism configured to generate a notification; and
a controller communicatively connected with the sensor and comprising one or more first processors and one or more first non-transitory memory devices that store instructions for controlling the one or more first processors to:
receive and store the data generated by the sensor,
access location information relating to a location of the monitoring unit,
determine, based at least in part on the data generated by the sensor, whether amounts or concentrations associated with the detected air particles or gas have exceeded a threshold,
determine, based at least in part on the data generated by the sensor and the location information, whether the detected air particles or gas are exiting or entering the environment, and
cause, based at least in part on the determinations, the notification mechanism to generate the notification related to the detected air particles or gas.

31. The system of claim 30, wherein the one or more non-transitory memory devices further stores instructions for controlling the one or more first processors to determine whether the amounts or concentrations associated with the detected air particles or gas is increasing or decreasing.

32. The system of claim 30, wherein:
the one or more first non-transitory memory devices further store instructions for controlling the one or more first processors to access air flow data related to air flow within and/or around the environment, and
the determination of whether the detected air particles or gas are exiting or entering the environment is further based on the air flow data.

33. The system of claim 32, wherein the air flow data includes a flow rate and a direction of an air flow within the environment relative to the location of the monitoring unit within the environment.

34. The system of claim 32, wherein the air flow data includes data from one or more external sources.

35. The system of claim 30, further comprising a camera configured to generate images and/or video of an area covering or near a portion of the boundary, wherein:
the determination of whether amounts or concentrations associated with the detected air particles or gas have exceeded a threshold is further based on the images and/or video generated by the camera, and
the determination of whether the detected air particles or gas are exiting or entering the environment is further based on the images and/or video generated by the camera.

36. The system of claim 30, further comprising a camera configured to generate images and/or video of an area covering or near a portion of the boundary, wherein:
the one or more first non-transitory memory devices further store instructions for controlling the one or more first processors to determine an opacity of air in the area covering or near the portion of the boundary,
the determination of whether amounts or concentrations associated with the detected air particles or gas have exceeded a threshold is further based on the opacity of the air, and
the determination of whether the detected air particles or gas are exiting or entering the environment is further based on the opacity of the air.

37. The system of claim 30, further comprising a laser sensor configured to generate distance data associated with a measured distance between the laser sensor and an object, wherein:
the determination of whether amounts or concentrations associated with the detected air particles or gas have exceeded a threshold is further based on the distance data, and
the determination of whether the detected air particles or gas are exiting or entering the environment is further based on the distance data.

* * * * *